United States Patent
Zion et al.

(10) Patent No.: US 8,846,103 B2
(45) Date of Patent: Sep. 30, 2014

(54) EXOGENOUSLY TRIGGERED CONTROLLED RELEASE MATERIALS AND USES THEREOF

(75) Inventors: Todd C. Zion, Marblehead, MA (US); Thomas M. Lancaster, Stoneham, MA (US)

(73) Assignee: SmartCells, Inc., Whitehouse Station, NJ (US)

( * ) Notice: Subject to any disclaimer, the term of this patent is extended or adjusted under 35 U.S.C. 154(b) by 73 days.

(21) Appl. No.: 13/145,530

(22) PCT Filed: Jan. 27, 2010

(86) PCT No.: PCT/US2010/022225
§ 371 (c)(1),
(2), (4) Date: Jul. 20, 2011

(87) PCT Pub. No.: WO2010/088268
PCT Pub. Date: Aug. 5, 2010

(65) Prior Publication Data
US 2012/0046223 A1    Feb. 23, 2012

Related U.S. Application Data

(60) Provisional application No. 61/147,878, filed on Jan. 28, 2009, provisional application No. 61/159,643, filed on Mar. 12, 2009, provisional application No. 61/162,107, filed on Mar. 20, 2009, provisional application No. 61/162,053, filed on Mar. 20, 2009, provisional application No. 61/162,058, filed on Mar. 20, 2009, provisional application No. 61/162,084, filed on Mar. 20, 2009, provisional application No. 61/162,092, filed on Mar. 20, 2009, provisional application No. 61/162,105, filed on Mar. 20, 2009, provisional application No. 61/163,084, filed on Mar. 25, 2009, provisional application No. 61/219,897, filed on Jun. 24, 2009, provisional application No. 61/223,572, filed on Jul. 7, 2009, provisional application No. 61/252,857, filed on Oct. 19, 2009.

(51) Int. Cl.
*A61K 9/16* (2006.01)
*A61K 9/10* (2006.01)

(52) U.S. Cl.
USPC ............ 424/493; 424/486; 424/488; 424/489; 424/490

(58) Field of Classification Search
USPC ............ 514/3, 19, 23, 53–54; 435/6, 7.1, 196; 424/488, 486, 489, 490, 493
See application file for complete search history.

(56) References Cited

U.S. PATENT DOCUMENTS

| | | |
|---|---|---|
| 3,591,574 A | 7/1971 | Fenichel et al. |
| 3,684,791 A | 8/1972 | Geiger et al. |
| 3,847,890 A | 11/1974 | Green et al. |
| 4,348,387 A | 9/1982 | Brownlee et al. |
| 4,372,948 A | 2/1983 | Yoshikumi et al. |
| 4,377,567 A | 3/1983 | Geho |
| 4,444,683 A | 4/1984 | Kim et al. |
| 4,603,044 A | 7/1986 | Geho et al. |
| 4,863,896 A | 9/1989 | Geho et al. |
| 5,239,062 A | 8/1993 | Blattler et al. |
| 5,395,924 A | 3/1995 | Blattler et al. |
| 5,478,575 A | 12/1995 | Miyazaki et al. |
| 5,527,524 A | 6/1996 | Tomalia et al. |
| 5,563,056 A * | 10/1996 | Swan et al. .................. 435/180 |
| 5,723,589 A | 3/1998 | Miljkovic et al. |
| 5,830,506 A | 11/1998 | Taylor |
| 5,854,208 A | 12/1998 | Jones et al. |
| 5,866,538 A | 2/1999 | Norup et al. |
| 5,902,607 A | 5/1999 | Taylor |
| 5,905,140 A | 5/1999 | Hansen |
| 5,922,675 A | 7/1999 | Baker et al. |
| 5,948,751 A | 9/1999 | Kimer et al. |
| 5,994,517 A | 11/1999 | Ts'o et al. |
| 6,034,054 A | 3/2000 | DeFelippis et al. |
| 6,180,757 B1 | 1/2001 | Bogsnes |
| 6,214,547 B1 | 4/2001 | Kjeldsen et al. |
| 6,323,311 B1 | 11/2001 | Liu et al. |

(Continued)

FOREIGN PATENT DOCUMENTS

| | | |
|---|---|---|
| CN | 101273961 | 10/2008 |
| EP | 009842 | 4/1980 |

(Continued)

OTHER PUBLICATIONS

Thisbe K. Lindhorst et al. Trivalent alpha-D-mannoside clusters as inhibitors of typr-1 fimbriae-mediated adhesion of *Escherichia coli*: structural variation and biotyinylation, J. Chem. Soc., Perkin trans 1, 2001, 823-832.*
International Search Report and Written Opinion for PCT/US10/22225, mailed on Mar. 9, 2010.
Lindhorst et al. Trivalent alpha-D-mannoside clusters as inhibitors of type-1 fimbriae-mediated adhesion of *Escherichia coli*: structural variation and biotinylation. J. Chem. Soc. Perkin Trans 1:823-831 (2001).
Baudys, et al., "Physical Stabilization of Insulin by Glycosylation" *J Pharma Sci* (1995) 64: 28-33.
Brownlee & Cerami, "A Glucose-Controlled-Insulin-Delivery-System: Semisynthetic Insulin Bound to Lectin" *Diabetes* (1983) 32:499-504.

(Continued)

*Primary Examiner* — Michael G Hartley
*Assistant Examiner* — Jagadishwar Samala
(74) *Attorney, Agent, or Firm* — Immac J. Thampoe; John David Reilly

(57) ABSTRACT

The disclosure provides cross-linked materials that include multivalent cross-linking agents that bind an exogenous target molecule; and conjugates that include two or more separate affinity ligands bound to a conjugate framework, wherein the two or more affinity ligands compete with the exogenous target molecule for binding with the cross-linking agents and wherein conjugates are cross-linked within the material as a result of non-covalent interactions between cross-linking agents and affinity ligands on different conjugates. The conjugates also include a drug.

11 Claims, 5 Drawing Sheets

(56) References Cited

U.S. PATENT DOCUMENTS

| | | | |
|---|---|---|---|
| 6,342,225 | B1 | 1/2002 | Jones et al. |
| 6,410,053 | B1 | 6/2002 | Taylor |
| 6,500,645 | B1 | 12/2002 | Kjeldsen et al. |
| 6,521,738 | B2 | 2/2003 | Kjeldsen et al. |
| 6,551,992 | B1 | 4/2003 | DeFelippis et al. |
| 6,777,207 | B2 | 8/2004 | Kjeldsen et al. |
| 6,844,166 | B1 | 1/2005 | Wolf |
| 6,869,930 | B1 | 3/2005 | Havelund et al. |
| RE39,055 | E | 4/2006 | Jones et al. |
| 7,063,863 | B2 | 6/2006 | Taylor |
| 7,087,408 | B2 | 8/2006 | Kjeldsen et al. |
| 7,105,314 | B2 | 9/2006 | Kjeldsen |
| 7,316,999 | B2 | 1/2008 | Hoeg-Jensen et al. |
| 7,317,000 | B2 | 1/2008 | Hoeg-Jensen et al. |
| 7,423,014 | B2 | 9/2008 | Ekwuribe et al. |
| 7,531,191 | B2 | 5/2009 | Zion et al. |
| 7,687,608 | B2 | 3/2010 | Lancaster et al. |
| 8,062,668 | B2 | 11/2011 | Ying et al. |
| 2002/0068295 | A1* | 6/2002 | Madou et al. ............ 435/6 |
| 2006/0019874 | A1 | 1/2006 | Radhakrishnan et al. |
| 2006/0216265 | A1 | 9/2006 | Goodman et al. |
| 2006/0247154 | A1 | 11/2006 | Palmieri et al. |
| 2007/0099820 | A1* | 5/2007 | Lancaster et al. ......... 514/3 |
| 2007/0207498 | A1 | 9/2007 | Palmieri et al. |
| 2009/0053167 | A1 | 2/2009 | DeFrees |
| 2009/0137454 | A1 | 5/2009 | Fynbo et al. |
| 2010/0130726 | A1 | 5/2010 | Lancaster et al. |
| 2011/0275560 | A1 | 11/2011 | Zion et al. |
| 2011/0281791 | A1 | 11/2011 | Zion et al. |
| 2011/0281792 | A1 | 11/2011 | Zion et al. |
| 2011/0281939 | A1 | 11/2011 | Zion et al. |
| 2011/0301083 | A1 | 12/2011 | Zion et al. |
| 2012/0046223 | A1 | 2/2012 | Zion et al. |

FOREIGN PATENT DOCUMENTS

| | | |
|---|---|---|
| EP | 119650 A2 | 8/1984 |
| EP | 0119650 | 9/1984 |
| EP | 0725648 | 8/1996 |
| RU | 2381238 | 8/2009 |
| WO | WO81/00354 | 2/1981 |
| WO | WO84/01896 | 5/1984 |
| WO | WO90/10645 | 9/1990 |
| WO | WO99/52934 | 10/1999 |
| WO | WO01/92334 | 12/2001 |
| WO | WO03/035011 | 5/2003 |
| WO | WO03/047462 | 6/2003 |
| WO | WO03/048915 | 6/2003 |
| WO | WO03047462 | 6/2003 |
| WO | WO03/074087 | 9/2003 |
| WO | WO2004/057002 | 7/2004 |
| WO | WO2006/008238 | 1/2006 |
| WO | WO2006/082184 | 8/2006 |
| WO | WO2006/088473 | 8/2006 |
| WO | WO2006082184 | 8/2006 |
| WO | WO2006088473 | 8/2006 |
| WO | WO2006/102762 | 10/2006 |
| WO | WO2006102762 | 10/2006 |
| WO | WO2007/042470 | 4/2007 |
| WO | WO2007/043050 | 4/2007 |
| WO | WO2008/012440 | 1/2008 |
| WO | WO2008/012528 | 1/2008 |
| WO | WO2008/036147 | 3/2008 |
| WO | WO2009/033588 | 3/2009 |
| WO | WO2009033588 | 3/2009 |
| WO | WO2009/059450 | 5/2009 |
| WO | WO2009059450 | 5/2009 |
| WO | WO2009/089396 | 7/2009 |
| WO | WO2009/104199 | 8/2009 |
| WO | WO2011/000823 | 1/2011 |
| WO | WO2011009823 | 1/2011 |

OTHER PUBLICATIONS

Brownlee & Cerami, "Glycosylated Insulin Complexed to Concanavalin A" *Science* (1979) 206: 1190-1191.

Dea, et al., "Albumin Binding of Acylated Insulin (NN304) Does Not Deter Action to Stimulate Glucose Uptake" *Diabetes* (2002) 51:762-769.

Eggert, et al., "A New Glucose Selective Fluorescent Bisboronic Acid" *J Org Chem* (1999) 64: 3846-3852.

Heinnemann, et al., "Time-action profile of the soluble, fatty acid acylated, long acting insulin analogue NN304" *Diabetic Med* (1999) 16: 332-338.

Jeong, et al., "Self Regulating Insulin Delivery Systems I. Synthesis and Characterization of Glycosylated Insulin" *J of Controlled Release* (1984) 1: 57-66.

Lee et al., "Biochemistry of crbohydrate-protein interaction" *FASEB J* (1992) 3193-3200.

Monsigny, et al., "Endogenous Lectins and Drug Targeting" *Annals NY Acad Sci* (1988) 551: 399-414.

Ruziak, et al., "Basal activity profiles of NPH and [Ne-palmitoyl Lys (B29) human insulins in subjects with IDDM" *Diabetologia* (1998) 41: 116-120.

Shojaee-Moradie, "Novel Hepatoselective Insulin Analog" *Diabetes Care* (2000) 23: 1124-1129.

Yamazaki, et al., "Endogenous lectins as targets for drug delivery" *Adv Drug Delivery Rev* (2000) 43: 225-244.

Lindhorst, et al., J. Chem. Soc., Perkin Trans. 1, 2001, pp. 823-831.

\* cited by examiner

```
                        SEQUENCE LISTING

<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

EXOGENOUSLY TRIGGERED CONTROLLED RELEASE MATERIALS AND USES THEREOF

RELATED APPLICATIONS

This application is a national phase application of International Application No. PCT/US2010/22225, filed Jan. 27, 2010, which claims priority to U.S. Provisional Application No. 61/147,878 filed Jan. 28, 2009, U.S. Provisional Application No. 61/159,643 filed Mar. 12, 2009, U.S. Provisional Application No. 61/162,107 filed Mar. 20, 2009, U.S. Provisional Application No. 61/162,053 filed Mar. 20, 2009, U.S. Provisional Application No. 61/162,058 filed Mar. 20, 2009, U.S. Provisional Application No. 61/162,084 filed Mar. 20, 2009, U.S. Provisional Application No. 61/162,092 filed Mar. 20, 2009, U.S. Provisional Application No. 61/162,105 filed Mar. 20, 2009, U.S. Provisional Application No. 61/163,084 filed Mar. 25, 2009, U.S. Provisional Application No. 61/219,897 filed Jun. 24, 2009, U.S. Provisional Application No. 61/223,572 filed Jul. 7, 2009, and U.S. Provisional Application No. 61/252,857 filed Oct. 19, 2009, the content of each of which is hereby incorporated by reference in its entirety.

In accordance with 37 CFR 1.52(e)(5), a Sequence Listing in the form of a text file (entitled "Sequence listing_0037.txt," created on Jan. 25, 2010, and 1 kilobyte) is incorporated herein by reference in its entirety.

BACKGROUND

The majority of "controlled-release" drug delivery systems operate by slowing or delaying the release of a drug post-administration. While these systems are useful for certain types of drugs (e.g., because they lead to fewer peaks and troughs in the serum profile, reduced side-effects, etc.) they are unsuitable for drugs that require more complex release profiles (e.g., release in proportion to an endogenous substance such as glucose, pulsatile release at fixed or variable time points, etc). For example, the treatment of diabetes mellitus with injectable insulin is a well-known and studied case where gradual slow release of insulin is ineffective. In fact, it is apparent that the simple replacement of the hormone is not sufficient to prevent the pathological sequelae associated with this disease. The development of these sequelae is believed to reflect an inability to provide exogenous insulin proportional to varying blood glucose concentrations experienced by the patient (i.e., a truly "controlled-release" system). As a result, there remains a need in the art for alternative controlled-release drug delivery systems and in particular systems that can be controlled post-administration. The present disclosure provides such systems.

SUMMARY

In one aspect, the disclosure provides cross-linked materials that include multivalent cross-linking agents that bind an exogenous target molecule; and conjugates that include two or more separate affinity ligands bound to a conjugate framework, wherein the two or more affinity ligands compete with the exogenous target molecule for binding with the cross-linking agents and wherein conjugates are cross-linked within the material as a result of non-covalent interactions between cross-linking agents and affinity ligands on different conjugates. The conjugates also include a drug. The drug and affinity ligands may be covalently or non-covalently bound to the conjugate framework. In general, these materials are designed so that an increase in the local concentration of exogenous target molecule triggers the release of conjugates. The disclosure also provides methods of using these materials wherein a triggering amount of the exogenous target molecule is administered to a patient who has previously been administered a material of the present disclosure. The disclosure also provides methods of making these materials. In another aspect, the disclosure provides exemplary cross-linked materials and exogenous target molecules.

DEFINITIONS

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987.

Acyl—As used herein, the term "acyl," refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Aliphatic—As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl—As used herein, the term "alkenyl" denotes an optionally substituted monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

Alkyl—As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiments, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to an optionally substituted monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents.

Arylalkyl—As used herein, the term "arylalkyl" refers to an alkyl group substituted with an aryl group (e.g., an aromatic or heteroaromatic group).

Bivalent hydrocarbon chain—As used herein, the term "bivalent hydrocarbon chain" (also referred to as a "bivalent alkylene group") is a polymethylene group, i.e., $-(CH_2)_z-$, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group.

Carbonyl—As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

Cycloaliphatic—As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaralkyl—As used herein, the term "heteroaralkyl" refers to an alkyl group substituted by a heteroaryl, wherein the alkyl and heteroaryl portions independently are optionally substituted.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}$Ph, which may be substituted with $R^\circ$; $-(CH_2)_{0-4}O(CH_2)_{0-1}$Ph which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NRO_2$; $-C(S)NRO_2$; $-C(S)SR^\circ$; $-SC(S)SR^\circ$; $-(CH_2)_{0-4}OC(O)NRO_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NRO_2$; $-(CH_2)_{0-4}S(O)R^\circ$; $-N(R^\circ)S(O)_2NRO_2$; $-N(R^\circ)S(O)_2R^\circ$; $-N(OR^\circ)R^\circ$; $-C(NH)NRO_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched)alkylene)O$-N(R^\circ)_2$; or $-(C_{1-4}$ straight or branched)alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R.$, -(haloR.), $-(CH_2)_{0-2}OH$, $-(CH_2)_{0-2}OR.$, $-(CH_2)_{0-2}CH(OR.)_2$; $-O(haloR.)$, $-CN$, $-N_3$, $-(CH_2)_{0-2}C(O)R.$, $-(CH_2)_{0-2}C(O)OH$, $-(CH_2)_{0-2}C(O)OR.$, $-(CH_2)_{0-2}SR.$, $-(CH_2)_{0-2}SH$, $-(CH_2)_{0-2}NH_2$, $-(CH_2)_{0-2}NHR.$, $-(CH_2)_{0-2}NR._2$, $-NO_2$, $-SiR._3$, $-OSiR._3$, $-C(O)SR.$, $-(C_{1-4}$ straight or branched alkylene)C(O)OR., or $-SSR.$ wherein each R. is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, $-O(C(R*_2))_{2-3}O-$, or $-S(C(R*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R., -(haloR.), —OH, —OR', —O(haloR.), —CN, —C(O)OH, —C(O)OR., —NH$_2$, —NHR., —NR.$_2$, or —NO$_2$, wherein each R. is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R., —(haloR.), —OH, —OR', —O(haloR.), —CN, —C(O)OH, —C(O)OR., —NH$_2$, —NHR., —NR.$_2$, or —NO$_2$, wherein each R. is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable protecting group—As used herein, the term "suitable protecting group," refers to amino protecting groups or hydroxyl protecting groups depending on its location within the compound and includes those described in detail in *Protecting Groups in Organic Synthesis*, T. W. Greene and P. G. M. Wuts, 3$^{rd}$ edition, John Wiley & Sons, 1999.

Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Agglutinated—When two or more cells are "agglutinated" by a cross-linking agent as described herein, they are each physically associated with the cross-linking agent in a cell-agent-cell complex. Typically, agglutination only occurs once the cross-linking agent concentration reaches a threshold concentration. This concentration is referred to as the minimum agglutination concentration (MAC). The MAC for a given cross-linking agent is commonly measured using a spectrophotometric plate reader that can quantify changes in solution absorbance.

Aptamer—As used herein, the term "aptamer" refers to a polynucleotide or polypeptide that binds specifically to a target molecule. In general, an aptamer is said to "bind specifically" to its target molecule if it associates at a detectable level with the target molecule and does not associate detectably with unrelated molecular entities (e.g., molecules which share no common structural features with the target molecule) under similar conditions. Specific association between a target molecule and an aptamer will typically be dependent upon the presence of a particular structural feature of the target molecule such as an epitope recognized by the aptamer. Generally, if an aptamer is specific for epitope A, the presence of a molecule containing epitope A or the presence of free unlabeled epitope A in a reaction containing both free labeled epitope A and the aptamer thereto, will reduce the amount of labeled epitope A that binds to the aptamer. In general, it is to be understood that specificity need not be absolute. Indeed, it is well known in the art that aptamers may cross-react with other epitopes in addition to the target epitope. Such cross-reactivity may be acceptable depending upon the application for which the aptamer is to be used. Thus the degree of specificity of an aptamer will depend on the context in which it is being used. It is also to be understood that specificity may be evaluated in the context of additional factors such as the affinity of the aptamer for the target molecule versus the affinity of the aptamer for non-target molecules.

Associated—As used herein, two entities are physically "associated" with one another when they are bound by direct non-covalent interactions. Desirable non-covalent interactions include those of the type which occur between an immunoglobulin molecule and an antigen for which the immunoglobulin is specific, for example, ionic interactions, hydrogen bonds, van der Waals interactions, hydrophobic interactions, etc. The strength, or affinity of the physical association can be expressed in terms of the dissociation constant ($K_d$) of the interaction, wherein a smaller $K_d$ represents a greater affinity. For example, the association properties of a selected cross-linking agent and target molecule can be quantified using methods well known in the art.

Biodegradable—As used herein, the term "biodegradable" refers to molecules that degrade (i.e., lose at least some of their covalent structure) under physiological or endosomal conditions. Biodegradable molecules are not necessarily hydrolytically degradable and may require enzymatic action to degrade.

Biomolecule—As used herein, the term "biomolecule" refers to molecules (e.g., polypeptides, amino acids, polynucleotides, nucleotides, polysaccharides, sugars, lipids, nucleoproteins, glycoproteins, lipoproteins, steroids, metabolites, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

Drug—As used herein, the term "drug" refers to small molecules or biomolecules that alter, inhibit, activate, or otherwise affect a biological event. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National formulary-20, published by the United States Pharmcopeial Convention, Inc., Rockville Md., 2001. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, are all considered acceptable for use in accordance with the present invention.

Exogenous—As used herein, an "exogenous" molecule is one which is not present at significant levels in a patient unless administered to the patient. In certain embodiments the patient is a human. As used herein, a molecule is not present at significant levels in a patient if normal human serum includes less than 0.1 mM of the molecule. In certain embodiments normal human serum may include less than 0.08 mM, less than 0.06 mM, or less than 0.04 mM of the molecule.

Hyperbranched—As used herein, a "hyperbranched" structure is a covalent structure that includes at least one branched branch (e.g., a dendrimeric structure). A hyperbranched structure may include polymeric and/or non-polymeric substructures.

Normal human serum—As used herein, "normal human serum" is human serum obtained by pooling approximately equal amounts of the liquid portion of coagulated whole blood from eight or more healthy individuals. A healthy individual is a randomly selected 18-30 year old who presents with no disease symptoms at the time blood is drawn.

Percentage homology—As used herein, the terms "percentage homology" refer to the percentage of sequence identity between two sequences after optimal alignment as defined in the present disclosure. For example, two nucleotide sequences are said to be "identical" if the sequence of nucleotides in the two sequences is the same when aligned for maximum correspondence as described below. Sequence comparisons between two nucleotide sequences are typically performed by comparing sequences of two optimally aligned sequences over a region or "comparison window" to identify and compare regions of sequence similarity. Optimal alignment of sequences for comparison may be conducted by the local homology algorithm of Smith and Waterman, *Ad. App. Math.* 2:482 (1981), by the homology alignment algorithm of Neddleman and Wunsch, *J. Mol. Biol.* 48:443 (1970), by the search for similarity method of Pearson and Lipman, *Proc. Natl. Acad. Sci. USA* 85:2444 (1988), by computerized implementation of these algorithms, or by visual inspection.

Percentage of sequence identity—"Percentage of sequence identity" is determined by comparing two optimally aligned sequences over a comparison window, where the portion of the nucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide residue occurs in both sequences to yield the number of matched positions, dividing the number of matched positions by the total number of positions in the window of comparison and multiplying the result by 100 to yield the percentage of sequence identity. This definition of sequence identity given above is the definition that would be used by one of ordinary skill in the art. The definition by itself does not need the help of any algorithm. The algorithms are only helpful to facilitate the optimal alignments of sequences, rather than calculate sequence identity. From this definition, it follows that there is a well defined and only one value for the sequence identity between two compared sequences which value corresponds to the value obtained for the optimal alignment.

Polymer—As used herein, a "polymer" or "polymeric structure" is a structure that includes a string of covalently bound monomers. A polymer can be made from one type of monomer or more than one type of monomer. The term "polymer" therefore encompasses copolymers, including block-copolymers in which different types of monomer are grouped separately within the overall polymer. A polymer can be linear or branched.

Polynucleotide—As used herein, a "polynucleotide" is a polymer of nucleotides. The terms "polynucleotide", "nucleic acid", and "oligonucleotide" may be used interchangeably. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl) uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

Polypeptide—As used herein, a "polypeptide" is a polymer of amino acids. The terms "polypeptide", "protein", "oligopeptide", and "peptide" may be used interchangeably. Polypeptides may contain natural amino acids, non-natural amino acids (i.e., compounds that do not occur in nature but that can be incorporated into a polypeptide chain) and/or amino acid analogs as are known in the art. Also, one or more of the amino acid residues in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. These modifications may include cyclization of the peptide, the incorporation of D-amino acids, etc.

Polysaccharide—As used herein, a "polysaccharide" is a polymer of saccharides. The terms "polysaccharide", "carbohydrate", and "oligosaccharide", may be used interchangeably. The polymer may include natural saccharides (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified saccharides (e.g., 2'-fluororibose, 2'-deoxyribose, and hexose). Exemplary disaccharides include sucrose, lactose, maltose, trehalose, gentiobiose, isomaltose, kojibiose, laminaribiose, mannobiose, melibiose, nigerose, rutinose, and xylobiose.

Small molecule—As used herein, the term "small molecule" refers to molecules, whether naturally-occurring or artificially created (e.g., via chemical synthesis), that have a relatively low molecular weight. Typically, small molecules are monomeric and have a molecular weight of less than about 1500 g/mol.

Treat—As used herein, the term "treat" (or "treating", "treated", "treatment", etc.) refers to the administration of a material of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition.

DETAILED DESCRIPTION OF CERTAIN EMBODIMENTS

Figure 1:
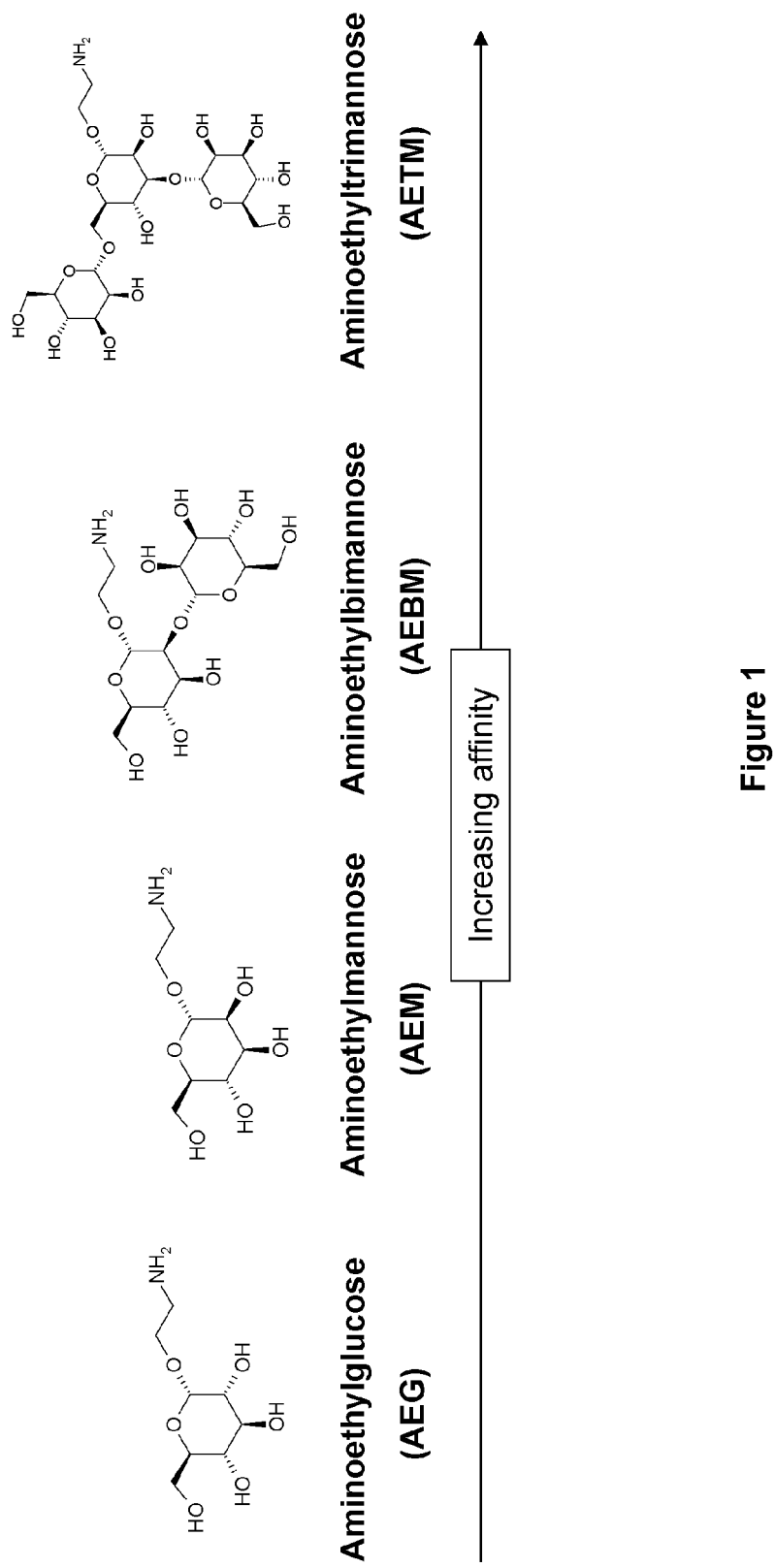
FIG. 1: shows the chemical structures of AEG, AEM, AEBM and AETM. The affinity of these sugar based affinity ligands for Con A increases as shown.

This application refers to a number of documents including patent and non-patent documents. The entirety of each of these documents is incorporated herein by reference. In one aspect, the disclosure provides cross-linked materials that include multivalent cross-linking agents that bind an exogenous molecule; and conjugates that include two or more separate affinity ligands bound to a conjugate framework, wherein the two or more affinity ligands compete with the exogenous molecule for binding with the cross-linking agents and wherein conjugates are cross-linked within the material as a result of non-covalent interactions between cross-linking agents and affinity ligands on different conjugates. The conjugates also include a drug. The drug and affinity ligands may be covalently or non-covalently bound to the conjugate framework. In general, these materials are designed so that an increase in the local concentration of exogenous molecule triggers the release of conjugates. The disclosure also provides methods of using these materials wherein a triggering amount of the exogenous target molecule is administered to a patient who has previously been administered a material of the present disclosure. The disclosure also provides methods of making these materials. In another aspect, the disclosure provides exemplary cross-linked materials and exogenous target molecules.

The cross-linking agents bind an exogenous molecule (e.g., without limitation α-methyl-mannose, mannose, L-fucose, N-acetyl glucosamine, a synthetic drug such as morphine, etc.) and are multivalent. The conjugates include a conjugate framework with two or more separate affinity ligands that compete with the exogenous molecule for binding with the cross-linking agents. When cross-linking agents and conjugates are combined in the absence of the exogenous molecule, a non-covalently cross-linked material is formed. When the material is placed in the presence of free exogenous molecules these compete for the interactions between the cross-linking agents and the conjugates. Above a certain concentration of free exogenous molecule, the level of competition becomes such that the material begins to degrade by releasing conjugates. As a result, conjugates are released from the material in a manner which is directly tied to the local concentration of the exogenous molecule. In various embodiments, the material releases substantially no conjugates in normal human serum. The latter property ensures that there is substantially no uncontrolled release of conjugates from the material in the absence of the exogenous molecule. As discussed below, in various embodiments it may be desirable to adjust the properties of the material so that it does release amounts of conjugate in normal human serum (e.g., to provide an endogenously controlled component in addition to an externally triggered component).

Exogenous Target Molecule

The present disclosure is not limited to any particular exogenous molecule. In the Examples we describe a material which is triggered by α-methyl-mannose. We chose this particular mannose derivative for purposes of illustrating the invention because it has a much higher affinity (about 40 fold) for the lectin concanavalin A (Con A) than endogenous glucose. This difference in binding affinity enabled us to use a Con A cross-linked material which does not release conjugates in response to endogenous levels of glucose and yet releases conjugates in response to exogenous α-methyl-mannose (see Example 1). It will be appreciated that other exogenous glucose or mannose derivatives with Con A binding affinities that are similar to (or greater than) α-methyl-mannose could have been used as exogenous target molecules for the material of Example 1. Without limitation these include, mannose, L-fucose, bimannose, methylbimannose, ethylbimmanose, trimannose, methyltrimannose, ethyltrimmanose, amino derivatives thereof, etc. Goldstein et al. provide a review of a number of Con A inhibitors and their relative affinities in *J. Biol. Chem.* 243: 2003-2007, 1968 and *Biochemistry.* 4: 876-883, 1965. Similarly, it is to be understood that other exogenous saccharides (and derivatives thereof) could be used with cross-linking agents (e.g., other lectins, aptamers, etc.) that recognize saccharides other than glucose or mannose. In fact, in certain embodiments, it may be advantageous to use a cross-linking agent that does not bind endogenous glucose. Exemplary lectins that do not bind glucose include those isolated from monocot plants such as *Galanthus nivalis, Allium sativum*, and *Allium ursinum*. As discussed below, one could also use aptamers that have been selected for their lack of glucose binding. Either of these approaches would reduce the risk of release triggered by fluctuations in endogenous levels of glucose. In various embodiments, this approach can be extended so as to avoid release in the presence of other endogenous molecules, e.g., other metabolites such as creatinine, urea, etc.

While the Examples and foregoing involve saccharide binding cross-linking agents and exogenous saccharides it is to be understood that the invention is not limited to such systems. Indeed, while lectin based systems will generally be limited to exogenous saccharides, aptamer based systems can be designed to bind many different exogenous molecules. For example, the inventive methods can be used to produce a cross-linked material which releases drug conjugates that neutralize the effects of an exogenous drug when the exogenous drug levels get too high, e.g., without limitation, a material that releases naltrexone conjugates in response to high levels of an opioid such as morphine, etc. This latter example highlights the fact that, in various embodiments, the exogenous molecule can be a molecule that is not intentionally administered to a patient. Thus, while the inventive materials and methods are useful for situations where the trigger is administered for the intentional purpose of releasing conjugates from a pre-administered material, they may also be useful in situations where the material is present to counteract non-prescribed ingestion, injection or inhalation of an exogenous molecule (e.g., an opioid such as morphine by a drug abuser).

Conjugates

The conjugates include two or more separate affinity ligands bound to a conjugate framework. The two or more separate affinity ligands compete with the exogenous target molecule for binding with the cross-linking agent. The conjugates also include a drug. The affinity ligands and drug may be covalently or non-covalently bound to the conjugate framework.

Affinity Ligands

The two or more separate affinity ligands may have the same or different chemical structures. The two or more separate affinity ligands may have the same chemical structure as the exogenous target molecule itself or may be a chemically related species of the exogenous target molecule. The only requirement is that they compete with the exogenous target molecule for binding with the cross-linking agent. In certain embodiments, the relative affinity of the conjugate and exogenous target molecule for the cross-linking agent is in the range of 1:1 to 100:1 (where a relative affinity of 100:1 means that, in an equilibrium mixture of conjugate, exogenous target molecule and cross-linking agent (in pH 7 HEPES buffered saline at 37 C), the cross-linking agent will bind about equal molar amounts of conjugate and exogenous target molecule if the concentration of exogenous target molecule is 100× the concentration of conjugate). In certain embodiments, the relative affinity is in the range of 1:1 to 50:1, 1:1 to 10:1, 1:1 to 5:1 or 1:1 to 2:1. In various embodiments it may be advantageous for the affinity ligands to have a different chemical structure from the exogenous target molecule, e.g., in order to fine tune the relative affinity of the cross-linking agent for the conjugates and the exogenous target molecule. For example, when the exogenous target molecule is α-methyl-mannose one might use a saccharide or a polysaccharide as one or more of affinity ligands. Thus, in certain embodiments, the affinity ligands are capable of competing with α-methyl-mannose for binding to a lectin (e.g., without limitation Con A, mannan-binding lectin or MBL, etc.).

In certain embodiments, the affinity ligand is of formula (IVa) or (IVb):

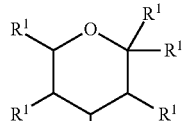

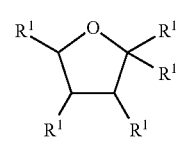

wherein:
each $R^1$ is independently hydrogen, $-OR^y$, $-N(R^y)_2$, $-SR^y$, $-O-Y$, -G-Z, or $-CH_2R^x$;
each $R^x$ is independently hydrogen, $-OR^y$, $-N(R^y)_2$, $-SR^y$, or $-O-Y$;
each $R^y$ is independently $-R^2$, $-SO_2R^2$, $-S(O)R^2$, $-P(O)(OR^2)_2$, $-C(O)R^2$, $-CO_2R^2$, or $-C(O)N(R^2)_2$;
each Y is independently a monosaccharide, disaccharide, or trisaccharide;
each G is independently a covalent bond or an optionally substituted $C_{1-9}$ alkylene, wherein one or more methylene units of G is optionally replaced by $-O-$, $-S-$, $-N(R)-$, $-C(O)-$, $-OC(O)-$, $-C(O)O-$, $-C(O)N(R^2)-$, $-N(R^2)C(O)-$, $-N(R^2)C(O)N(R^2)-$, $-SO_2-$, $-SO_2N(R^2)-$, $-N(R^2)SO_2-$, or $-N(R^2)SO_2N(R^2)-$;
each Z is independently halogen, $-N(R^2)_2$, $-OR^2$, $-SR^2$, $-N_3$, $-C\equiv R^2$, $-CO_2R^2$, $-C(O)R^2$, or $-OSO_2R^2$; and
each $R^2$ is independently hydrogen or an optionally substituted group selected from $C_{1-6}$ aliphatic, phenyl, a 4-7 membered heterocyclic ring having 1-2 heteroatoms selected from nitrogen, oxygen, or sulfur, or a 5-6 membered monocyclic heteroaryl ring having 1-4 heteroatoms selected from nitrogen, oxygen, or sulfur.

In certain embodiments, the affinity ligand of formula (IVa) or (IVb) is a monosaccharide. In certain embodiments, the affinity ligand is a disaccharide. In certain embodiments, the affinity ligand is a trisaccharide. In certain embodiments, the affinity ligand is a tetrasaccharide. In certain embodiments, the affinity ligand comprises no more than four saccharide moieties.

As defined generally above, each $R^1$ is independently hydrogen, $-OR^y$, $-N(R^y)_2$, $-SR^y$, $-O-Y$, -G-Z, or $-CH_2R^x$. In certain embodiments, $R^1$ is hydrogen. In certain embodiments, $R^1$ is $-OH$. In other embodiments, $R^1$ is $-NHC(O)CH_3$. In certain embodiments, $R^1$ is $-O-Y$. In certain other embodiments, $R^1$ is -G-Z. In some embodiments, $R^1$ is $-CH_2OH$. In other embodiments, $R^1$ is $-CH_2-O-Y$. In yet other embodiments, $R^1$ is $-NH_2$. One of ordinary skill in the art will appreciate that each $R^1$ substituent in formula (IVa) or (IVb) may be of (R) or (S) stereochemistry.

As defined generally above, each $R^x$ is independently hydrogen, $-OR^y$, $-N(R^y)_2$, $-SR^y$, or $-O-Y$. In some embodiments, $R^x$ is hydrogen. In certain embodiments, $R^x$ is $-OH$. In other embodiments, $R^x$ is $-O-Y$.

As defined generally above, each $R^y$ is independently $-R^2$, $-SO_2R^2$, $-S(O)R^2$, $-P(O)(OR^2)_2$, $-C(O)R^2$, $-CO_2R^2$, or $-C(O)N(R^2)_2$. In some embodiments, $R^y$ is hydrogen. In other embodiments, $R^y$ is $-R^2$. In some embodiments, $R^y$ is $-C(O)R^2$. In certain embodiments, $R^y$ is acetyl. In other embodiments, $R^y$ is $-SO_2R^2$, $-S(O)R^2$, $-P(O)(OR^2)_2$, $-CO_2R^2$, or $-C(O)N(R^2)_2$.

As defined generally above, Y is a monosaccharide, disaccharide, or trisaccharide. In certain embodiments, Y is a monosaccharide. In some embodiments, Y is a disaccharide. In other embodiments, Y is a trisaccharide. In some embodiments, Y is mannose, glucose, fructose, galactose, rhamnose, or xylopyranose. In some embodiments, Y is sucrose, maltose, turanose, trehalose, cellobiose, or lactose. In certain embodiments, Y is mannose. In certain embodiments, Y is D-mannose. One of ordinary skill in the art will appreciate that the saccharide Y is attached to the oxygen group of $-O-Y$ through anomeric carbon to form a glycosidic bond. The glycosidic bond may be of an alpha or beta configuration.

As defined generally above, each G is independently a covalent bond or an optionally substituted $C_{1-9}$ alkylene, wherein one or more methylene units of G is optionally replaced by $-O-$, $-S-$, $-N(R)-$, $-C(O)-$, $-OC(O)-$, $-C(O)O-$, $-C(O)N(R^2)-$, $-N(R^2)C(O)-$, $-N(R^2)C(O)N(R^2)-$, $-SO_2-$, $-SO_2N(R^2)-$, $-N(R^2)SO_2-$, or $-N(R^2)SO_2N(R^2)-$. In some embodiments, G is a covalent bond. In certain embodiments, G is $-O-C_{1-8}$ alkylene. In certain embodiments, G is $-OCH_2CH_2-$.

As defined generally above, each Z is independently halogen, $-N(R^2)_2$, $-OR^2$, $-SR^2$, $-N_3$, $-C\equiv R^2$, $-CO_2R^2$, $-C(O)R^2$, or $-OSO_2R^2$. In some embodiments, Z is a halogen or $-OSO_2R^2$. In other embodiments, Z is $-N_3$ or $-C\equiv R^2$. In certain embodiments, Z is $-N(R^2)_2$, $-OR^2$, or $-SR^2$. In certain embodiments, Z is $-SH$. In certain embodiments, Z is $-NH_2$. In certain embodiments, -G-Z is $-OCH_2CH_2NH_2$.

In some embodiments, the $R^1$ substituent on the C1 carbon of formula (IVa) is -G-Z to give a compound of formula (IVa-i):

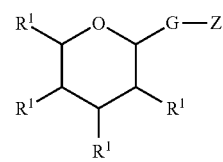

wherein $R^1$, G, and Z are as defined and described herein.

In some embodiments, the ligand is of formula (IVa-ii):

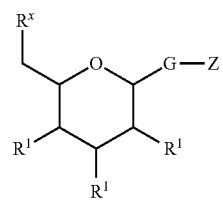

wherein $R^1$, $R^x$, G, and Z are as defined and described herein.

For example, in certain embodiments, one might use an affinity ligand that includes one or more of the following: glucose, sucrose, maltose, mannose, derivatives of these (e.g., glucosamine, mannosamine, methylglucose, methylmannose, ethylglucose, ethylmannose, etc.) and/or higher order combinations of these (e.g., a bimannose, a linear and/or branched trimannose, etc.). In certain embodiments, the affinity ligand includes a monosaccharide. In certain embodiments, the affinity ligand includes a disaccharide. In certain embodiments, the affinity ligand includes a trisaccharide. In certain embodiments, the affinity ligand includes a polysaccharide. In some embodiments, the affinity ligand includes a saccharide and one or more amine groups. In some embodiments, the affinity ligand is aminoethylglucose (AEG). In some embodiments, the affinity ligand is aminoethylmannose (AEM). In some embodiments, the affinity ligand is aminoethylbimannose (AEBM). In some embodiments, the affinity ligand is aminoethyltrimannose (AETM). In some embodiments, the affinity ligand is β-aminoethyl-N-acetylglucosamine (AEGA). In some embodiments, the affinity ligand is aminoethylfucose (AEF). In other embodiments, the affinity ligand is D-glucosamine (GA). In certain embodiments, a saccharide ligand is of the "D" configuration. In other embodiments, a saccharide ligand is of the "L" configuration. Below we show the structures of these exemplary affinity ligands. Other exemplary affinity ligands will be recognized by those skilled in the art.

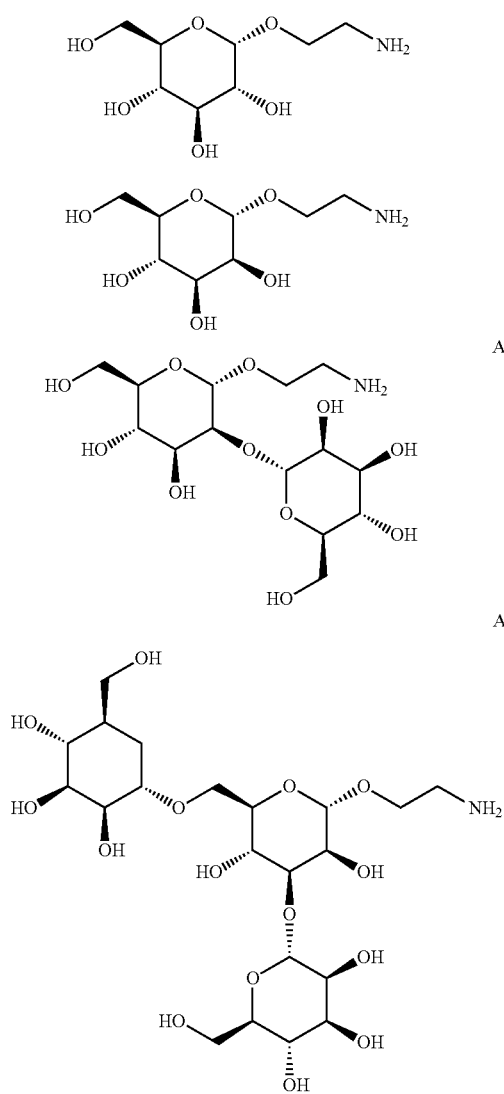

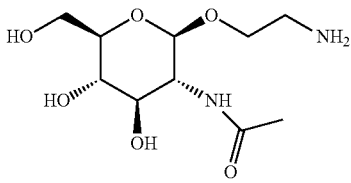

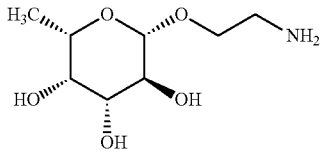

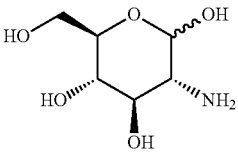

In various embodiments, the affinity ligand is a polysaccharide, glycopeptide or glycolipid. In certain embodiments, the affinity ligand includes from 2-10 saccharide moieties, e.g., 2, 3, 4, 5, 6, 7, 8, 9 or 10 moieties. The terminal and/or internal residues of the polysaccharide, glycopeptide or glycolipid may be selected based on the saccharide specificity of the lectin in question (e.g., see Goldstein et al., *Biochem. Biophys. Acta* 317:500-504, 1973 and L is et al., *Ann. Rev. Biochem.* 55:35-67, 1986).

In various embodiments, the affinity ligands for a particular conjugate/cross-linking agent combination may be selected empirically. According to such embodiments one or more affinity ligands are screened based on their relative binding affinities for the cross-linking agent as compared to the exogenous target molecule (and possibly endogenous molecules as discussed below). In certain embodiments a library of saccharides and/or polysaccharides are screened in this manner. A suitable affinity ligand will exhibit a detectable level of competition with the exogenous target molecule but will not compete so strongly that it prevents all binding between the cross-linking agent and the exogenous target molecule.

In various embodiments, the affinity ligand will be selected based on its ability to compete with endogenous molecules for the cross-linking agent. In particular, in certain embodiments it will be advantageous to select an affinity ligand that has a much higher affinity for the cross-linking agent than a potential competing endogenous molecule (e.g., glucose when the cross-linking agent is glucose binding) and yet can be competitively unbound by a suitable exogenous target molecule (e.g., α-methyl-mannose). This will minimize the extent of release from a cross-linked material in the absence of exogenous target molecule. For example, in Examples 1-2 we describe an exemplary conjugate with two AEBM affinity ligands that showed very little background release in the presence of physiological levels of endogenous glucose and yet produced a significant response to exogenous α-methyl-mannose. In other embodiments it may be desirable to select affinity ligands that allow for a certain amount of glucose responsive release and yet can be exogenously triggered in order to artificially modulate the release.

Other exemplary exogenous target molecule/affinity ligand combinations will be recognized by those skilled in the art. In general, an affinity ligand can be generated for any exogenous target molecule using the target molecule itself and/or by generating derivatives of the target molecule (e.g., by making chemical and/or stereochemical modifications to the target molecule and then screening the resulting derivative for its relative affinity to the cross-linking agent in question).

As discussed in more detail below, the affinity ligands may be naturally present within the framework of the conjugate (e.g., as part of a polymer backbone or as a side group of a monomer). Alternatively (or additionally) affinity ligands may be artificially incorporated into the conjugate framework (e.g., in the form of a chemical group that is synthetically added to a conjugate framework). In certain embodiments, a conjugate may include a framework which comprises 5 or more, 10 or more, 20 or more, 25 or more, 50 or more, or 100 or more affinity ligands. In certain embodiments, a conjugate may include a framework which comprises 2-5, 2-10, 2-20, 2-25, 2-50 or 2-100 affinity ligands. In certain embodiments, a conjugate may include a framework which comprises as few as 2, 3 or 4 separate affinity ligands.

Methods for conjugating affinity ligands to a conjugate framework are discussed in more detail below. In certain embodiments, when the affinity ligands include a saccharide, the conjugation (whether direct or indirect) involves the C1, C2 or C6 position of the saccharide. In certain embodiments, the conjugation involves the C1 position. The C1 position is also referred to as the anomeric carbon and may be connected to the conjugate framework in the alpha or beta conformation. In certain embodiments, the C1 position is configured as the alpha anomer. In other embodiments, the C1 position is configured as the beta anomer.

Drug

As noted above, the conjugate also comprises a drug. It is to be understood that a conjugate can comprise any drug. A conjugate can comprise more than one copy of the same drug and/or can comprise more than one type of drug. The conjugates are not limited to any particular drug and may include small molecule drugs or biomolecular drugs. In general, the drug(s) used will depend on the disease or disorder to be treated.

For example, without limitation, in various embodiments a conjugate can comprise any one of the following drugs: diclofenac, nifedipine, rivastigmine, methylphenidate, fluoroxetine, rosiglitazone, prednison, prednisolone, codeine, ethylmorphine, dextromethorphan, noscapine, pentoxiverine, acetylcysteine, bromhexine, epinephrine, isoprenaline, orciprenaline, ephedrine, fenoterol, rimiterol, ipratropium, cholinetheophyllinate, proxiphylline, bechlomethasone, budesonide, deslanoside, digoxine, digitoxin, disopyramide, proscillaridin, chinidine, procainamide, mexiletin, flecamide, alprenolol, proproanolol, nadolol, pindolol, oxprenolol, labetalol, tirnolol, atenolol, pentaeritrityltetranitrate, isosorbiddinitrate, isosorbidmononitrate, niphedipin, phenylamine, verapamil, diltiazem, cyclandelar, nicotinylalcholhol, inositolnicotinate, alprostatdil, etilephrine, prenalterol, dobutamine, dopamine, dihydroergotamine, guanetidine, betanidine, methyldopa, reserpine, guanfacine, trimethaphan, hydralazine, dihydralazine, prazosine, diazoxid, captopril, nifedipine, enalapril, nitroprusside, bendroflumethiazide, hydrochlorthiazide, metychlothiazide, polythiazide, chlorthalidon, cinetazon, clopamide, mefruside, metholazone, bumetanide, ethacrynacide, spironolactone, amiloride, chlofibrate, nicotinic acid, nicheritrol, brompheniramine, cinnarizine, dexchlorpheniramine, clemastine, antazoline, cyproheptadine, proethazine, cimetidine, ranitidine, sucralfat, papaverine, moxaverine, atropin, butylscopolamin, emepron, glucopyrron, hyoscyamine, mepensolar, methylscopolamine, oxiphencyclimine, probanteline, terodilin, sennaglycosides, sagradaextract, dantron, bisachodyl, sodiumpicosulfat, etulos, diphenolxylate, loperamide, salazosulfapyridine, pyrvin, mebendazol, dimeticon, ferrofumarate, ferrosuccinate, ferritetrasemisodium, cyanochobalamine, folid acid heparin, heparin co-factor, diculmarole, warfarin, streptokinase, urokinase, factor VIII, factor IX, vitamin K, thiopeta, busulfan, chlorambucil, cyclophosphamid, melfalan, carmustin, mercatopurin, thioguanin, azathioprin, cytarabin, vinblastin, vinchristin, vindesin, procarbazine, dacarbazine, lomustin, estramustin, teniposide, etoposide, cisplatin, amsachrin, aminogluthetimid, phosphestrol, medroxiprogresterone, hydroxiprogesterone, megesterol, noretisteron, tamoxiphen, ciclosporin, sulfosomidine, bensylpenicillin, phenoxymethylpenicillin, dicloxacillin, cloxacillin, flucoxacillin, ampicillin, amoxicillin, pivampicillin, bacampicillin, piperacillin, meziocillin, mecillinam, pivmecillinam, cephalotin, cephalexin, cephradin, cephydroxil, cephaclor, cefuroxim, cefotaxim, ceftazidim, cefoxitin, aztreonam, imipenem, cilastatin, tetracycline, lymecycline, demeclocycline, metacycline, oxitetracycline, doxycycline, chloramphenicol, spiramycin, fusidic acid, lincomycin, clindamycin, spectinomycin, rifampicin, amphotericin B, griseofulvin, nystatin, vancomycin, metronidazole, tinidazole, trimethoprim, norfloxacin, salazosulfapyridin, aminosalyl, isoniazid, etambutol, nitrofurantoin, nalidixic acid, metanamine, chloroquin, hydroxichloroquin, tinidazol, ketokonazol, acyclovir, interferon idoxuridin, retinal, tiamin, dexpantenol, pyridoxin, folic acid, ascorbic acid, tokoferol, phytominadion, phenfluramin, corticotropin, tetracosactid, tyrotropin, somatotoprin, somatrem, vasopressin, lypressin, desmopressin, oxytocin, chloriongonadotropin, cortison, hydrocortisone, fluodrocortison, prednison, prednisolon, fluoximesteron, mesterolon, nandrolon, stanozolol, oximetolon, cyproteron, levotyroxin, liotyronin, propylthiouracil, carbimazol, tiamazol, dihydrotachysterol, alfacalcidol, calcitirol, insulin, tolbutamid, chlorpropamid, tolazamid, glipizid, glibenclamid, phenobarbital, methyprylon, pyrityidion, meprobamat, chlordiazepoxid, diazepam, nitrazepam, baclofen, oxazepam, dikaliumclorazepat, lorazepam, flunitrazepam, alprazolam, midazolam, hydroxizin, dantrolene, chlomethiazol, propionmazine, alimemazine, chlorpromazine, levomepromazine, acetophenazine, fluphenazine, perphenazine, prochlorperazine, trifluoperazine, dixyrazine, thiodirazine, periciazin, chloprothixene, tizanidine, zaleplon, zuclopentizol, flupentizol, thithixen, haloperidol, trimipramin, opipramol, chlomipramin, desipramin, lofepramin, amitriptylin, nortriptylin, protriptylin, maptrotilin, caffeine, cinnarizine, cyclizine, dimenhydinate, meclozine, prometazine, thiethylperazine, metoclopramide, scopolamine, phenobarbital, phenyloine, ethosuximide, primidone, carbamazepine, chlonazepam, orphenadrine, atropine, bensatropine, biperiden, metixene, procylidine, levodopa, bromocriptin, amantadine, ambenon, pyridostigmine, synstigmine, disulfuram, morphine, codeine, pentazocine, buprenorphine, pethidine, phenoperidine, phentanyl, methadone, piritramide, dextropropoxyphene, ketobemidone, acetylsalicylic acid, celecoxib, phenazone, phenylbutazone, azapropazone, piroxicam, ergotamine, dihydroergotamine, cyproheptadine, pizitifen, flumedroxon, allopurinol, probenecid, sodiummaurothiomalate auronofin, penicillamine, estradiol, estradiolvalerianate, estriol, ethinylestradiol, dihydrogesteron, lynestrenol, medroxiprogesterone, noretisterone, cyclophenile, clomiphene, levonorgestrel, mestranol, ornidazol, tinidazol, ekonazol, chlotrimazol, natamycine, miconazole, sulbentin, methylergotamine, dinoprost, dinoproston, gemeprost, bromocriptine, phenylpropanolamine, sodiumchromoglicate, azetasolamide, dichlophenamide, betacarotene, naloxone, calciumfolinate, in particular clonidine, thephylline, dipyradamol, hydrochlothiazade, scopolamine, indomethacine, furosemide, potassium chloride, morphine, ibuprofen, salbutamol, terbutalin, calcitonin, etc. It is to be understood that this list is intended to be exemplary and that any drug, whether known or later discovered, may be used in a conjugate of the present disclosure.

In various embodiments, a conjugate may include a hormonal drug which may be peptidic or non-peptidic, e.g., adrenaline, noradrenaline, angiotensin, atriopeptin, aldosterone, dehydroepiandrosterone, androstenedione, testosterone, dihydrotestosterone, calcitonin, calcitriol, calcidiol, corticotropin, cortisol, dopamine, estradiol, estrone, estriol, erythropoietin, follicle-stimulating hormone, gastrin, ghrelin, glucagon, gonadotropin-releasing hormone, growth hormone, growth hormone-releasing hormone, human chorionic gonadotropin, histamine, human placental lactogen, insulin, insulin-like growth factor, inhibin, leptin, a leukotriene, lipotropin, melatonin, orexin, oxytocin, parathyroid hormone, progesterone, prolactin, prolactin-releasing hormone, a prostglandin, renin, serotonin, secretin, somatostatin, thrombopoietin, thyroid-stimulating hormone, thyrotropin-releasing hormone (or thyrotropin), thyrotropin-releasing hormone, thyroxine, triiodothyronine, vasopressin, etc. In certain embodiments, the hormone may be selected from glucagon, insulin, insulin-like growth factor, leptin, thyroid-stimulating hormone, thyrotropin-releasing hormone (or thyrotropin), thyrotropin-releasing hormone, thyroxine, and triiodothyronine. It is to be understood that this list is intended to be exemplary and that any hormonal drug, whether known or later discovered, may be used in a conjugate of the present disclosure.

In various embodiments, a conjugate may include a thyroid hormone.

In various embodiments, a conjugate may include an antidiabetic drug (i.e., a drug which has a beneficial effect on patients suffering from diabetes).

Figure 5:
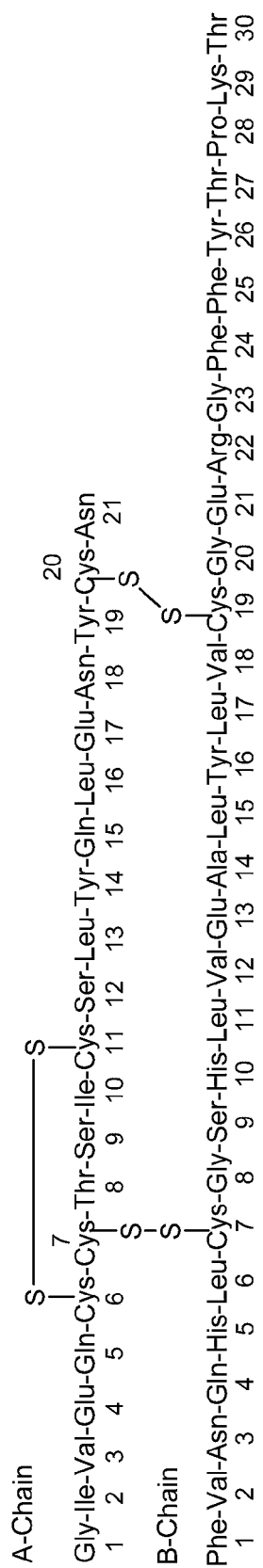
FIG. 5: shows the structure of wild-type human insulin.

In various embodiments, a conjugate may include an insulin molecule. By "an insulin molecule" we intend to encompass both wild-type and modified forms of insulin as long as they are bioactive (i.e., capable of causing a detectable reduction in glucose when administered in vivo). Wild-type insulin includes insulin from any species whether in purified, synthetic or recombinant form (e.g., human insulin, porcine insulin, bovine insulin, rabbit insulin, sheep insulin, etc.). A number of these are available commercially, e.g., from Sigma-Aldrich (St. Louis, Mo.). A variety of modified forms of insulin are known in the art (e.g. see Crotty and Reynolds, *Pediatr. Emerg. Care.* 23:903-905, 2007 and Gerich, *Am. J. Med.* 113:308-16, 2002 and references cited therein). Modified forms of insulin may be chemically modified (e.g., by addition of a chemical moiety such as a PEG group or a fatty acyl chain as described below) and/or mutated (i.e., by addition, deletion or substitution of one or more amino acids). In general, a bioactive mutant form of insulin will typically differ from wild-type insulin by 1-10 (e.g., from 1-5 or 1-2) amino acid substitutions, additions or deletions. The wild-type sequence of human insulin (A-chain and B-chain) is shown below and in FIG. 5.

```
A-Chain (SEQ ID NO: 1):
GIVEQCCTSICSLYQLENYCN

B-Chain (SEQ ID NO: 2):
FVNQHLCGSHLVEALYLVCGERGFFYTPKT
```

Human insulin differs from rabbit, porcine, bovine, and sheep insulin only in amino acids A8, A9, A10, and B30 (see table below).

| Insulin | Amino Acid Position | | | |
|---|---|---|---|---|
| | A8 | A9 | A10 | B30 |
| human | Thr | Ser | Ile | Thr |
| rabbit | Thr | Ser | Ile | Ser |
| porcine | Thr | Ser | Ile | Ala |
| bovine | Ala | Ser | Val | Ala |
| sheep | Ala | Gly | Val | Ala |

In various embodiments, an insulin molecule of the present disclosure is mutated at the B28 and/or B29 positions of the B-peptide sequence. For example, insulin lispro (HUMALOG®) is a rapid acting insulin mutant in which the penultimate lysine and proline residues on the C-terminal end of the B-peptide have been reversed ($Lys^{B28}Pro^{B29}$-human insulin). This modification blocks the formation of insulin multimers. Insulin aspart (NOVOLOG®) is another rapid acting insulin mutant in which proline at position B28 has been substituted with aspartic acid ($Asp^{B28}$-human insulin). This mutant also prevents the formation of multimers. In some embodiments, mutation at positions B28 and/or B29 is accompanied by one or more mutations elsewhere in the insulin polypeptide. For example, insulin glulisine (APIDRA®) is yet another rapid acting insulin mutant in which aspartic acid at position B3 has been replaced by a lysine residue and lysine at position B29 has been replaced with a glutamic acid residue ($Lys^{B3}Glu^{B29}$-human insulin).

In various embodiments, an insulin molecule of the present disclosure has an isoelectric point that is shifted relative to human insulin. In some embodiments, the shift in isoelectric point is achieved by adding one or more arginine residues to the N-terminus of the insulin A-peptide and/or the C-terminus of the insulin B-peptide. Examples of such insulin polypeptides include $Arg^{A0}$-human insulin, $Arg^{B31}Arg^{B32}$-human insulin, $Gly^{A21}Arg^{B31}Arg^{B32}$-human insulin, $Arg^{A0}Arg^{B31}Arg^{B32}$-human insulin, and $Arg^{A0}Gly^{A21}Arg^{B31}Arg^{B32}$-human insulin. By way of further example, insulin glargine (LANTUS®) is an exemplary long acting insulin mutant in which $Asp^{A21}$ has been replaced by glycine, and two arginine residues have been added to the C-terminus of the B-peptide. The effect of these changes is to shift the isoelectric point, producing a solution that is completely soluble at pH 4. Thus, in some embodiments, an insulin molecule of the present disclosure comprises an A-peptide sequence wherein A21 is Gly and B-peptide sequence wherein B31 is Arg-Arg. It is to be understood that the present disclosure encompasses all single and multiple combinations of these mutations and any other mutations that are described herein (e.g., $Gly^{A21}$-human insulin, $Gly^{A21}Arg^{B31}$-human insulin, $Arg^{B31}Arg^{B32}$-human insulin, $Arg^{B31}$-human insulin).

In various embodiments, an insulin molecule of the present disclosure is truncated. For example, in certain embodiments, a B-peptide sequence of an insulin polypeptide of the present disclosure is missing B1, B2, B3, B26, B27, B28, B29 and/or B30. In certain embodiments, combinations of residues are missing from the B-peptide sequence of an insulin polypeptide of the present disclosure. For example, the B-peptide sequence may be missing residues B(1-2), B(1-3), B(29-30), B(28-30), B(27-30) and/or B(26-30). In some embodiments, these deletions and/or truncations apply to any of the aforementioned insulin molecules (e.g., without limitation to produce des(B30)-insulin lispro, des(B30)-insulin aspart, des (B30)-insulin glulisine, des(B30)-insulin glargine, etc.).

In some embodiments, an insulin molecule contains additional amino acid residues on the N- or C-terminus of the A or B-peptide sequences. In some embodiments, one or more amino acid residues are located at positions A0, A21, B0 and/or B31. In some embodiments, one or more amino acid residues are located at position A0. In some embodiments, one or more amino acid residues are located at position A21. In some embodiments, one or more amino acid residues are located at position B0. In some embodiments, one or more amino acid residues are located at position B31. In certain embodiments, an insulin molecule does not include any additional amino acid residues at positions A0, A21, B0 or B31.

In certain embodiments, an insulin molecule of the present disclosure is mutated such that one or more amidated amino acids are replaced with acidic forms. For example, asparagine may be replaced with aspartic acid or glutamic acid. Likewise, glutamine may be replaced with aspartic acid or glutamic acid. In particular, $Asn^{A18}$, $Asn^{A21}$, or $Asn^{B3}$, or any combination of those residues, may be replaced by aspartic acid or glutamic acid. $Gln^{A15}$ or $Gln^{B4}$, or both, may be replaced by aspartic acid or glutamic acid. In certain embodiments, an insulin molecule has aspartic acid at position A21 or aspartic acid at position B3, or both.

One skilled in the art will recognize that it is possible to mutate yet other amino acids in the insulin molecule while retaining biological activity. For example, without limitation, the following modifications are also widely accepted in the art: replacement of the histidine residue of position B10 with aspartic acid ($His^{B10} \rightarrow Asp^{B10}$); replacement of the phenylalanine residue at position B1 with aspartic acid ($Phe^{B1} \rightarrow Asp^{B1}$); replacement of the threonine residue at position B30 with alanine ($Thr^{B30} \rightarrow Ala^{B30}$); replacement of the tyrosine residue at position B26 with alanine ($Tyr^{B26} \rightarrow Ala^{B26}$); and replacement of the serine residue at position B9 with aspartic acid ($Ser^{B9} \rightarrow Asp^{B9}$).

In various embodiments, an insulin molecule of the present disclosure has a protracted profile of action. Thus, in certain embodiments, an insulin molecule of the present disclosure may be acylated with a fatty acid. That is, an amide bond is formed between an amino group on the insulin molecule and the carboxylic acid group of the fatty acid. The amino group may be the alpha-amino group of an N-terminal amino acid of the insulin molecule, or may be the epsilon-amino group of a lysine residue of the insulin molecule. An insulin molecule of the present disclosure may be acylated at one or more of the three amino groups that are present in wild-type insulin or may be acylated on lysine residue that has been introduced into the wild-type sequence. In certain embodiments, an insulin molecule may be acylated at position B1. In certain embodiments, an insulin molecule may be acylated at position B29. In certain embodiments, the fatty acid is selected from myristic acid (C14), pentadecylic acid (C15), palmitic acid (C16), heptadecylic acid (C17) and stearic acid (C18). For example, insulin detemir (LEVEMIR®) is a long acting insulin mutant in which $Thr^{B30}$ has been deleted, and a C14 fatty acid chain (myristic acid) has been attached to $Lys^{B29}$.

In some embodiments, the N-terminus of the A-peptide, the N-terminus of the B-peptide, the epsilon-amino group of Lys at position B29 or any other available amino group in an insulin molecule of the present disclosure is covalently linked to a fatty acid moiety of general formula:

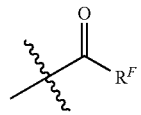

where $R^F$ is hydrogen or a $C_{1-30}$ alkyl group. In some embodiments, $R^F$ is a $C_{1-20}$ alkyl group, a $C_{3-19}$ alkyl group, a $C_{5-18}$ alkyl group, a $C_{6-17}$ alkyl group, a $C_{8-16}$ alkyl group, a $C_{10-15}$ alkyl group, or a $C_{12-14}$ alkyl group. In certain embodiments, the insulin polypeptide is conjugated to the moiety at the A1 position. In certain embodiments, the insulin polypeptide is conjugated to the moiety at the B1 position. In certain embodiments, the insulin polypeptide is conjugated to the moiety at the epsilon-amino group of Lys at position B29. In certain embodiments, position B28 of the insulin molecule is Lys and the epsilon-amino group of $Lys^{B28}$ is conjugated to the fatty acid moiety. In certain embodiments, position B3 of the insulin molecule is Lys and the epsilon-amino group of $Lys^{B3}$ is conjugated to the fatty acid moiety. In some embodiments, the fatty acid chain is 8-20 carbons long. In some embodiments, the fatty acid is octanoic acid (C8), nonanoic acid (C9), decanoic acid (C10), undecanoic acid (C11), dodecanoic acid (C12), or tridecanoic acid (C13). In certain embodiments, the fatty acid is myristic acid (C14), pentadecanoic acid (C15), palmitic acid (C16), heptadecanoic acid (C17), stearic acid (C18), nonadecanoic acid (C19), or arachidic acid (C20). For example, insulin detemir (LEVEMIR®) is a long acting insulin mutant in which $Thr^{B30}$ has been deleted, and a C14 fatty acid chain (myristic acid) is attached to $Lys^{B29}$.

In certain embodiments, an insulin molecule of the present disclosure comprises the mutations and/or chemical modifications of one of the following insulin molecules: $Lys^{B28}Pro^{B29}$-human insulin (insulin lispro), $Asp^{B28}$-human insulin (insulin aspart), $Lys^{B3}Glu^{B29}$-human insulin (insulin glulisine), $Arg^{B31}Arg^{B32}$-human insulin (insulin glargine), $N^{\epsilon B29}$-myristoyl-des(B30)-human insulin (insulin detemir), $Ala^{B26}$-human insulin, $Asp^{B1}$-human insulin, $Arg^{A20}$-human insulin, $Asp^{B1}Glu^{B13}$-human insulin, $Gly^{A21}$-human insulin, $Gly^{A21}Arg^{B31}Arg^{B32}$-human insulin, $Arg^{A0}$, $Arg^{B31}Arg^{B32}$-human insulin, $Arg^{A0}Gly^{A21}Arg^{B31}Arg^{B32}$-human insulin, des(B30)-human insulin, des(B27)-human insulin, des(B28-B30)-human insulin, des(B1)-human insulin, des(B1-B3)-human insulin.

In certain embodiments, an insulin molecule of the present disclosure comprises the mutations and/or chemical modifications of one of the following insulin molecules: $N^{\epsilon B29}$-palmitoyl-human insulin, $N^{\epsilon B29}$-myrisotyl-human insulin, $N^{\epsilon B28}$-palmitoyl-$Lys^{B28}Pro^{B29}$-human insulin, $N^{\epsilon B28}$-myristoyl-$Lys^{B28}Pro^{B29}$-human insulin.

In certain embodiments, an insulin molecule of the present disclosure comprises the mutations and/or chemical modifications of one of the following insulin molecules: $N^{\epsilon B29}$-palmitoyl-des(B30)-human insulin, $N^{\epsilon B30}$-myristoyl-$Thr^{B29}Lys^{B30}$-human insulin, $N^{\epsilon B30}$-palmitoyl-$Thr^{B29}Lys^{B30}$-human insulin, $N^{\epsilon B29}$-(N-palmitoyl-γ-glutamyl)-des(B30)-human insulin, $N^{\epsilon B29}$-(N-lithocolyl-γ-glutamyl)-des(B30)-human insulin, $N^{\epsilon B29}$-(ω-carboxyheptadecanoyl)-des(B30)-human insulin, $N^{\epsilon B29}$-(ω-carboxyheptadecanoyl)-human insulin.

In certain embodiments, an insulin molecule of the present disclosure comprises the mutations and/or chemical modifications of one of the following insulin molecules: $N^{\epsilon B29}$-octanoyl-human insulin, $N^{\epsilon B29}$-myristoyl-$Gly^{A21}Arg^{B31}Arg^{B31}$-human insulin, $N^{\epsilon B29}$-myristoyl- $N^{\epsilon B29}$-myristoyl-Arg$^{A21}$Gly$^{A21}$Arg$^{B31}$Arg$^{B32}$-human insulin, $N^{\epsilon B29}$-Arg$^{A0}$Gly$^{A21}$Gln$^{B3}$Arg$^{B31}$Arg$^{B32}$-human insulin, $N^{\epsilon B29}$-myristoyl-Arg$^{A0}$Gly$^{A21}$Asp$^{B3}$Arg$^{B31}$Arg$^{B32}$-human insulin, $N^{\epsilon B29}$-myristoyl-Arg$^{B31}$Arg$^{B32}$-human insulin, $N^{\epsilon B29}$-myristoyl-Arg$^{A0}$Arg$^{B31}$Arg$^{B32}$-human insulin, $N^{\epsilon B29}$-octanoyl-Gly$^{A21}$Arg$^{B31}$Arg$^{B32}$-human insulin, $N^{\epsilon B29}$-octanoyl-Gly$^{A21}$Gln$^{B3}$Arg$^{B31}$Arg$^{B32}$-human insulin, $N^{\epsilon B29}$-octanoyl-Arg$^{A0}$Gly$^{A21}$Arg$^{B31}$Arg$^{B32}$-human insulin, $N^{\epsilon B29}$-octanoyl-Arg$^{A0}$Gly$^{A21}$Gln$^{B3}$Arg$^{B31}$Arg$^{B32}$-human insulin, $N^{\epsilon B29}$-octanoyl-Arg$^{B0}$Gly$^{A21}$Asp$^{B3}$Arg$^{B31}$Arg$^{B32}$-human insulin, $N^{\epsilon B29}$-octanoyl-Arg$^{B31}$Arg$^{B32}$-human insulin, $N^{\epsilon B29}$-octanoyl-Arg$^{A0}$Arg$^{B31}$Arg$^{B32}$-human insulin.

In certain embodiments, an insulin molecule of the present disclosure comprises the mutations and/or chemical modifications of one of the following insulin polypeptides: $N^{\epsilon B28}$-myristoyl-Gly$^{A21}$Lys$^{B28}$Pro$^{B29}$Arg$^{B31}$Arg$^{B32}$-human insulin, $N^{\epsilon B28}$-myristoyl-Gly$^{A21}$Gln$^{B3}$Lys$^{B28}$Pro$^{B30}$Arg$^{B31}$Arg$^{B32}$-human insulin, $N^{\epsilon B28}$-myristoyl-Arg$^{A0}$Gly$^{A21}$Lys$^{B28}$Pro$^{B29}$Arg$^{B31}$Arg$^{B32}$-human insulin, $N^{\epsilon B28}$-myristoyl-Arg$^{A0}$Gly$^{A21}$Gln$^{B3}$Lys$^{B28}$Pro$^{B29}$Arg$^{B31}$Arg$^{B32}$-human insulin, $N^{\epsilon B28}$-myristoyl-Arg$^{A0}$Gly$^{A21}$Asp$^{B3}$Lys$^{B28}$Pro$^{B}$29Arg$^{B31}$Arg$^{B32}$-human insulin, $N^{\epsilon B28}$-myristoyl-Lys$^{B28}$Pro$^{B29}$Arg$^{B31}$Arg$^{B32}$-human insulin, $N^{\epsilon B28}$-myristoyl-arg$^{A0}$Lys$^{B28}$Pro$^{B29}$Arg$^{B31}$Arg$^{B32}$-human insulin, $N^{\epsilon B28}$-octanoyl-Gly$^{A21}$Lys$^{B28}$Pro$^{B29}$Arg$^{B31}$Arg$^{B32}$-human insulin.

In certain embodiments, an insulin molecule of the present disclosure comprises the mutations and/or chemical modifications of one of the following insulin molecules: $N^{\epsilon B28}$-octanoyl-Gly$^{A21}$Gln$^{B3}$Lys$^{B28}$Pro$^{B29}$Arg$^{B31}$Arg$^{B32}$-human insulin, $N^{\epsilon B28}$-octanoyl-Arg$^{A0}$Gly$^{A21}$Lys$^{B28}$Pro$^{B29}$Arg$^{B31}$Arg$^{B32}$-human insulin, $N^{\epsilon B28}$-octanoyl-Arg$^{A0}$Gly$^{A21}$Gln$^{B3}$Lys$^{B28}$Pro$^{B29}$Arg$^{B31}$Arg$^{B32}$-human insulin, $N^{\epsilon B28}$-octanoyl-Arg$^{A0}$Gly$^{A21}$Asp$^{B3}$Lys$^{B28}$Pro$^{B}$29Arg$^{B31}$Arg$^{B32}$-human insulin, $N^{\epsilon B28}$-octanoyl-Lys$^{B28}$Pro$^{B29}$Arg$^{B31}$Arg$^{B32}$-human insulin, $N^{\epsilon B28}$-octanoyl-Arg$^{A0}$Lys$^{B28}$Pro$^{B29}$Arg$^{B31}$Arg$^{B32}$-human insulin.

In certain embodiments, an insulin molecule of the present disclosure comprises the mutations and/or chemical modifications of one of the following insulin molecules: $N^{\epsilon B29}$-tridecanoyl-des(B30)-human insulin, $N^{\epsilon B29}$-tetradecanoyl-des(B30)-human insulin, $N^{\epsilon B29}$-decanoyl-des (B30)-human insulin, $N^{\epsilon B29}$-dodecanoyl-des(B30)-human insulin, $N^{\epsilon B29}$-tridecanoyl-Gly$^{A21}$-des(B30)-human insulin, $N^{\epsilon B29}$-tetradecanoyl-Gly$^{A21}$-des(B30)-human insulin, $N^{\epsilon B29}$-decanoyl-Gly$^{A21}$-des(B30)-human insulin, $N^{\epsilon B29}$-dodecanoyl-Gly$^{A21}$-des(B30)-human insulin, $N^{\epsilon B29}$-tridecanoyl-Gly$^{A21}$Gln$^{B3}$-des(B30)-human insulin, $N^{\epsilon B29}$-tetradecanoyl-Gly$^{A21}$Gln$^{B3}$-des(B30)-human insulin, $N^{\epsilon B29}$-decanoyl-Gly$^{A21}$Gln$^{B3}$-des(B30)-human insulin, $N^{\epsilon B29}$-dodecanoyl-Gly$^{A21}$-Gln$^{B3}$-des(B30)-human insulin, $N^{\epsilon B29}$-tridecanoyl-Ala$^{A21}$-des(B30)-human insulin, $N^{\epsilon B29}$-tetradecanoyl-Ala$^{A21}$-des(B30)-human insulin, $N^{\epsilon B29}$-decanoyl-Ala$^{A21}$-des(B30)-human insulin, $N^{\epsilon B29}$-dodecanoyl-Ala$^{A21}$-des(B30)-human insulin, $N^{\epsilon B29}$-tridecanoyl-Ala$^{A21}$-Gln$^{B3}$-des(B30)-human insulin, $N^{\epsilon B29}$-tetradecanoyl-Ala$^{A21}$Gln$^{B3}$-des(B30)-human insulin, $N^{\epsilon B29}$-decanoyl-Ala$^{A21}$Gln$^{B3}$-des(B30)-human insulin, $N^{\epsilon B29}$-dodecanoyl-Ala$^{A21}$Gln$^{B3}$-des(B30)-human insulin, $N^{\epsilon B29}$-tridecanoyl-Gln$^{B3}$-des(B30)-human insulin, $N^{\epsilon B29}$-tetradecanoyl-Gln$^{B3}$-des(B30)-human insulin, $N^{\epsilon B29}$-decanoyl-Gln$^{B3}$-des(B30)-human insulin, $N^{\epsilon B29}$-dodecanoyl-Gln$^{B3}$-des(B30)-human insulin.

In certain embodiments, an insulin molecule of the present disclosure comprises the mutations and/or chemical modifications of one of the following insulin molecules: $N^{\epsilon B29}$-tridecanoyl-Gly$^{A21}$-human insulin, $N^{\epsilon B29}$-tetradecanoyl-Gly$^{A21}$-human insulin, $N^{\epsilon B29}$-decanoyl-Gly$^{A21}$-human insulin, $N^{\epsilon B29}$-dodecanoyl-Gly$^{A21}$-human insulin, $N^{\epsilon B29}$-tridecanoyl-Ala$^{A21}$-human insulin, $N^{\epsilon B29}$-tetradecanoyl-Ala$^{A21}$-human insulin, $N^{\epsilon B29}$-decanoyl-Ala$^{A21}$-human insulin, $N^{\epsilon B29}$-dodecanoyl-Ala$^{A21}$-human insulin.

In certain embodiments, an insulin molecule of the present disclosure comprises the mutations and/or chemical modifications of one of the following insulin molecules: $N^{\epsilon B29}$-tridecanoyl-Gly$^{A21}$Gln$^{B3}$-human insulin, $N^{\epsilon B29}$-tetradecanoyl-Gly$^{A21}$Gln$^{B3}$-human insulin, $N^{\epsilon B29}$-decanoyl-Gly$^{A21}$Gln$^{B3}$-human insulin, $N^{\epsilon B29}$-dodecanoyl-Gly$^{A21}$Gln$^{B3}$-human insulin, $N^{\epsilon B29}$-tridecanoyl-Ala$^{A21}$Gln$^{B3}$-human insulin, $N^{\epsilon B29}$-tetradecanoyl-Ala$^{A21}$Gln$^{B3}$-human insulin, $N^{\epsilon B29}$-decanoyl-Ala$^{A21}$Gln$^{B3}$-human insulin, $N^{\epsilon B29}$-dodecanoyl-Ala$^{A21}$Gln$^{B3}$-human insulin.

In certain embodiments, an insulin molecule of the present disclosure comprises the mutations and/or chemical modifications of one of the following insulin molecules: $N^{\epsilon B29}$-tridecanoyl-Gln$^{B3}$-human insulin, $N^{\epsilon B29}$-tetradecanoyl-Gln$^{B3}$-human insulin, $N^{\epsilon B29}$-decanoyl-Gln$^{B3}$-human insulin, $N^{\epsilon B29}$-dodecanoyl-Gln$^{B3}$-human insulin.

In certain embodiments, an insulin molecule of the present disclosure comprises the mutations and/or chemical modifications of one of the following insulin molecules: $N^{\epsilon B29}$-tridecanoyl-Glu$^{B30}$-human insulin, $N^{\epsilon B29}$-tetradecanoyl-Glu$^{B30}$-human insulin, $N^{\epsilon B29}$-decanoyl-Glu$^{B30}$-human insulin, $N^{\epsilon B29}$-dodecanoyl-Glu$^{B30}$-human insulin.

In certain embodiments, an insulin molecule of the present disclosure comprises the mutations and/or chemical modifications of one of the following insulin molecules: $N^{\epsilon B29}$-tridecanoyl-Gly$^{A21}$Glu$^{B30}$-human insulin, $N^{\epsilon B29}$-tetradecanoyl-Gly$^{A21}$Glu$^{B30}$-human insulin, $N^{\epsilon B29}$-decanoyl-Gly$^{A21}$Glu$^{B30}$-human insulin, $N^{\epsilon B29}$-dodecanoyl-Gly$^{A21}$Glu$^{B30}$-human insulin. In certain embodiments, an insulin molecule of the present disclosure comprises the mutations and/or chemical modifications of one of the following insulin molecules: $N^{\epsilon B29}$-tridecanoyl-Gly$^{A21}$Gln$^{B3}$Glu$^{B30}$-human insulin, $N^{\epsilon B29}$-tetradecanoyl-Gly$^{A21}$Gln$^{B3}$Glu$^{B30}$-human insulin, $N^{\epsilon B29}$-decanoyl-Gly$^{A21}$Gln$^{B3}$Glu$^{B30}$-human insulin, $N^{\epsilon B29}$-dodecanoyl-Gly$^{A21}$Gln$^{B3}$, Glu$^{B30}$-human insulin, $N^{\epsilon B29}$-tridecanoyl-Ala$^{A21}$Glu$^{B30}$-human insulin, $N^{\epsilon B29}$-tetradecanoyl-Ala$^{A21}$Glu$^{B30}$-human insulin, $N^{\epsilon B29}$-decanoyl-Ala$^{A21}$Glu$^{B30}$-human insulin, $N^{\epsilon B29}$-dodecanoyl-Ala$^{A21}$Glu$^{B30}$-human insulin, $N^{\epsilon B29}$-tridecanoyl-Ala$^{A21}$Gln$^{B3}$Glu$^{B30}$-human insulin, $N^{\epsilon B29}$-tetradecanoyl-Ala$^{A21}$Gln$^{B3}$Glu$^{B30}$-human insulin, $N^{\epsilon B29}$-decanoyl-Ala$^{A21}$Gln$^{B3}$Glu$^{B30}$-human insulin, $N^{\epsilon B29}$-dodecanoyl-Ala$^{A21}$Gln$^{B3}$Glu$^{B30}$-human insulin.

In certain embodiments, an insulin molecule of the present disclosure comprises the mutations and/or chemical modifications of one of the following insulin molecules: $N^{\epsilon B29}$-tridecanoyl-Gln$^{B3}$Glu$^{B30}$-human insulin, $N^{\epsilon B29}$-tetradecanoyl-Gln$^{B3}$Glu$^{B30}$-human insulin, $N^{\epsilon B29}$-decanoyl-Gln$^{B3}$Glu$^{B30}$-human insulin, $N^{\epsilon B29}$-dodecanoyl-Gln$^{B3}$Glu$^{B30}$-human insulin. In certain embodiments, an insulin molecule of the present disclosure comprises the mutations and/or chemical modifications of one of the following insulin molecules: $N^{\epsilon B29}$-formyl-human insulin, $N^{\alpha B1}$-formyl-human insulin, $N^{\alpha A1}$-formyl-human insulin, $N^{\epsilon B29}$-formyl-$N^{\alpha B1}$-formyl-human insulin, $N^{\epsilon B29}$-formyl-$N^{\alpha A1}$-formyl-human insulin, $N^{\alpha A1}$-formyl-$N^{\alpha B1}$-formyl-human insulin, $N^{\epsilon B29}$-formyl-$N^{\alpha A1}$-formyl-$N^{\alpha B1}$-formyl-human insulin.

In certain embodiments, an insulin molecule of the present disclosure comprises the mutations and/or chemical modifications of one of the following insulin molecules: $N^{\epsilon B29}$-acetyl-human insulin, $N^{\alpha B1}$-acetyl-human insulin, $N^{\alpha A1}$-acetyl-human insulin, $N^{\epsilon B29}$-acetyl-$N^{\alpha B1}$-acetyl-human insulin, $N^{\epsilon B29}$-acetyl-$N^{\alpha A1}$-acetyl-human insulin, $N^{\alpha A1}$-acetyl-$N^{\alpha B1}$-acetyl-human insulin, $N^{\epsilon B29}$-acetyl-$N^{\alpha A1}$-acetyl-$N^{\alpha B1}$-acetyl-human insulin.

In certain embodiments, an insulin molecule of the present disclosure comprises the mutations and/or chemical modifications of one of the following insulin molecules: $N^{\epsilon B29}$-propionyl-human insulin, $N^{\alpha B1}$-propionyl-human insulin, $N^{\alpha A1}$-propionyl-human insulin, $N^{\epsilon B29}$-acetyl-$N^{\alpha B1}$-propionyl-human insulin, $N^{\epsilon B29}$-propionyl-$N^{\epsilon A1}$-propionyl-human insulin, $N^{\alpha A1}$-propionyl-$N^{\alpha B1}$-propionyl-human insulin, $N^{\epsilon B29}$-propionyl-$N^{\alpha A1}$-propionyl-$N^{\alpha B1}$-propionyl-human insulin.

In certain embodiments, an insulin molecule of the present disclosure comprises the mutations and/or chemical modifications of one of the following insulin molecules: $N^{\epsilon B29}$-butyryl-human insulin, $N^{\alpha B1}$-butyryl-human insulin, $N^{\alpha A1}$-butyryl-human insulin, $N^{\epsilon B29}$-butyryl-$N^{\alpha B1}$-butyryl-human insulin, $N^{\epsilon B29}$-butyryl-$N^{\alpha A1}$-butyryl-human insulin, $N^{\alpha A1}$-butyryl-$N^{\alpha B1}$-butyryl-human insulin, $N^{\epsilon B29}$-butyryl-$N^{\alpha A1}$-butyryl-$N^{\alpha B1}$-butyryl-human insulin.

In certain embodiments, an insulin molecule of the present disclosure comprises the mutations and/or chemical modifications of one of the following insulin molecules: $N^{\epsilon B29}$-pentanoyl-human insulin, $N^{\alpha B1}$-pentanoyl-human insulin, $N^{\alpha B1}$-pentanoyl-human insulin, $N^{\epsilon B29}$-pentanoyl-$N^{\alpha B1}$-pentanoyl-human insulin, $N^{\epsilon B29}$-pentanoyl-$N^{\alpha A1}$-pentanoyl-human insulin, $N^{\alpha A1}$-pentanoyl-$N^{\alpha B1}$-pentanoyl-human insulin, $N^{\epsilon B29}$-pentanoyl-$N^{\alpha A1}$-pentanoyl-$N^{\alpha B1}$-pentanoyl-human insulin.

In certain embodiments, an insulin molecule of the present disclosure comprises the mutations and/or chemical modifications of one of the following insulin molecules: $N^{\epsilon B29}$-hexanoyl-human insulin, $N^{\alpha B1}$-hexanoyl-human insulin, $N^{\alpha A1}$-hexanoyl-human insulin, $N^{\epsilon B29}$-hexanoyl-$N^{\alpha B1}$-hexanoyl-human insulin, $N^{\epsilon B29}$-hexanoyl-$N^{\alpha A1}$-hexanoyl-human insulin, $N^{\alpha A1}$-hexanoyl-$N^{\alpha B1}$-hexanoyl-human insulin, $N^{\epsilon B29}$-hexanoyl-$N^{\alpha A1}$-hexanoyl-$N^{\alpha B1}$-hexanoyl-human insulin.

In certain embodiments, an insulin molecule of the present disclosure comprises the mutations and/or chemical modifications of one of the following insulin molecules: $N^{\epsilon B29}$-heptanoyl-human insulin, $N^{\alpha B1}$-heptanoyl-human insulin, $N^{\alpha A1}$-heptanoyl-human insulin, $N^{\epsilon B29}$-heptanoyl-$N^{\alpha B1}$-heptanoyl-human insulin, $N^{\epsilon B29}$-heptanoyl-$N^{\alpha A1}$-heptanoyl-human insulin, $N^{\alpha A1}$-heptanoyl-$N^{\alpha B1}$-heptanoyl-human insulin, $N^{\epsilon B29}$-heptanoyl-$N^{\alpha A1}$-heptanoyl-$N^{\alpha B1}$-heptanoyl-human insulin.

In certain embodiments, an insulin molecule of the present disclosure comprises the mutations and/or chemical modifications of one of the following insulin molecules: $N^{\alpha B1}$-octanoyl-human insulin, $N^{\alpha A1}$-octanoyl-human insulin, $N^{\epsilon B29}$-octanoyl-$N^{\alpha B1}$-octanoyl-human insulin, $N^{\epsilon B29}$-octanoyl-$N^{\alpha A1}$-octanoyl-human insulin, $N^{\alpha A1}$-octanoyl-$N^{\alpha B1}$-octanoyl-human insulin, $N^{\epsilon B29}$-octanoyl-$N^{\alpha A1}$-octanoyl-$N^{\alpha B1}$-octanoyl-human insulin.

In certain embodiments, an insulin molecule of the present disclosure comprises the mutations and/or chemical modifications of one of the following insulin molecules: $N^{\epsilon B29}$-nonanoyl-human insulin, $N^{\alpha B1}$-nonanoyl-human insulin, $N^{\alpha A1}$-nonanoyl-human insulin, $N^{\epsilon B29}$-nonanoyl-$N^{\alpha B1}$-nonanoyl-human insulin, $N^{\epsilon B29}$-nonanoyl-$N^{\alpha A1}$-nonanoyl-human insulin, $N^{\alpha A1}$-nonanoyl-$N^{\alpha B1}$-nonanoyl-human insulin, $N^{\epsilon B29}$-nonanoyl-$N^{\alpha A1}$-nonanoyl-$N^{\alpha B1}$-nonanoyl-human insulin.

In certain embodiments, an insulin molecule of the present disclosure comprises the mutations and/or chemical modifications of one of the following insulin molecules: $N^{\epsilon B29}$-decanoyl-human insulin, $N^{\alpha B1}$-decanoyl-human insulin, $N^{\alpha A1}$-decanoyl-human insulin, $N^{\epsilon B29}$-decanoyl-$N^{\alpha B1}$-decanoyl-human insulin, $N^{\epsilon B29}$-decanoyl-$N^{\alpha A1}$-decanoyl-human insulin, $N^{\alpha A1}$-decanoyl-$N^{\alpha B1}$-decanoyl-human insulin, $N^{\epsilon B29}$-decanoyl-$N^{\alpha A1}$-decanoyl-$N^{\alpha B1}$-decanoyl-human insulin.

In certain embodiments, an insulin molecule of the present disclosure comprises the mutations and/or chemical modifications of one of the following insulin molecules: $N^{\epsilon B28}$-formyl-Lys$^{B28}$Pro$^{B29}$-human insulin, $N^{\alpha B1}$-formyl-Lys$^{B28}$Pro$^{B29}$-human insulin, $N^{\alpha A1}$-formyl-Lys$^{B28}$Pro$^{B29}$-human insulin, $N^{\epsilon B28}$-formyl-$N^{\alpha B1}$-formyl-Lys$^{B28}$Pro$^{B29}$-human insulin, $N^{\epsilon B28}$-human insulin, $N^{\alpha A1}$-formyl-$N^{\alpha B1}$-formyl-Lys$^{B28}$Pro$^{B29}$-human formyl-$N^{\alpha A1}$-formyl-Lys$^{B28}$Pro$^{B29}$-insulin, $N^{\epsilon B28}$-formyl-$N^{\alpha A1}$-formyl-$N^{\alpha B1}$-formyl-Lys$^{B28}$Pro$^{B29}$-human insulin, $N^{\epsilon B29}$-acetyl-Lys$^{B28}$Pro$^{B29}$-human insulin, $N^{\alpha A1}$-acetyl-Lys$^{B28}$Pro$^{B29}$-human insulin, $N^{\epsilon B28}$-acetyl-$N^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-acetyl-$N^{\alpha A1}$-acetyl-Lys$^{B28}$Pro$^{B29}$-human insulin, $N^{\alpha A1}$-acetyl-$N^{\alpha B1}$-acetyl-Lys$^{B28}$Pro$^{B29}$-human insulin, $N^{\alpha B28}$-acetyl-$N^{\alpha A1}$-acetyl-$N^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-propionyl-Lys$^{B28}$Pro$^{B29}$Pro$^{B28}$-human insulin, $N^{\alpha B1}$-propionyl-Lys$^{B28}$Pro$^{B29}$-human insulin, $N^{\alpha A1}$-propionyl-Lys$^{B28}$Pro$^{B29}$-human insulin, $N^{\epsilon B28}$-propionyl-$N^{\alpha B1}$-propionyl-Lys$^{B28}$Pro$^{B29}$-human insulin, $N^{\epsilon B28}$-propionyl-$N^{\alpha A1}$-propionyl-Lys$^{B28}$Pro$^{B29}$-human insulin, $N^{\alpha A1}$-propionyl-$N^{\alpha B1}$-propionyl-Lys$^{B28}$Pro$^{B29}$-human insulin, $N^{\epsilon B28}$-propionyl-$N^{\alpha A1}$-propionyl-$N^{\alpha B1}$-propionyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-butyryl-Lys$^{B28}$Pro$^{B29}$-human insulin, $N^{\alpha B1}$-butyryl-Lys$^{B28}$Pro$^{B29}$-human insulin, $N^{\alpha A1}$-butyryl-Lys$^{B28}$Pro$^{B29}$-human insulin, $N^{\epsilon B28}$-butyryl-$N^{\alpha B1}$-butyryl-Lys$^{B28}$Pro$^{B29}$-human insulin, $N^{\epsilon B28}$-butyryl-$N^{\alpha A1}$-butyryl-Lys$^{B28}$Pro$^{B29}$-human insulin, $N^{\alpha A1}$-butyryl-$N^{\alpha B1}$-butyryl-Lys$^{B28}$Pro$^{B29}$-human insulin, $N^{\epsilon B28}$-butyryl-$N^{\alpha A1}$-butyryl-$N^{\alpha B1}$-butyryl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-pentanoyl-Lys$^{B28}$Pro$^{B29}$-human insulin, $N^{\alpha B1}$-pentanoyl-Lys$^{B28}$Pro$^{B29}$-human insulin, $N^{\alpha A1}$-pentanoyl-Lys$^{B28}$Pro$^{B29}$-human insulin, $N^{\epsilon B28}$-pentanoyl-$N^{\alpha B1}$-pentanoyl-Lys$^{B28}$Pro$^{B29}$-human insulin, $N^{\epsilon B28}$-pentanoyl-$N^{\alpha A1}$-pentanoyl-Lys$^{B28}$Pro$^{B29}$-human insulin, $N^{\alpha A1}$-pentanoyl-$N^{\alpha B1}$-pentanoyl-Lys$^{B28}$Pro$^{B29}$-human insulin, $N^{\epsilon B28}$-pentanoyl-$N^{\alpha A1}$-pentanoyl-$N^{\alpha B1}$-pentanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$- hexanoyl-Lys$^{B28}$Pro$^{B29}$-human insulin, N$^{\alpha B1}$-hexanoyl-Lys$^{B28}$Pro$^{B29}$-human insulin, N$^{\alpha A1}$-hexanoyl-Lys$^{B28}$Pro$^{B29}$-human insulin, N$^{\epsilon B28}$-hexanoyl-N$^{\alpha B1}$-hexanoyl-Lys$^{B28}$Pro$^{B29}$-human insulin, N$^{\epsilon B28}$-hexanoyl-N$^{\alpha A1}$-hexanoyl-Lys$^{B28}$Pro$^{B29}$-human insulin, N$^{\alpha A1}$-hexanoyl-N$^{\alpha B1}$-hexanoyl-Lys$^{B28}$Pro$^{B29}$-human insulin, N$^{\epsilon B28}$-hexanoyl-N$^{\alpha A1}$-hexanoyl-N$^{\alpha B1}$-hexanoyl-Lys$^{B28}$Pro$^{B}$29-human insulin.

In certain embodiments, an insulin molecule of the present disclosure comprises the mutations and/or chemical modifications of one of the following insulin molecules: N$^{\epsilon B28}$-heptanoyl-Lys$^{B28}$Pro$^{B29}$-human insulin, N$^{\alpha B1}$-heptanoyl-Lys$^{B28}$Pro$^{B29}$-human insulin, N$^{\alpha A1}$-heptanoyl-Lys$^{B28}$Pro$^{B29}$-human insulin, N$^{\epsilon B28}$-heptanoyl-N$^{\alpha B1}$-heptanoyl-Lys$^{B28}$Pro$^{B29}$-human insulin, N$^{\epsilon B28}$-heptanoyl-N$^{\alpha A1}$-heptanoyl-Lys$^{B28}$Pro$^{B29}$-human insulin, N$^{\alpha A1}$-heptanoyl-N$^{\alpha B1}$-heptanoyl-Lys$^{B28}$Pro$^{B29}$-human insulin, N$^{\epsilon B28}$-heptanoyl-N$^{\alpha A1}$-heptanoyl-N$^{\alpha B1}$-heptanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-octanoyl-Lys$^{B28}$Pro$^{B29}$-human insulin, N$^{\alpha B1}$-octanoyl-Lys$^{B28}$Pro$^{B29}$-human insulin, N$^{\alpha A1}$-octanoyl-Lys$^{B28}$Pro$^{B29}$-human insulin, N$^{\epsilon B28}$-octanoyl-N$^{\alpha B1}$-octanoyl-Lys$^{B28}$Pro$^{B29}$-human insulin, N$^{\epsilon B28}$-octanoyl-N$^{\alpha A1}$-octanoyl-Lys$^{B28}$Pro$^{B29}$-human insulin, N$^{\alpha A1}$-octanoyl-N$^{\alpha B1}$-octanoyl-Lys$^{B}$28Pro$^{B29}$-human insulin, N$^{\epsilon B28}$-octanoyl-N$^{\alpha A1}$-octanoyl-N$^{\alpha B1}$-octanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-nonanoyl-Lys$^{B28}$Pro$^{B29}$-human insulin, N$^{\alpha B1}$-nonanoyl-Lys$^{B28}$Pro$^{B29}$-human insulin, N$^{\alpha A1}$-nonanoyl-Lys$^{B28}$Pro$^{B29}$-human insulin, N$^{\epsilon B28}$-nonanoyl-N$^{\alpha B1}$-nonanoyl-Lys$^{B28}$Pro$^{B29}$-human insulin, N$^{\epsilon B28}$-nonanoyl-N$^{\alpha A1}$-nonanoyl-Lys$^{B28}$Pro$^{B29}$-human insulin, N$^{\alpha A1}$-nonanoyl-N$^{\alpha B1}$-nonanoyl-Lys$^{B28}$Pro$^{B29}$-human insulin, N$^{\epsilon B28}$-nonanoyl-N$^{\alpha A1}$-nonanoyl-N$^{\alpha B1}$-nonanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-decanoyl-Lys$^{B28}$Pro$^{B29}$-human insulin, N$^{\alpha B1}$-decanoyl-Lys$^{B28}$Pro$^{B29}$-human insulin, N$^{\alpha A1}$-decanoyl-Lys$^{B28}$Pro$^{B29}$-human insulin, N$^{\epsilon B28}$-decanoyl-N$^{\alpha B1}$-decanoyl-Lys$^{B28}$Pro$^{B29}$-human insulin, N$^{\epsilon B28}$-decanoyl-N$^{\alpha A1}$-decanoyl-Lys$^{B28}$Pro$^{B29}$-human insulin, N$^{\alpha A1}$-decanoyl-N$^{\alpha B1}$-decanoyl-Lys$^{B28}$Pro$^{B29}$-human insulin, N$^{\epsilon B28}$-decanoyl-N$^{\alpha A1}$-decanoyl-N$^{\alpha B1}$-decanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B29}$-pentanoyl-Gly$^{A21}$Arg$^{B31}$Arg$^{B32}$-human insulin, N$^{\alpha B1}$-hexanoyl-Gly$^{A21}$Arg$^{B31}$Arg$^{B32}$-human insulin, N$^{\alpha A1}$-heptanoyl-Gly$^{A21}$Arg$^{B31}$Arg$^{B32}$-human insulin, N$^{\epsilon B29}$-octanoyl-N$^{\alpha B1}$-octanoyl-Gly$^{A21}$Arg$^{B31}$Arg$^{B32}$-human insulin, N$^{\epsilon B29}$-propionyl-N$^{\alpha A1}$-propionyl-Gly$^{A21}$Arg$^{B31}$Arg$^{B32}$-human insulin, N$^{\alpha A1}$-acetyl-N$^{\alpha B1}$-acetyl-Gly$^{A21}$Arg$^{B31}$Arg$^{B32}$-human insulin, N$^{\epsilon B29}$-formyl-N$^{\alpha A1}$-formyl-N$^{\alpha B1}$-formyl-Gly$^{A21}$Arg$^{B31}$Arg$^{B32}$-human insulin, N$^{\epsilon B29}$-formyl-des(B26)-human insulin, N$^{\alpha B1}$-acetyl-Asp$^{B28}$-human insulin, N$^{\epsilon B29}$-propionyl-N$^{\alpha A1}$-propionyl-N$^{\alpha B1}$-propionyl-Asp$^{B1}$Asp$^{B3}$Asp$^{B21}$-human insulin, N$^{\epsilon B29}$-pentanoyl-Gly$^{A21}$-human insulin, N$^{\alpha B1}$-hexanoyl-Gly$^{A21}$-human insulin, N$^{\alpha A1}$-heptanoyl-Gly$^{A21}$-human insulin, N$^{\epsilon B29}$-octanoyl-N$^{\alpha B1}$-octanoyl-Gly$^{A21}$-human insulin, N$^{\epsilon B29}$-propionyl-N$^{\alpha A1}$-propionyl-Gly$^{A21}$-human insulin, N$^{\alpha A1}$-acetyl-N$^{\alpha B1}$-acetyl-Gly$^{A21}$-human insulin, N$^{\epsilon B29}$-formyl-N$^{\alpha A1}$-formyl-N$^{\alpha B1}$-formyl-Gly$^{A21}$-human insulin, N$^{\epsilon B29}$-butyryl-des(B30)-human insulin, N$^{\alpha B1}$-butyryl-des(B30)-human insulin, N$^{\alpha A1}$-butyryl-des(B30)-human insulin, N$^{\epsilon B29}$-butyryl-N$^{\alpha B1}$-butyryl-des(B30)-human insulin, N$^{\epsilon B29}$-butyryl-N$^{\alpha A1}$-butyryl-des(B30)-human insulin, N$^{\alpha A1}$-butyryl-N$^{\alpha B1}$-butyryl-des(B30)-human insulin, N$^{\epsilon B29}$-butyryl-N$^{\alpha A1}$-butyryl-N$^{\alpha B1}$-butyryl-des(B30)-human insulin.

The present disclosure also encompasses modified forms of non-human insulins (e.g., porcine insulin, bovine insulin, rabbit insulin, sheep insulin, etc.) that comprise any one of the aforementioned mutations and/or chemical modifications.

These and other modified insulin molecules are described in detail in U.S. Pat. Nos. 6,906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929; 5,504,188; 5,474,978; 5,461,031; and 4,421,685; and in U.S. Pat. Nos. 7,387,996; 6,869,930; 6,174,856; 6,011,007; 5,866,538; and 5,750,497, the entire disclosures of which are hereby incorporated by reference.

In various embodiments, an insulin molecule of the present disclosure includes the three wild-type disulfide bridges (i.e., one between position 7 of the A-chain and position 7 of the B-chain, a second between position 20 of the A-chain and position 19 of the B-chain, and a third between positions 6 and 11 of the A-chain).

Methods for conjugating drugs including insulin molecules are described below. In certain embodiments, an insulin molecule is conjugated to the conjugate framework via the A1 amino acid residue. In certain embodiments the A1 amino acid residue is glycine. It is to be understood however, that the present disclosure is not limited to N-terminal conjugation and that in certain embodiments an insulin molecule may be conjugated via a non-terminal A-chain amino acid residue. In particular, the present disclosure encompasses conjugation via the epsilon-amine group of a lysine residue present at any position in the A-chain (wild-type or introduced by site-directed mutagenesis). It will be appreciated that different conjugation positions on the A-chain may lead to different reductions in insulin activity. In certain embodiments, an insulin molecule is conjugated to the conjugate framework via the B1 amino acid residue. In certain embodiments the B1 amino acid residue is phenylalanine. It is to be understood however, that the present disclosure is not limited to N-terminal conjugation and that in certain embodiments an insulin molecule may be conjugated via a non-terminal B-chain amino acid residue. In particular, the present disclosure encompasses conjugation via the epsilon-amine group of a lysine residue present at any position in the B-chain (wild-type or introduced by site-directed mutagenesis). For example, in certain embodiments an insulin molecule may be conjugated via the B29 lysine residue. In the case of insulin glulisine, conjugation to the conjugate framework via the B3 lysine residue may be employed. It will be appreciated that different conjugation positions on the B-chain may lead to different reductions in insulin activity.

In certain embodiments, the ligands are conjugated to more than one conjugation point on a drug such as an insulin molecule. For example, an insulin molecule can be conjugated at both the A1 N-terminus and the B29 lysine. In some embodiments, amide conjugation takes place in carbonate buffer to conjugate at the B29 and A1 positions, but not at the B1 position. In other embodiments, an insulin molecule can be conjugated at the A1 N-terminus, the B1 N-terminus, and the B29 lysine. In yet other embodiments, protecting groups are used such that conjugation takes place at the B1 and B29 or B1 and A1 positions. It will be appreciated that any combination of conjugation points on an insulin molecule may be employed. In some embodiments, at least one of the conjugation points is a mutated lysine residue, e.g., $Lys^{43}$.

In various embodiments, a conjugate may include an insulin sensitizer (i.e., a drug which potentiates the action of insulin). Drugs which potentiate the effects of insulin include biguanides (e.g., metformin) and glitazones. The first glitazone drug was troglitazone which turned out to have severe side effects. Second generation glitazones include pioglitazone and rosiglitazone which are better tolerated although rosiglitazone has been associated with adverse cardiovascular events in certain trials.

In various embodiments, a conjugate may include an insulin secretagogue (i.e., a drug which stimulates insulin secretion by beta cells of the pancreas). For example, in various embodiments, a conjugate may include a sulfonylurea. Sulfonylureas stimulate insulin secretion by beta cells of the pancreas by sensitizing them to the action of glucose. Sulfonylureas can, moreover, inhibit glucagon secretion and sensitize target tissues to the action of insulin. First generation sulfonylureas include tolbutamide, chlorpropamide and carbutamide. Second generation sulfonylureas which are active at lower doses include glipizide, glibenclamide, gliclazide, glibornuride and glimepiride. In various embodiments, a conjugate may include a meglitinide. Suitable meglitinides include nateglinide, mitiglinide and repaglinide. Their hypoglycemic action is faster and shorter than that of sulfonylureas. Other insulin secretagogues include glucagon-like peptide 1 (GLP-1) and GLP-1 analogs (i.e., a peptide with GLP-1 like bioactivity that differs from GLP-1 by 1-10 amino acid substitutions, additions or deletions and/or by a chemical modification). GLP-1 reduces food intake by inhibiting gastric emptying, increasing satiety through central actions and by suppressing glucagon release. GLP-1 lowers plasma glucose levels by increasing pancreas islet cell proliferation and increases insulin production following food consumption. GLP-1 may be chemically modified, e.g., by lipid conjugation as in liraglutide to extend its in vivo half-life. Yet other insulin secretagogues include exendin-4 and exendin-4 analogs (i.e., a peptide with exendin-4 like bioactivity that differs from exendin-4 by 1-10 amino acid substitutions, additions or deletions and/or by a chemical modification). Exendin-4, found in the venom of the Gila Monster, exhibits GLP-1 like bioactivity. It has a much longer half-life than GLP-1 and, unlike GLP-1, it can be truncated by 8 amino acid residues at its N-terminus without losing bioactivity. The N-terminal region of GLP-1 and exendin-4 are almost identical, a significant difference being the second amino acid residue, alanine in GLP-1 and glycine in exendin-4, which gives exendin-4 its resistance to in vivo digestion. Exendin-4 also has an extra 9 amino acid residues at its C-terminus as compared to GLP-1. Mann et al. *Biochem. Soc. Trans.* 35:713-716, 2007 and Runge et al., *Biochemistry* 46:5830-5840, 2007 describe a variety of GLP-1 and exendin-4 analogs which may be used in a conjugate of the present disclosure. The short half-life of GLP-1 results from enzymatic digestion by dipeptidyl peptidase IV (DPP-IV). In certain embodiments, the effects of endogenous GLP-1 may be enhanced by administration of a DPP-IV inhibitor (e.g., vildagliptin, sitagliptin, saxagliptin, linagliptin or alogliptin).

In various embodiments, a conjugate may include amylin or an amylin analog (i.e., a peptide with amylin like bioactivity that differs from amylin by 1-10 amino acid substitutions, additions or deletions and/or by a chemical modification). Amylin plays an important role in glucose regulation (e.g., see Edelman and Weyer, *Diabetes Technol. Ther.* 4:175-189, 2002). Amylin is a neuroendocrine hormone that is co-secreted with insulin by the beta cells of the pancreas in response to food intake. While insulin works to regulate glucose disappearance from the bloodstream, amylin works to help regulate glucose appearance in the bloodstream from the stomach and liver. Pramlintide acetate (SYMLIN®) is an exemplary amylin analog. Since native human amylin is amyloidogenic, the strategy for designing pramlintide involved substituting certain residues with those from rat amylin, which is not amyloidogenic. In particular, proline residues are known to be structure-breaking residues, so these were directly grafted from the rat sequence into the human sequence. Glu-10 was also substituted with an asparagine.

In various embodiments, a pre-conjugated drug may contain one or more reactive moieties (e.g., carboxyl or reactive ester, amine, hydroxyl, aldehyde, sulfhydryl, maleimidyl, alkynyl, azido, etc. moieties). As discussed below, these reactive moieties may, in certain embodiments, facilitate the conjugation process. Specific examples include peptidic drugs bearing alpha-terminal amine and/or epsilon-amine lysine groups. It will be appreciated that any of these reactive moieties may be artificially added to a known drug if not already present. For example, in the case of peptidic drugs a suitable amino acid (e.g., a lysine) may be added or substituted into the amino acid sequence. In addition, as discussed in more detail below, it will be appreciated that the conjugation process may be controlled by selectively blocking certain reactive moieties prior to conjugation.

As discussed above, the present disclosure is not limited to any particular combination of drug and exogenous target molecule.

Conjugate Framework

Conjugates can be prepared from frameworks that naturally include affinity ligands (e.g., polysaccharides such as glycogen and dextran naturally include glucose affinity ligands) and/or by artificially incorporating affinity ligands into a natural or synthetic framework. It is to be understood that the conjugates of the present disclosure are not limited to a particular framework.

For example, conjugates may be prepared using frameworks that include polymeric and/or non-polymeric structures. It is also to be understood that the conjugate frameworks may be linear, branched, hyperbranched and/or a combination of these. The following section describes some exemplary conjugate frameworks.

In various embodiments, a conjugate may be prepared from a framework that includes a polymeric structure. For example, a polymer with pendant reactive groups (e.g., carboxyl or reactive ester, amine, hydroxyl, aldehyde, sulfhydryl, maleimidyl, alkynyl, azido, etc.) may be employed. It will be appreciated that different pendant groups may be mixed in a single framework (e.g., by co-polymerizing appropriate monomers in desired ratios to produce a polymeric framework). As discussed below, these reactive groups may be used to attach affinity ligands and/or drugs to the framework. Co-polymers, mixtures, and adducts of different frameworks may also be used. Such combinations may be useful for optimizing the mechanical and chemical properties of a material.

In various embodiments, frameworks having carboxyl (or reactive ester) pendant groups (—COOH bearing frameworks, or CBFs) may be used. Such frameworks may naturally include carboxyl groups or may be modified to include them. Exemplary polymeric CBFs include but are not limited to carboxylated polysaccharides (CPS) such as alginate (Ag), carboxymethylated-D-manno-D-glucan (CMMG, available from Daiichi Pharmaceutical Co.), carboxymethyldextran (CMDex), carboxymethylchitin (CMCh, available from Katakura Chikkalin Co.), N-desulfated N-acetylated heparin (DSH), and hyaluronic acid (HA). DSH and CMDex may be synthesized according to Sugahara, et al., Biol. Pharm. Bull., 24, 535-543 (2001). In general, hydroxylated frameworks may be carboxylated through reaction with chloroacetic acid under basic conditions. In the case of a polymeric framework the degree of carboxyl substitution with respect to monomer may vary between 1 and 100 mol %. Naturally occurring carboxylated polymers include but are not limited to carboxylated poly(amino acids) (CPAA) such as poly-L-glutamate and poly-L-aspartate. The carboxylate content may be varied between 1 and 100% mol COOH/mol AA residue by copolymerizing carboxylated amino acids (e.g., amino acids with a carboxyl group in addition to the carboxyl group which becomes part of the polymer backbone) with non-carboxylated amino acids (e.g., amino acids whose only carboxyl group becomes part of the polymer backbone).

In various embodiments, frameworks having amine pendant groups (—NH$_2$ bearing frameworks, or NBFs) may be used. Such frameworks may be naturally occurring or may be chemically modified to include a primary amine. The latter include but are not limited to polymeric frameworks, e.g., amine pendant polysaccharides (NPS) such as deacetylated chitosan (Ch) (Sigma Aldrich, Milwaukee, Wis.) and diethylaminoethyl ether dextran (DEAEDex), MW 500,000 g/mol (Polysciences, Warrington, Pa.). In the case of such polymeric frameworks the degree of amine substitution with respect to monomer may vary between 1 and 100 mol %. Other suitable NBFs include, but are not limited to, polynucleotides where one or more of the purine bases has been derivatized with an amine group at the 2' location. Naturally occurring aminated polymers include but are not limited to poly(amino acids) such as poly-L-lysine (PLL) and its enantiomer. The amine content may be varied between 1 and 100% mol NH$_2$/mol amino acid residue by copolymerizing an aminated amino acid (e.g., an amino acid with an amine in addition to the amine group that eventually becomes part of the polymer backbone) with non-aminated amino acids (e.g., an amino acid whose only amine is that which eventually becomes part of the polymer backbone).

In various embodiments, polymers having hydroxyl pendant groups (—OH bearing frameworks, or OBFs) may be used. Such frameworks may be naturally hydroxylated or may be chemically modified to include a hydroxyl group. In addition to dextran, naturally occurring polymeric OBFs include but are not limited to polysaccharides such as yeast mannan (Mn), pullulan (Pl), amylose (Am), amylopectin (AmP), glycogen (Gl), cellulose (Cl), hyaluronate (Hy), chondroitin (ChD), and dextrin (Dx), all of which may be obtained commercially from Sigma Aldrich. In addition, poly (amino acids) such as poly(serine), poly(threonine), poly(tyrosine), and poly(4-hydroxyproline) may also be employed as hydroxylated polymers. The hydroxyl content of the poly (amino acids) may be varied between 1 and 100% mol —OH/mol amino acid residue by co-polymerizing hydroxylated amino acids with non-hydroxylated amino acids. Of course, carboxyl (or reactive ester), amino, and hydroxyl pendant groups may be mixed in a single polymer by co-polymerizing the appropriate amino acids in desired ratios.

In various embodiments, frameworks having sulfhydryl pendant groups (—SH bearing frameworks, or SBFs) may be used. SBFs may be naturally sulfhydrylated or may be chemically modified using standard organic chemistry techniques to include a sulfhydryl group. In other embodiments, frameworks having aldehyde, maleimidyl, alkynyl, azido, etc. pendant groups may be used.

In addition to the aforementioned classes of frameworks, some exemplary polymers that may be used include poly (lactic acid) (PLA), poly(glycolic acid) (PGA), PLA-PGA co-polymers (PLGA), poly(anhydrides), poly(hydroxy acids), poly(ortho esters), poly(propylfumerates), poly(caprolactones), polyamides, polyacetals, biodegradable polycyanoacrylates and biodegradable polyurethanes.

In various embodiments, conjugates of the following general formula (I) may be employed:

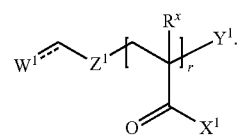

I

Various embodiments of the conjugates of formula (I) are described in more detail in Example 9; however, in general it is to be understood that:

$R^x$ is hydrogen or optionally substituted $C_{1-6}$ alkyl;

$Z^1$ is an optionally substituted bivalent $C_{1-10}$ hydrocarbon chain, wherein 1, 2, 3, 4 or 5 methylene units of $Z^1$ are optionally and independently replaced with one or more groups selected from —S—, —O—, —NR$^a$—, —(C=NR$^a$)—, —(C=O)—, —(S=O)—, —S(=O)$_2$—, —(CR$^b$=CR$^b$)—, —(N=N)—, an optionally substituted arylene moiety or an optionally substituted heteroarylene moiety, wherein R$^a$ is hydrogen, optionally substituted aliphatic, optionally substituted heteroaliphatic, optionally substituted aryl, optionally substituted heteroaryl, or a suitable amino protecting group; and R$^b$ is hydrogen, optionally substituted aliphatic, optionally substituted heteroaliphatic, optionally substituted aryl, or optionally substituted heteroaryl;

each occurrence of $X^1$ is independently —OR$^c$ or —N(R$^d$)$_2$, wherein R$^c$ is hydrogen, optionally substituted aliphatic, optionally substituted heteroaliphatic, optionally substituted aryl, optionally substituted heteroaryl, a suitable hydroxyl protecting group, a cation group, or an affinity ligand, and each R$^d$ is, independently, hydrogen, optionally substituted aliphatic, optionally substituted heteroaliphatic, optionally substituted aryl, optionally substituted heteroaryl, a suitable amino protecting group, or an affinity ligand, with the proviso that at least two occurrences of $X^1$ include an affinity ligand;

$Y^1$ is hydrogen, halogen, optionally substituted aliphatic, optionally substituted heteroaliphatic, optionally substituted aryl, optionally substituted heteroaryl, —OR$^e$ or —SR$^e$ wherein R$^e$ is hydrogen, optionally substituted aliphatic, optionally substituted heteroaliphatic, optionally substituted aryl, or optionally substituted heteroaryl;

r is an integer between 5-25, inclusive;
W$^1$ is a drug; and
----- corresponds to a single or double covalent bond.

In various embodiments, conjugates of the following general formula (II) may be employed:

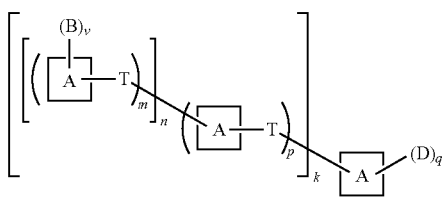

wherein:
each occurrence of

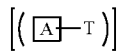

represents a potential branch within the conjugate;
each occurrence of

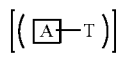

represents a potential repeat within a branch of the conjugate;
  each occurrence of [A] is independently a covalent bond, a carbon atom, a heteroatom, or an optionally substituted group selected from the group consisting of acyl, aliphatic, heteroaliphatic, aryl, heteroaryl, and heterocyclic;
  each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;
  each occurrence of R is independently hydrogen, a suitable protecting group, or an acyl moiety, arylalkyl moiety, aliphatic moiety, aryl moiety, heteroaryl moiety, or heteroaliphatic moiety;
  —B is -T-L$^B$-X;
  each occurrence of X is independently an affinity ligand;
  each occurrence of L$^B$ is independently a covalent bond or a group derived from the covalent conjugation of a T with an X;
  -D is -T-L$^D$-W;
  each occurrence of W is independently a drug;
  each occurrence of L$^D$ is independently a covalent bond or a group derived from the covalent conjugation of a T with a W;
  k is an integer from 2 to 11, inclusive, defining at least two k-branches within the conjugate;
  q is an integer from 1 to 4, inclusive;
  k+q is an integer from 3 to 12, inclusive;
  each occurrence of p is independently an integer from 1 to 5, inclusive; and
  each occurrence of n is independently an integer from 0 to 5, inclusive; and
  each occurrence of m is independently an integer from 1 to 5, inclusive; and
  each occurrence of v is independently an integer from 0 to 5, inclusive, with the proviso that within each k-branch at least one occurrence of n is ≥1 and at least one occurrence of v is ≥1.

It is to be understood that general formula (II) (and other formulas herein) does not expressly list every hydrogen. For example, if the central [A] is a $C_6$ aryl group and k+q<6 it will be appreciated that the open position(s) on the $C_6$ aryl ring include a hydrogen.

In general, it will be appreciated that each occurrence of [A] represents a potential branching node and that the number of branches at each node are determined by the values of k for the central [A] and n for non-central occurrences of [A]. Since k≥2 the conjugate will always include at least two k-branches. One of ordinary skill will appreciate that because each occurrence of n may be an integer from 0 to 5, the present disclosure contemplates both branched and hyperbranched (e.g., dendrimer-like) embodiments of these conjugates. The proviso which requires that within each k-branch at least one occurrence of n is ≥1 and at least one occurrence of v is ≥1 ensures that every conjugate includes at least two separate k-branches with an occurrence of B (i.e., an affinity ligand).

In certain embodiments, each occurrence of [A] in a p-bracketed moiety is substituted by a number of n-bracketed moieties corresponding to a value of n≥1. For example, when k=2 and p=2 in both k-branches, the conjugate may be of the formula (IIa):

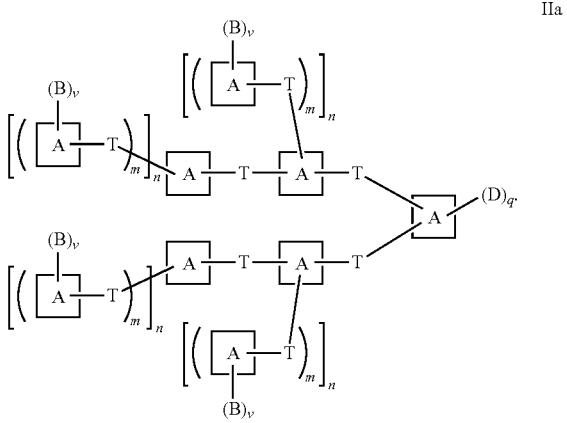

In other embodiments, only terminal occurrences of [A] in a p-bracketed moiety are substituted by a number of n-bracketed moieties corresponding to a value of n≥1. For example, when k=2 and p=2 in both k-branches (and n=0 for the first p-bracketed moiety in both k-branches), the conjugate may be of the formula (IIb):

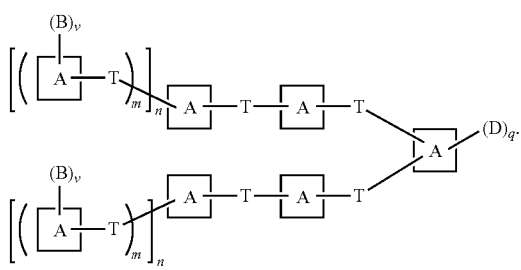

IIb

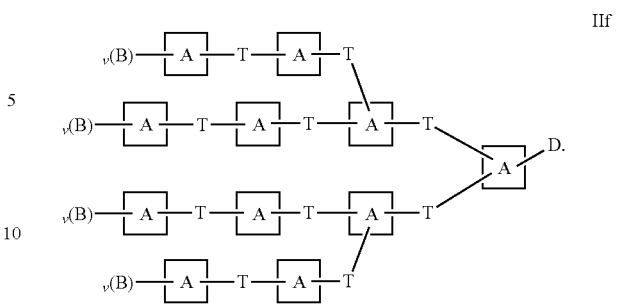

IIf

In certain embodiments, each occurrence of [A] in an m-bracketed moiety is substituted by a number of B moieties corresponding to the value of $v \geq 1$. For example, when $k=2$, each occurrence of $p=1$, and each occurrence of $m=2$, the conjugate may be of the formula (IIc):

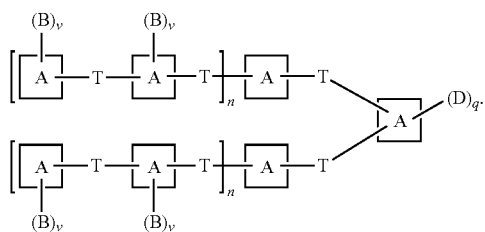

IIc

In other embodiments, only terminal occurrences of [A] in an m-bracketed moiety are substituted by a number of B moieties corresponding to a value of $v \geq 1$. For example, when $k=2$, each occurrence of $p=1$, and each occurrence of $m=2$ (and $v=0$ for the first m-bracketed moiety in each n-branch), the conjugate may be of the formula (IId):

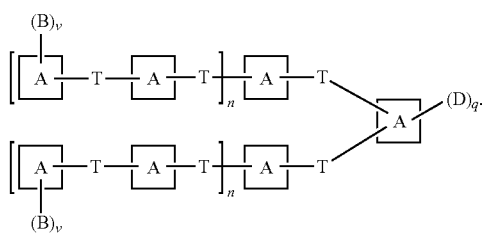

IId

By way of further example, when $q=1$ and $n=1$ in both k-branches of the previous formula, the conjugate may be of the formula (IIe):

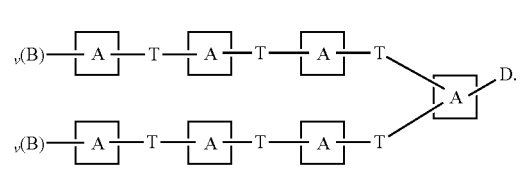

IIe

Alternatively, when $q=1$ and $n=2$ in both k-branches of the previous formula, the conjugate may be of the formula (IIf):

In various embodiments, the present disclosure also provides conjugates which include affinity ligands and/or a drug which are non-covalently bound the conjugate framework.

For example, in some embodiments, the present disclosure provides conjugates of any of the foregoing formulas, wherein:

each of [A], T, D, k, q, k+q, p, n, m and v is defined as described above and herein;

—B is -T-LRP$^B$—X;

each occurrence of X is independently an affinity ligand; and each occurrence of LRP$^B$ is independently a ligand-receptor pair which forms a non-covalent bond between T and X with a dissociation constant in human serum of less than 1 pmol/L.

In yet other embodiments, the present disclosure provides conjugates of any of the foregoing formulas, wherein:

each of [A], T, B, k, q, k+q, p, n, m and v is defined as described above and herein;

-D is -T-LRP$^D$—W; each occurrence of W is independently a drug; and each occurrence of LRP$^D$ is independently a ligand-receptor pair which forms a non-covalent bond between T and W with a dissociation constant in human serum of less than 1 pmol/L.

In other embodiments, the present disclosure provides conjugates of any of the foregoing formulas wherein:

each of [A], T, k, q, k+q, p, n, m and v is defined as described above and herein;

—B is -T-LRP$^B$—X;

each occurrence of X is independently an affinity ligand;

each occurrence of LRP$^B$ is independently a ligand-receptor pair which forms a non-covalent bond between T and X with a dissociation constant in human serum of less than 1 pmol/L.

-D is -T-LRP$^D$—W;

each occurrence of W is independently a drug; and each occurrence of LRP$^D$ is independently a ligand-receptor pair which forms a non-covalent bond between T and W with a dissociation constant in human serum of less than 1 pmol/L.

In various embodiments, a conjugate of the present disclosure may have the general formula (III):

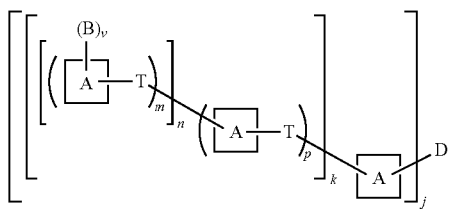

wherein [A], B, T, D, v, m, n, and p are as defined and described herein, k is an integer from 1 to 11, inclusive, and j is an integer from 2 to 4, inclusive. Conjugates of formula (III) may have multiple sites of conjugation of ligand to drug. It will be appreciated that, when q is 1, similar subgenera described to those described above (formulae (IIa) to (IIf)) can be contemplated by one skilled in the art for conjugates of formula (III) wherein j is 2, 3, or 4.

For purposes of exemplification and for the avoidance of confusion it is to be understood that an occurrence of: -[A]-D-[A]- in a conjugate of formula (III) (i.e., when j is 2) could be represented as: -[A]-T-L$^D$-W-L$^D$-T-[A]- (when the drug is covalently bound to the conjugate framework) or -[A]-T-LRP$^D$—W-LRP$^D$-T-[A]- (when the drug is non-covalently bound to the conjugate framework).

Description of Exemplary Groups

[A] (node)

In certain embodiments, each occurrence of [A] is independently an optionally substituted group selected from the group consisting of acyl, aliphatic, heteroaliphatic, aryl, heteroaryl, and heterocyclic. In some embodiments, each occurrence of [A] is the same. In some embodiments, the central [A] is different from all other occurrences of [A]. In certain embodiments, all occurrences of [A] are the same except for the central [A].

In some embodiments, [A] is an optionally substituted aryl or heteroaryl group. In some embodiments, [A] is 6-membered aryl. In certain embodiments, [A] is phenyl.

In certain embodiments, [A] is a heteroatom selected from N, O, or S. In some embodiments, [A] is nitrogen atom. In some embodiments, [A] is an oxygen atom. In some embodiments, [A] is sulfur atom. In some embodiments, [A] is a carbon atom.

T (Spacer)

In certain embodiments, each occurrence of T is independently a bivalent, straight or branched, saturated or unsaturated, optionally substituted $C_{1-20}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group. In certain embodiments, one, two, three, four, or five methylene units of T are optionally and independently replaced. In certain embodiments, T is constructed from a $C_{1-10}$, $C_{1-8}$, $C_{1-6}$, $C_{1-4}$, $C_{2-12}$, $C_{4-12}$, $C_{6-12}$, $C_{8-12}$, or $C_{10-12}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group. In some embodiments, one or more methylene units of T is replaced by a heterocyclic group. In some embodiments, one or more methylene units of T is replaced by a triazole moiety. In certain embodiments, one or more methylene units of T is replaced by —C(O)—. In certain embodiments, one or more methylene units of T is replaced by —C(O)N(R)—. In certain embodiments, one or more methylene units of T is replaced by —O—.

In some embodiments, T is

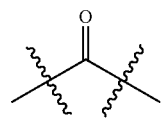

In some embodiments, T is

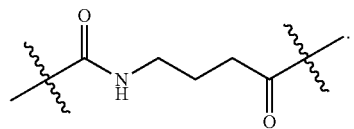 [SMILES: *C(=O)CCCNC(*)=O]

In some embodiments, T is

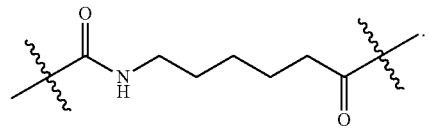 [SMILES: *C(=O)CCCCCNC(*)=O]

In some embodiments, T is

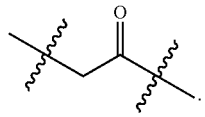 [SMILES: *CC(*)=O]

In some embodiments, T is

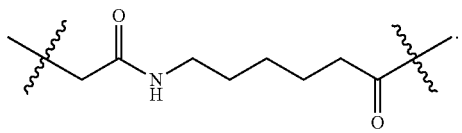 [SMILES: *CC(=O)NCCCCCC(*)=O]

In some embodiments, T is

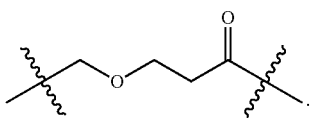 [SMILES: *COCCC(*)=O]

In certain embodiments, each occurrence of T is the same.
In certain embodiments, each occurrence of T (outside groups B and D) is a covalent bond and the conjugate is of the general formula (V) or (VI):

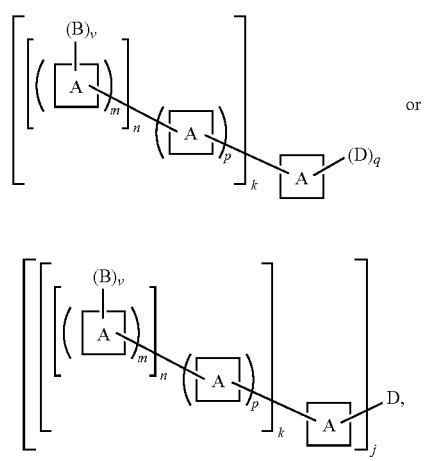

wherein $\boxed{A}$, B, D, v, m, n, p, k, and j are as defined and described for formula (II) or (III), respectively.

In certain embodiments of general formulae (V) and (VI), each occurrence of $\boxed{A}$ except for the central $\boxed{A}$ is a covalent bond, each occurrence of v=1, and the conjugate is of the formula (VII) or (VIII):

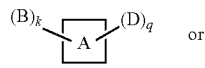

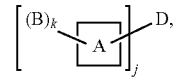

wherein $\boxed{A}$, B, D, q, k, and j are as defined and described for formula (II) or (III), respectively.

In certain such embodiments for formula (VII), k=2 and q=1.

In other embodiments, k=3 and q=1.

In other embodiments, k=2 and q=2.

In certain such embodiments for formula (VIII), k=1 and j=2.

In other embodiments, k=2 and j=2.

In other embodiments, k=3 and j=2.

In other embodiments, k=1 and j=3.

In other embodiments, k=2 and j=3.

In other embodiments, k=3 and j=3.

In some embodiments, the present disclosure provides conjugates of general formula (VIIa):

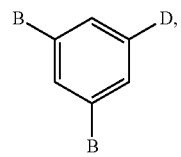

wherein B and D are as defined and described herein.

For example, in some embodiments, the present disclosure provides conjugates of formula:

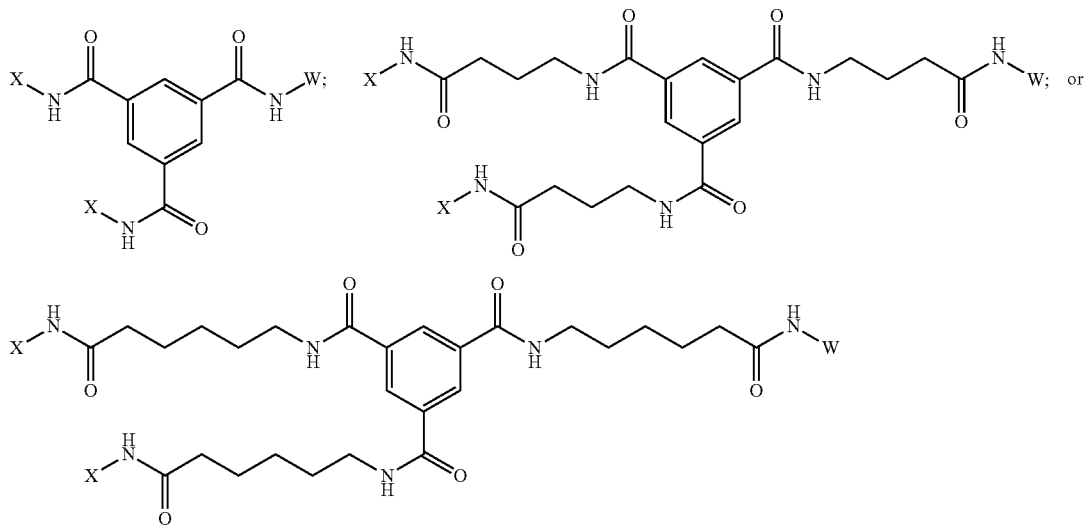

wherein W and X is as defined and described herein.

In some embodiments, the present disclosure provides conjugates of general formula (VIIb):

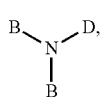

VIIb wherein B and D are as defined and described herein.

For example, in some embodiments, the present disclosure provides conjugates of formula:

In some embodiments, the present disclosure provides conjugates of general formula (VIIc):

VIIc wherein B and D are as defined and described herein.

For example, in some embodiments, the present disclosure provides conjugates of formula:

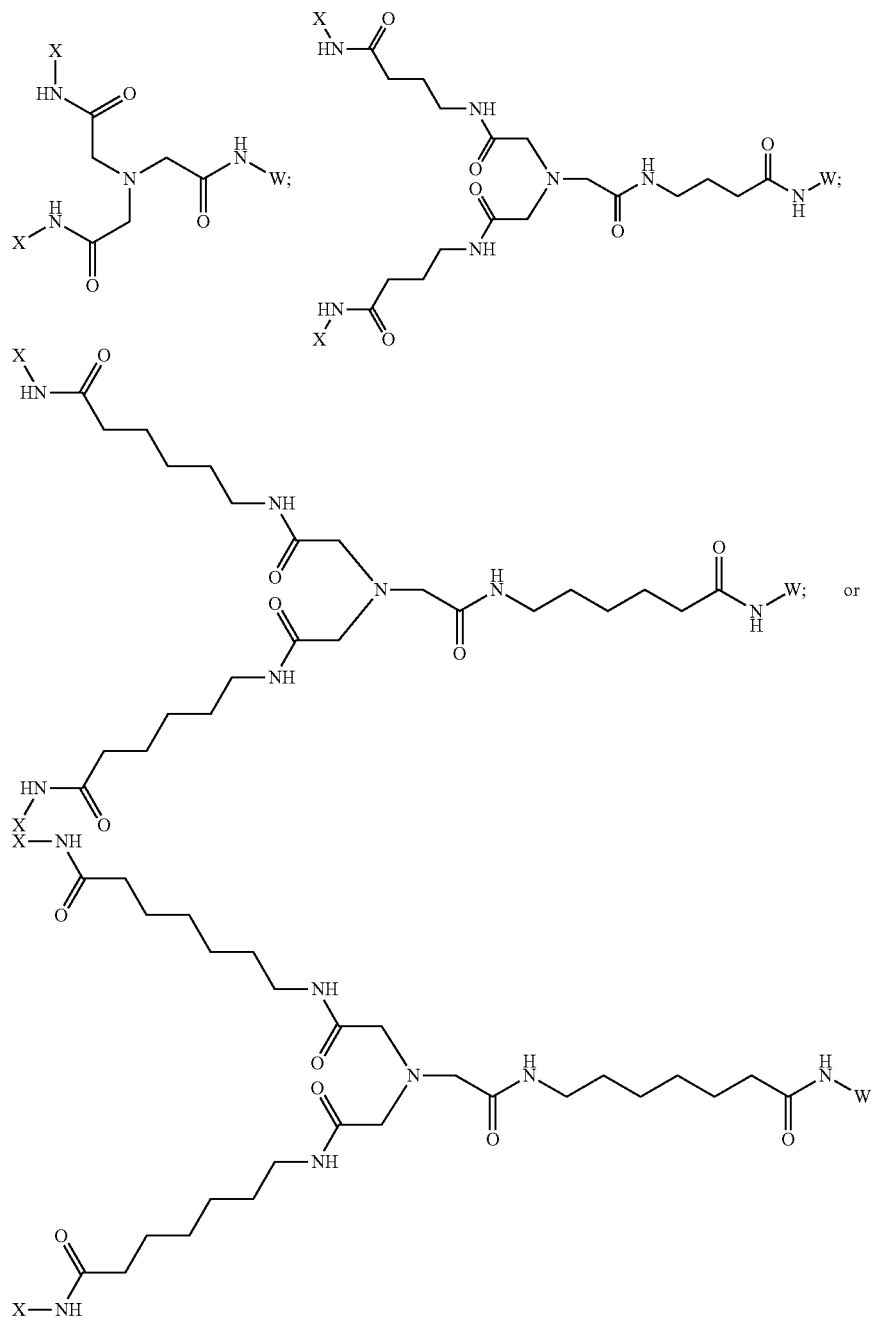

wherein W and X are as defined and described herein.

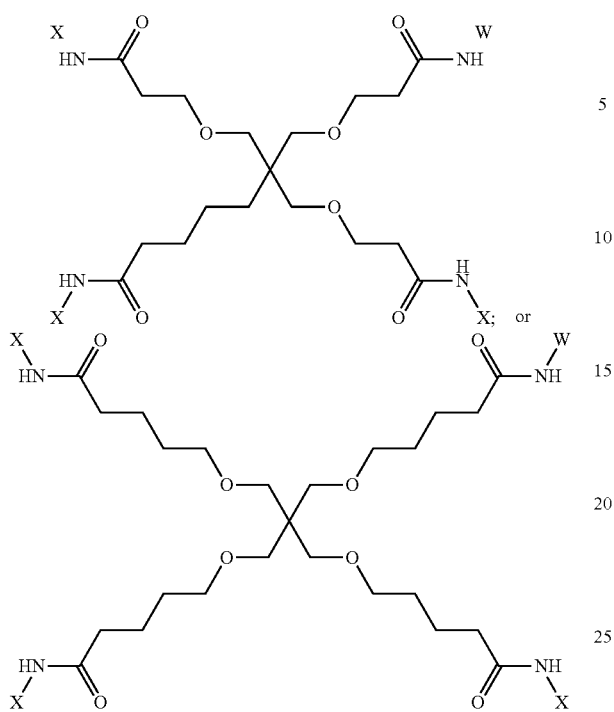

wherein W and X are as defined and described herein.

It will be appreciated that similar subgenera to those of formulae (VIIa), (VIIb), and (VIIc), and species thereof, can be contemplated by one skilled in the art for conjugates of formula (VIII) wherein j is 2, 3, or 4. For example, when j is 2, in certain embodiments, the present disclosure provides conjugates of formula:

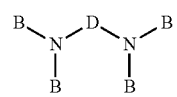

VIIIb-i

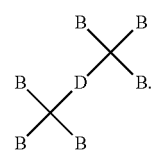

VIIIc-i wherein B and D are as defined and described herein.

In certain embodiments, the present disclosure provides conjugates of formula:

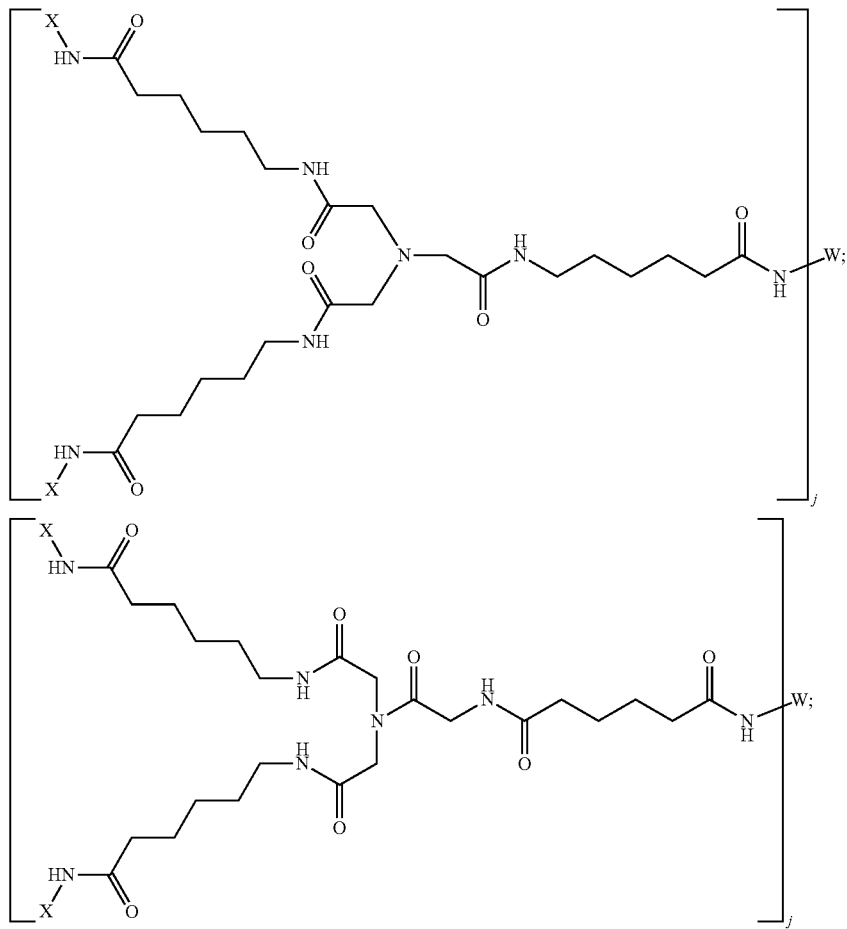

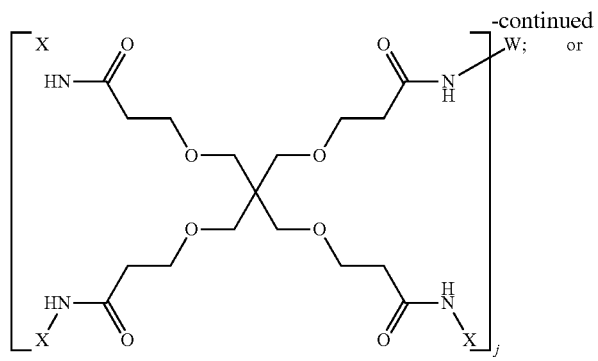
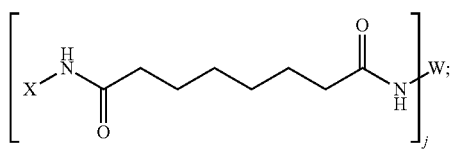

wherein W, X, and j are as defined and described herein.

B (Ligand)

In various embodiments, —B is -T-$L^B$-X where X is a ligand; and $L^B$ is a covalent bond or a group derived from the covalent conjugation of an X with a T. Exemplary ligands were described above.

D (Drug)

In various embodiments, -D is -T-$L^D$-W where W is a drug and $L^D$ is a covalent bond or a group derived from the covalent conjugation of a W with a T. Exemplary drugs were described above.

$L^B$ and $L^D$ (Covalent Conjugation)

One of ordinary skill will appreciate that a variety of conjugation chemistries may be used to covalently conjugate an X with a T and/or a W with a T (generally "components"). Such techniques are widely known in the art, and exemplary techniques are discussed below. Components can be directly bonded (i.e., with no intervening chemical groups) or indirectly bonded through a spacer (e.g., a coupling agent or covalent chain that provides some physical separation between the conjugated element and the remainder of the conjugate framework). It is to be understood that components may be covalently bound to a conjugate framework through any number of chemical bonds, including but not limited to amide, amine, ester, ether, thioether, isourea, imine, etc. bonds. In certain embodiments, $L^B$ and/or $L^D$ (generally "L" for the purposes of this section) is a covalent bond. In some embodiments, L is an optionally substituted moiety derived from conjugating an optionally substituted carbonyl-reactive, thiol-reactive, amine-reactive, or hydroxyl-reactive moiety of T with a carboxyl, thiol, amine, or hydroxyl group of X or W. In some embodiments, L is an optionally substituted moiety derived from conjugating an optionally substituted carboxyl-reactive, thiol-reactive, amine-reactive, or hydroxyl-reactive moiety of X or W with a carboxyl, thiol, amine, or hydroxyl group of T. In some embodiments, L is

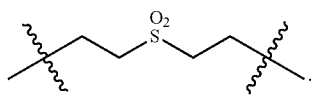 [SMILES: *CCS(=O)(=O)CC*]

In some embodiments, L is a succinimide moiety.

In various embodiments, components may be covalently bound to a conjugate framework using "click chemistry" reactions as is known in the art. These include, for example, cycloaddition reactions, nucleophilic ring-opening reactions, and additions to carbon-carbon multiple bonds (e.g., see Kolb and Sharpless, *Drug Discovery Today* 8:1128-1137, 2003 and references cited therein as well as Dondoni, *Chem. Asian J.* 2:700-708, 2007 and references cited therein). As discussed above, in various embodiments, the components may be bound to a conjugate framework via natural or chemically added pendant groups. In general, it will be appreciated that the first and second members of a pair of reactive groups (e.g., a carboxyl group and an amine group which react to produce an amide bond) can be present on either one of the component and framework (i.e., the relative location of the two members is irrelevant as long as they react to produce a conjugate). Exemplary linkages are discussed in more detail below. In various embodiments, carboxyl (or reactive ester) bearing components can be conjugated to —OH bearing frameworks (OBFs) using the procedure outlined by Kim et al., Biomaterials 24:4843-4851 (2003). Briefly, the OBF is dissolved in DMSO along with the carboxyl bearing component and reacted by means of N',N'-dicyclohexylcarbodiimide (DCC) and 4-dimethylaminopyridine (DMAP) as catalysts under a dry atmosphere. Carboxyl bearing components can be conjugated to —$NH_2$ bearing frameworks (NBFs) using a carbodiimide (EDAC) coupling procedure. Using this procedure, the carboxyl bearing component is functionalized by reaction with EDAC in a pH 5 buffer followed by the addition of the NBF. In either of these cases (and in any of the following cases), the resulting products may be purified by any number of means available to those skilled in the art including, but not limited to, size exclusion chromatography, reversed phase chromatography, silica gel chromatography, ion exchange chromatography, ultrafiltration, and selective precipitation.

In various embodiments, amine bearing components can be coupled to —COOH bearing frameworks (CBFs). CBFs using activated ester moieties (e.g., see Hermanson in *Bioconjugate Techniques*, 2$^{nd}$ edition, Academic Press, 2008 and references cited therein). Briefly, a CBF with terminal activated carboxylic acid esters such as —NHS, —SSC, —NPC, etc. is dissolved in an anhydrous organic solvent such as DMSO or DMF. The desired number of equivalents of amine bearing component are then added and mixed for several hours at room temperature. Amine bearing components can also be conjugated to CBFs to produce a stable amide bond as described by Baudys et al., *Bioconj. Chem.* 9:176-183, 1998. This reaction can be achieved by adding tributylamine (TBA) and isobutylchloroformate to a solution of the CBF and an amine bearing component in dimethylsulfoxide (DMSO) under anhydrous conditions. Amine bearing components can alternatively be coupled to OBFs through cyanalation using reagents including, but not limited to, cyanogen bromide (CNBr), N-cyanotriethylammonium tetrafluoroborate (CTEA), 1-Cyano-4-(Dimethylamino)-pyridinium tetrafluorborate (CDAP), and p-nitrophenylcyanate (pNPC). CNBr reactions can be carried out at mildly basic pH in aqueous solution. CDAP reactions are carried out in a mixture of DMSO and water at mildly basic pH using triethylamine (TEA) as a catalyst. In certain embodiments, amine bearing components can be conjugated to NBFs, e.g., through glutaraldehyde coupling in aqueous buffered solutions containing pyridine followed by quenching with glycine. In certain embodiments, amine bearing components can be conjugated to aldehyde bearing frameworks using a Schiff Base coupling procedure followed by reduction (e.g., see Hermanson in *Bioconjugate Techniques*, $2^{nd}$ edition, Academic Press, 2008 and references cited therein as well as Mei et al. in *Pharm. Res.* 16: 1680-1686, 1999 and references cited therein). Briefly, a framework with terminal activated aldehydes (e.g., acetaldehyde, propionaldehyde, butyraldehyde, etc.) is dissolved in an aqueous buffer with the pH at or below neutral to prevent unwanted aldehyde hydrolysis. The desired number of equivalents of an amine bearing component are then added and mixed at room temperature followed by addition of an excess of suitable reducing agent (e.g., sodium borohydride, sodium cyanobrohydride, sodium triacetoxyborohydride pyridine borane, triethylamine borane, etc.).

In various embodiments, hydroxyl bearing components can be conjugated to OBFs according to the divinylsulfone (DVS) procedure. Using this procedure, the OBF is added to a pH 11.4 bicarbonate buffer and activated with DVS followed by addition of a hydroxyl bearing component after which glycine is added to neutralize and quench the reaction. Hydroxyl bearing components may also be coupled to OBFs using activated ester moieties as described above to produce ester bonds.

In various embodiments, sulfhydryl bearing components can be coupled to maleimide bearing frameworks (MBFs) using a relatively mild procedure to produce thioether bonds (e.g., see Hermanson in *Bioconjugate Techniques*, $2^{nd}$ edition, Academic Press, 2008 and references cited therein). Because the maleimide group is much less susceptible to hydrolysis than activated esters, the reaction can be carried out under aqueous conditions. Briefly, an MBF is dissolved in a buffered aqueous solution at pH 6.5-7.5 followed by the desired number of equivalents of sulfhydryl bearing component. After mixing at room temperature for several hours, the thioether coupled conjugate may be purified. Sulfhydryl bearing components can also be conjugated to NBFs according to a method described by Thoma et al., *J. Am. Chem. Soc.* 121:5919-5929, 1999. This reaction involves suspending the NBF in anhydrous dimethylformamide (DMF) followed by the addition of 2,6-lutidine and acid anhydride and subsequent purification of the reactive intermediate. A sulfhydryl bearing component is then added to a solution of the intermediate in DMF with triethylamine. In various embodiments, azide bearing components can be coupled to an alkyne bearing framework (ABF) using the copper(I)-catalyzed modern version of the Huisgen-type azide-alkyne cycloaddition to give a 1,4-di-substituted 1,2,3-triazole (e.g., see Dondoni, *Chem. Asian J.* 2:700-708, 2007 and references cited therein as well as Dedola et al., *Org. Biomol. Chem.* 5: 1006-1017, 2007). This reaction, commonly referred to as a "click" reaction, may be carried out for example in neat THF using N,N-diisopropylethylamine and $Cu(PPh_3)_3Br$ as the catalyst system (e.g., see Wu et al., *Chem. Commun.* 5775-5777, 2005). The reaction may also be carried out in a 3:1 (THF: water) mixture using sodium ascorbate and $CuSO_4.5H_2O$ as the catalyst system (e.g., see Wu et al., supra). In either case, the azide bearing component is added to the ABF at the desired number of equivalents followed by mixing for 12-48 hours at room temperature. Alternatively, alkyne bearing components may be conjugated to an azide bearing framework using exactly the same conditions described above.

Certain components may naturally possess more than one of the same chemically reactive moiety. In some examples, it is possible to choose the chemical reaction type and conditions to selectively react the component at only one of those sites. For example, in the case where insulin is conjugated through reactive amines, in certain embodiments, the N-terminal α-Phe-B1 is a preferred site of attachment over the N-terminal α-Gly-A1 and ε-Lys-B29 to preserve insulin bioactivity (e.g., see Mei et al., *Pharm. Res.* 16: 1680-1686, 1999 and references cited therein as well as Tsai et al., *J. Pharm. Sci.* 86: 1264-1268, 1997). In an exemplary reaction between insulin with hexadecenal (an aldehyde-terminated molecule), researchers found that mixing the two components overnight in a 1.5M pH 6.8 sodium salicylate aqueous solution containing 54% isopropanol at a ratio of 1:6 (insulin:aldehyde mol/mol) in the presence of sodium cyanoborohydride resulted in over 80% conversion to the single-substituted Phe-B1 secondary amine-conjugated product (Mei et al., *Pharm. Res.* 16:1680-1686, 1999). Their studies showed that the choice of solvent, pH, and insulin:aldehyde ratio all affected the selectivity and yield of the reaction. In most cases, however, achieving selectivity through choice of chemical reaction conditions is difficult. Therefore, in certain embodiments it may be advantageous to selectively protect the component (e.g., insulin) at all sites other than the one desired for reaction followed by a deprotection step after the material has been reacted and purified. For example, there are numerous examples of selective protection of insulin amine groups available in the literature including those that may be deprotected under acidic (BOC), slightly acidic (citraconic anhydride), and basic (MSC) conditions (e.g., see Tsai et al., *J. Pharm. Sci.* 86: 1264-1268, 1997; Dixon et al., *Biochem. J.* 109: 312-314, 1968; and Schuettler et al., D. Brandenburg Hoppe Seyler's *Z. Physiol. Chem.* 360: 1721, 1979). In one example, the Gly-A1 and Lys-B29 amines may be selectively protected with tert-butoxycarbonyl (BOC) groups which are then removed after conjugation by incubation for one hour at 4 C in a 90% trifluoroacetic acid (TFA)/10% anisole solution. In one embodiment, a dry powder of insulin is dissolved in anhydrous DMSO followed by an excess of triethylamine. To this solution, approximately two equivalents of di-tert-butyl dicarbonate solution in THF is added slowly and the solution allowed to mix for 30-60 minutes. After reaction, the crude solution is poured in an excess of acetone followed by dropwise addition of dilute HCl to precipitate the reacted insulin. The precipitated material is centrifuged, washed with acetone and dried completely under vacuum. The desired di-BOC protected product may be separated from unreacted insulin, undesired di-BOC isomers, and mono-BOC and tri-BOC byproducts using preparative reverse phase HPLC or ion exchange chromatography (e.g., see Tsai et al., *J. Pharm. Sci.* 86: 1264-1268, 1997). In the case of reverse phase HPLC, a solution of the crude product in 70% water/30% acetonitrile containing 0.1% TFA is loaded onto a C8 column and eluted with an increasing acetonitrile gradient. The desired di-BOC peak is collected, rotovapped to remove acetonitrile, and lyophilized to obtain the pure product.

$LRP^B$ and $LRP^D$ (Non-Covalent Conjugation)

One of ordinary skill will appreciate that a variety of conjugation chemistries may be used to non-covalently conjugate an X with a T and/or W with a T (generally "components"). Such techniques are widely known in the art, and exemplary techniques are discussed below. In certain embodiments, the dissociation constant $(K_d)$ of the non-covalent linkage in human serum is less than 1 pmol/L. For example, a component may be non-covalently bound to a conjugate framework via a non-covalent ligand-receptor pair as is well known in the art (e.g., without limitation a biotin-avidin based pair). In such an embodiment, one member of the ligand receptor-pair is covalently bound to the component while the other member of the pair is covalently bound to the conjugate framework. When the component and conjugate framework are combined, the strong non-covalent interaction between the ligand and its receptor causes the component to become non-covalently bound to the conjugate framework. Typical ligand/receptor pairs include protein/co-factor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and further those described in Kessler pp. 105-152 of *Advances in Mutagenesis*" Ed. by Kessler, Springer-Verlag, 1990; "*Affinity Chromatography: Methods and Protocols (Methods in Molecular Biology)*" Ed. by Pascal Baillon, Humana Press, 2000; and "*Immobilized Affinity Ligand Techniques*" by Hermanson et al., Academic Press, 1992.

k and q

For conjugates of general formula (II), k is an integer from 2 to 11, inclusive, defining at least two k-branches within the conjugate. In certain embodiments, k=2 or 3. q is an integer from 1 to 4, inclusive, and defines the number of D groups which are bound to the central $\boxed{A}$ group. In certain embodiments, q=1. In some embodiments, q=2. k+q is an integer from 3 to 6, inclusive. In certain embodiments, k+q=3 or 4.

For conjugates of general formula (III), when j is 2, 3, or 4, k is an integer from 1 to 11, inclusive. In certain embodiments, k is 1, 2, or 3. q is an integer from 1 to 4, inclusive, and defines the number of D groups which are bound to the central $\boxed{A}$ group. In certain embodiments, q=1. In some embodiments, q=2. k+q is an integer from 3 to 6, inclusive. In certain embodiments, k+q=3 or 4.

p and m

Each occurrence of p is independently an integer from 1 to 5, inclusive. In certain embodiments, each occurrence of p is the same. In certain embodiments, p=1, 2 or 3. In certain embodiments, p=1.

Each occurrence of m is independently an integer from 1 to 5, inclusive. In certain embodiments, each occurrence of m is the same. In certain embodiments, m=1, 2 or 3. In certain embodiments, m=1.

n and v

Each occurrence of n is independently an integer from 0 to 5, inclusive, with the proviso that within each k-branch at least one occurrence of n is ≥1. Branches within a given k-branch are referred to herein as n-branches.

In certain embodiments, each occurrence of $\boxed{A}$ in a p-bracketed moiety is substituted by a number of n-bracketed moieties corresponding to a value of n≥1, e.g., see formula (IIa) above. In some such embodiments, each occurrence of n in the conjugate is the same. In some of these embodiments, n=1 or 2.

In other embodiments, only terminal occurrences of $\boxed{A}$ in a p-bracketed moiety are substituted by a number of n-bracketed moieties corresponding to a value of n≥1, e.g., see formula (IIb) above. In certain embodiments, each k-branch includes just one occurrence of n≥1 (i.e., all other occurrences of n=0). In some such embodiments, each occurrence of n in the conjugate is the same. In some of these embodiments, n=1 or 2.

Each occurrence of v is independently an integer from 0 to 5, inclusive, with the proviso that within each k-branch at least one occurrence of v is ≥1.

In certain embodiments, each occurrence of $\boxed{A}$ in an m-bracketed moiety is substituted by a number of B moieties corresponding to the value of v≥1, e.g., see formula (IIc) above. In some such embodiments, each occurrence of v in the conjugate is the same. In some of these embodiments, v=1 or 2.

In other embodiments, only terminal occurrences of $\boxed{A}$ in an m-bracketed moiety are substituted by a number of B moieties corresponding to a value of v≥1, e.g., see formula (IId) above. In certain embodiments, each k-branch includes just one occurrence of v≥1 (i.e., all other occurrences of v=0). In some such embodiments, each occurrence of v in the conjugate is the same. In some of these embodiments, v=1 or 2. In certain embodiments, each n-branch includes at least one occurrence of v≥1. In certain embodiment, each n-branch includes just one occurrence of v≥1 (i.e., all other occurrences of v=0). In some such embodiments, each occurrence of v in the conjugate is the same. In some of these embodiments, v=1 or 2.

j j of formula (II) is an integer from 1 to 4, inclusive, and defines the number of conjugations to the D group. In certain embodiments, j=1. In certain embodiments, j=2. In some embodiments, j=3. In other embodiments, j=4.

Drug Loading

In general, the amount of drug that is loaded onto a conjugate will depend on the molecular weight of the drug and can be controlled by adjusting the molecular weight of the conjugate framework and/or the level of chemical activation (i.e., when pendant groups are added to the framework). In various embodiments, the drug loading level may be in the range of 5 to 99% w/w of drug to conjugate (i.e., including drug). In various embodiments, loading levels within the narrower range of 50 to 99% may be used, e.g., in the range of 80 to 99%.

Other

In various embodiments, a biodegradable framework may be used. In various embodiments, a non-biodegradable framework may be used, e.g., when biodegradability is not relevant to the application and/or when the resulting framework or conjugate is sufficiently well excreted that biodegradability is not necessary. In various embodiments, the conjugate framework (or spacer when present, e.g., between a drug and framework) is susceptible to digestion by an enzyme. In various embodiments, the enzyme is present at the site of administration. One skilled in the art will recognize that a number of enzymes are present in patients that could cleave a conjugate framework. Without limitation, these include saccharidases, peptidases, and nucleases. Exemplary saccharidases include, but are not limited to, maltase, sucrase, amylase, glucosidase, glucoamylase, and dextranase. Exemplary peptidases include, but are not limited to, dipeptidyl peptidase-IV, prolyl endopeptidase, prolidase, leucine aminopeptidase, and glycyl glycine dipeptidase. Exemplary nucleases include, but are not limited to, deoxyribonuclease I, ribonuclease A, ribonucelase T1, and nuclease S1. One skilled in the art will also recognize that, depending on the choice of enzyme, there are a number of conjugate frameworks that are susceptible to enzymatic cleavage. For example, in cases where saccharidase degradation is desired, frameworks which include polysaccharides can be used (e.g., without limitation, a conjugate that includes a polysaccharide comprising repeating chains of 1,4-linked alpha-D-glucose residues will be degraded by alpha-amylases). Without limitation, suitable polysaccharides include glycogen and partially digested glycogen derived from any number of sources, including but not limited to, sweet corn, oyster, liver (human, bovine, rabbit, rat, horse), muscle (rabbit leg, rabbit abdominal, fish, rat), rabbit hair, slipper limpet, baker's yeast, and fungus. Other polysaccharide polymers and spacers that one could use include carboxylated polysaccharides, —$NH_2$ pendant polysaccharides, hydroxylated polysaccharides, alginate, collagen-glycosaminoglycan, collagen, mannan, amylose, amylopectin, cellulose, hyaluronate, chondroitin, dextrin, chitosan, etc. In cases where peptidase cleavage is desired, polypeptides that contain amino acid sequences recognized by the cleaving enzyme can be used (e.g., without limitation, a conjugate that includes a [-Glycine-Proline-] sequence will be degraded by prolidase). In certain embodiments one could use co-polymers of aminated and non-aminated amino acids, co-polymers of hydroxylated and non-hydroxylated amino acids, co-polymers of carboxylated and non-carboxylated amino acids, co-polymers of the above or adducts of the above. In cases where nuclease degradation is desired, polynucleotides can be used (e.g., without limitation, a conjugate that includes a polynucleotide containing an oligomer of sequential adenosine residues will be degraded by ribonuclease A).

In various embodiments, the pharmacokinetic and/or pharmacodynamic behavior of a conjugate (i.e., conjugated drug and/or drug which has been released from a conjugate by chemical or enzymatic degradation) may be substantially the same as the corresponding unconjugated drug (e.g., when both are administered subcutaneously). For example, from a pharmacokinetic (PK) perspective, the serum concentration curve may be substantially the same as when an equivalent amount of unconjugated drug is administered. Additionally or alternatively, the serum $T_{max}$, serum $C_{max}$, mean serum residence time (MRT), mean serum absorption time (MAT) and/or serum half-life may be substantially the same as when the unconjugated drug is administered. From a pharmacodynamic (PD) perspective, the conjugate may act on substances within the body in substantially the same way as the unconjugated drug. For example, in the case of an insulin conjugate, the conjugate may affect blood glucose levels in substantially the same way as unconjugated insulin. In this case, substantially similar pharmacodynamic behavior can be observed by comparing the time to reach minimum blood glucose concentration ($T_{nadir}$), the duration over which the blood glucose level remains below a certain percentage of the initial value (e.g., 70% of initial value or $T_{70\% \ BGL}$), etc. It will be appreciated that these PK and PD characteristics can be determined according to any of a variety of published pharmacokinetic and pharmacodynamic methods (e.g., see Baudys et al., *Bioconjugate Chem.* 9:176-183, 1998 for methods suitable for subcutaneous delivery).

In one embodiment, a conjugate (i.e., in isolated form without cross-linking agents) produces pharmacokinetic (PK) parameters such as time to reach maximum serum drug concentration ($T_{max}$), mean drug residence time (MRT), serum half-life, and mean drug absorption time (MAT) that are within 40% of those values determined for the unconjugated drug. In various embodiments, a conjugate produces PK parameters that are within 35%, 30%, 25%, 20%, 15% or even 10% of those produced by the unconjugated drug. In some embodiments, a conjugate produces PK parameters that are within 20% of those produce by the unconjugated drug. For example, in embodiments involving an insulin conjugate for subcutaneous delivery the conjugate may produce an insulin $T_{max}$ between 15-30 minutes, a mean insulin residence time (MRT) of less than 50 minutes, or a mean insulin absorption time (MAT) of less than 40 minutes, all of which are within 20% of those values determined from the human recombinant insulin treatment group. In certain embodiments, the conjugate may produce an insulin $T_{max}$ between 20-25 minutes, a mean insulin residence time (MRT) of less than 45 minutes, and a mean insulin absorption time (MAT) of less than 35 minutes. In certain embodiment, the conjugate may produce a serum half-life of less than 120 minutes, e.g., less than 100 minutes.

In one embodiment, an inventive conjugate produces pharmacodynamic (PD) parameters such as time to reach minimum/maximum blood concentration of a substance ($T_{nadir}/T_{max}$) or duration over which the blood level of the substance remains below/above 70%/130% of the initial value ($T_{70\% \ BL}/T_{130\% \ AL}$). For example, in embodiments involving an insulin conjugate for subcutaneous delivery the conjugate may produce a glucose $L_{nadir}$ between 45-60 minutes and a glucose $T_{70\% \ BGL}$ of less than 180 minutes, both of which are within 20% of those determined from the human recombinant insulin treatment group. In certain embodiments the conjugate may produce a glucose $T_{nadir}$ between 50-55 minutes and a glucose $T_{70\% \ BGL}$ of less than 160 minutes. In various embodiments, a conjugate produces PD parameters that are within 40%, 35%, 30%, 25%, 20%, 15% or even 10% of those produced by the unconjugated drug. In some embodiments, a conjugate produces PD parameters that are within 20% of those produce by the unconjugated drug.

Intermediates for Preparing Conjugates

In one aspect, the invention provides reagents for preparing conjugates of the present disclosure. Thus, in various embodiments, a compound of general formula (II) is provided wherein:

each of $\boxed{A}$, T, D, k, q, k+q, p, n, m and v is defined as described above and herein;
B is -T-$L^{B'}$; and
each occurrence of $L^{B'}$ is independently hydrogen, an alkyne-containing moiety, an azide-containing moiety, or an optionally substituted carbonyl-reactive, thiol-reactive, amine-reactive, or hydroxyl-reactive moiety.

In other embodiments, a compound of general formula (II) is provided wherein:

each of $\boxed{A}$, T, B, k, q, k+q, p, n, m and v is defined as described above and herein;
D is -T-$L^{D'}$; and
each occurrence of $L^{D'}$ is independently hydrogen, an alkyne-containing moiety, an azide-containing moiety, or an optionally substituted carbonyl-reactive, thiol-reactive, amine-reactive, or hydroxyl-reactive moiety.

Methods for Preparing Conjugates

We have exemplified methods for preparing the aforementioned conjugates using insulin as an exemplary drug and aminoethylglucose (AEG), aminoethylmannose (AEM), aminoethylbimannose (AEBM), and/or aminoethyltrimannose (AETM) as exemplary affinity ligands. Without limitation, conjugates with two affinity ligands and one drug molecule and with short distances between all framework components may be prepared using tris(hydroxymethyl)aminomethane (Tris), Tris-succinimidyl aminotriacetate (TSAT), tris-Succinimidyl-1,3,5-benzenetricarboxylate (TSB), and Benzene-1,3,5-tricarboxy-(N-4-butyric-NHS-ester)amide (TSB-C4) as conjugate frameworks. If more space between framework components is desired then Succinimidyl (6-aminocaproyl)aminotriacetate (TSAT-C6), Succinimidyl (6-amino(PEO-6))aminotriacetate (TSAT-PEO-6), Benzene-1,3,5-tricarboxy-(N-6-aminocaproic-NHS ester)amide (TSB-C6), and Benzene-1,3,5-tricarboxy-(N-10-aminodecanoic-NHS ester)amide (TSB-C10) may be used. The TSAT-C6 spacer arm chemistry imparts more hydrophobic character to the conjugate as compared to TSAT-PEO-6. For example, for purposes of illustration, in one embodiment, both the affinity ligand (e.g., AEG, AEM, AEMB and AETM) and insulin may be reacted to a TSAT-C6 framework through the terminal activated esters to produce insulin-TSAT-C6-AEG-2, insulin-TSAT-C6-AEM-2, insulin-TSAT-C6-AEMB-2, and insulin-TSAT-C6-AETM-2 conjugates. The various affinity ligands are synthesized ahead of time as discussed in the Examples. In addition, the A1 and B29 amino groups of insulin are BOC-protected as described in the Examples so that each insulin can only react at the Phe-B1 α-amino group. Approximately one equivalent of BOC-insulin as a 40-50 mg/ml solution in DMSO is added at room temperature to a 50 mg/ml solution of TSAT-C6 in DMSO containing excess triethylamine and allowed to react for approximately one hour. Next, an excess of AEG, AEM, AEBM, and/or AETM (2-10 equivalents) as a 100 mg/ml solution in DMSO is added and allowed to react for an additional 2 hours. After reaction, the DMSO solution is superdiluted by 10× into a pH 5 saline buffer after which the pH is adjusted to 8.0 and the solution passed through a Biogel P2 column to remove low molecular reactants and salts. The material eluting in the void fraction is concentrated using a 3K ultrafiltration apparatus after which it is injected on a prep scale reverse phase HPLC column (C8, acetonitrile/water mobile phase containing 0.1% TFA) to purify the desired product from unreacted BOC2-insulin. The desired elution peak is collected pooled and rotovapped to remove acetonitrile followed by lyophilization to obtain a dry powder. Finally, the BOC protecting groups are removed by dissolving the lyophilized powder in 90% TFA/10% anisole for one hour at 4 C followed by 10× superdilution in HEPES pH 8.2 buffer containing 0.150M NaCl. The pH is adjusted to between 7.0 and 8.0 using NaOH solution after which the material is passed through a Biogel P2 column to remove anisole, BOC, and any other contaminating salts. The deprotected, purified aqueous conjugate solution is then concentrated to the desired level and stored at 4 C until needed.

It will be appreciated that this exemplary procedure may be used to produce other conjugates with different affinity ligands and drugs, different conjugation chemistries, different separations between framework components, and/or different valencies by substituting the TSAT-C6 framework with a different framework as described below.

For example, if yet more distance is required between framework components and/or a preserved charge is required at the site of conjugation, then an appropriately-sized amine-bearing diethyl acetal (e.g., aminopropionaldehyde diethyl acetal (APDA) or aminobutyraldehyde diethyl acetal (ABDA)) may be conjugated to one of the reactive groups on the frameworks listed here followed by complete reaction of the remaining reactive groups with the affinity ligand of interest (e.g. AEM, AEBM, or AETM). A reactive aldehyde group can then be revealed from the diethyl acetal under acidic conditions followed by a reductive amination with insulin to complete the drug conjugation step then ABDA-TSAT, ABDA-LCTSAT, etc. may be employed. In yet another example, tetrakis-(N-succinimidyl carboxypropyl)pentaerythritol (TSPE), may be used to attach three affinity ligands and one drug molecule for increased multivalency. It will also be appreciated by those skilled in the art that any of the above teachings may be used to produce hyperbranched (e.g., dendrimer-like) conjugates with even higher order valencies. For example, Röckendorf and Lindhorst provide a comprehensive review of current approaches for producing hyperbranched structures in *Topics in Current Chemistry*. 217: 202-238, 2001. Furthermore, ligands already containing a predetermined degree of multivalency may again be reacted according to the procedures described above to produce even higher orders of ligand multiplicity. For example, a divalent AEM-2, AEBM-2, or AETM-2 molecule containing a terminal reactive amine may be prepared by conjugating two of each affinity ligand to a suitable framework to which a reactive amine is also conjugated. A trivalent AEM-3, AEBM-3, or AETM-3 molecule containing a terminal reactive amine may be prepared by conjugating three of each affinity ligand to a suitable framework to which a reactive amine is also conjugated. The $NH_2$-divalent sugars may be reacted with the same frameworks described above to produce drug conjugates with 4 and 6 ligands per drug molecule. The $NH_2$-trivalent sugars may be reacted with the same frameworks described above to produce drug conjugates with 6 and 9 ligands per drug molecule.

In all cases, it should be recognized that a mixture of different ligands may be conjugated to the same drug via a multivalent framework by adjusting the framework chemistry, valency, and the ligand:framework stoichiometry. For example, Insulin-AEM-1-AEBM-1, Insulin-AEBM-1-AETM-1, Insulin AEM-2-AETM-2, and Insulin AEM-1-AETM-2 may all be synthesized according to this mixed ligand method.

Finally, in some cases, it may be desirable to conjugate the affinity ligand to the framework through a different means than the drug. For example, a divalent maleimide/monovalent activate ester functionalized framework (e.g., succinimidyl-3,5-dimaleimidophenyl benzoate (SDMB)) may be used to conjugate two sulfhydryl functionalized affinity ligands and one amine-functionalized drug in separate steps. For example, insulin or another amine-containing drug may be conjugated to the activated ester portion of the framework using methods described herein. In a separate step, the aminoethylsugar (AEM, AEBM, AETM) may be converted to a terminal sulfhydryl-bearing ligand by reaction with 4-iminothiolane. Finally, the framework-di-maleimide-insulin conjugate may be mixed with an excess of sulfhydryl-functionalized sugar to produce the resulting divalent-sugar-insulin conjugate.

Multivalent Cross-Linking Agents

The conjugates of the present disclosure are combined with multivalent cross-linking agents to form cross-linked materials. The following sections describe exemplary cross-linking agents that can be used.

Figure 4:
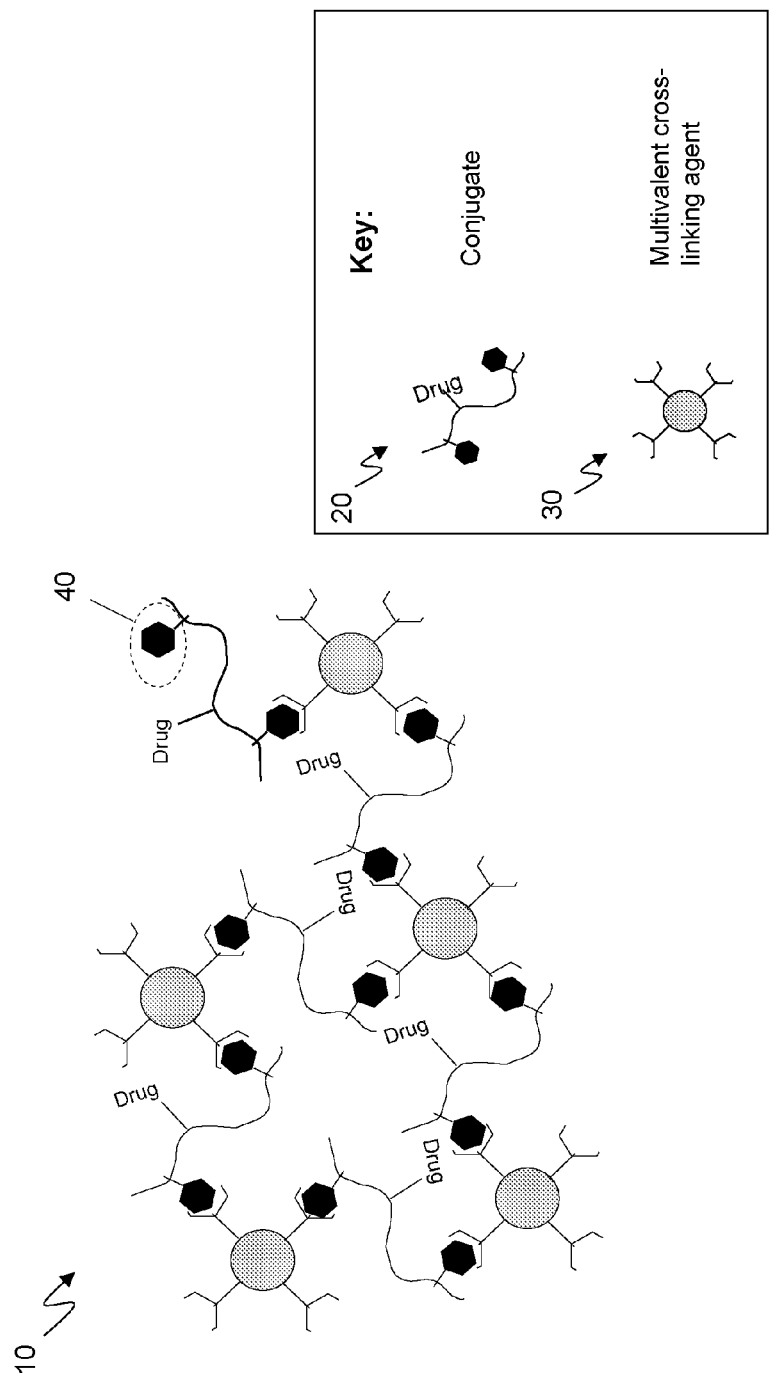
FIG. 4: is a schematic of a cross-linked material 10 which is capable of controllably releasing conjugates 20 in response to an exogenous target molecule. The materials are prepared by combining the conjugates 20 with multivalent cross-linking agents 30 that non-covalently bind the affinity ligands 40 of the conjugates 20 and thereby cross-link the conjugates 20 to form the cross-linked material 10. The non-covalent bonds between the multivalent cross-linking agents 30 and the affinity ligands 40 are competitively dissociated in the presence of excess amounts of the exogenous target molecule.

As discussed in more detail below and as illustrated in FIG. 4, the cross-linked material 10 is capable of controllably releasing the conjugates 20 in response to an exogenous target molecule. The materials are prepared by combining the conjugates 20 with multivalent cross-linking agents 30 that non-covalently bind the affinity ligands 40 of the conjugates 20 and thereby cross-link the conjugates 20 to form the cross-linked material 10. The non-covalent bonds between the multivalent cross-linking agents 30 and the affinity ligands 40 are competitively dissociated in the presence of excess amounts of the exogenous target molecule.

1. Polypeptide Cross-Linking Agents

In various embodiments, the multivalent cross-linking agents may include a polypeptide. As discussed in more detail below, suitable multivalent polypeptides exist in nature (e.g., various lectins) but can also be constructed by linking multiple monovalent binding proteins, e.g., monovalent lectins, peptide aptamers, antibodies, cell membrane receptors, etc. Still other multivalent polypeptides may be constructed by chemically linking binding fragments of these proteins.

A variety of mono- and multivalent ligand-binding proteins are available commercially (e.g., from Sigma-Aldrich), including a number of lectins, folate-binding protein, thyroxine-binding globulin, lactoferrin, etc. DeWolf and Best provide a review of ligand-binding proteins including biotin-binding proteins, lipid-binding proteins/transporters of hydrophobic molecules, bacterial periplasmic binding proteins, lectins, serum albumins, immunoglobulins, inactivated enzymes, odorant-binding proteins, immunosuppressant-binding proteins, and phosphate- and sulfate-binding proteins (see De Wolfe and Best, *Pharm. Rev.* 52: 207-236, 2000 and references cited therein). The cell membrane receptors for a variety of hormones have also been described in the art. In certain embodiments, mono- or multivalent binding proteins can be synthesized by rational computational design followed by site directed mutagenesis of existing ligand-binding proteins as described in Looger et al., *Nature* 423:185-190, 2003. Exemplary protein fragments include truncated MBP (Eda et al., *Biosci. Biotechnol. Biochem.*, 62:1326-1331, 1998), truncated conglutinin (Eda et al., *Biochem. J.* 316:43, 1996), truncated SP-D (Eda et al., *Biochem. J.* 323:393, 1997), and the glucose/galactose binding protein of *E. Coli* (Salins et al., *Analytical Biochemistry* 294:19-26, 2001).

a. Lectins

In certain embodiments, mono- or multivalent lectins may be included in a multivalent cross-linking agent. As discussed in more detail below, in certain embodiments, it may be advantageous to chemically modify the lectins. Lectins are particularly suitable for use in materials which are designed to respond to a saccharide (e.g., α-methyl-mannose). Lectins have been isolated from a variety of natural sources including seeds, roots, bark, fungi, bacteria, seaweed, sponges, mollusks, fish eggs, body fluids of invertebrates and lower vertebrates, and mammalian cell membranes (e.g., see *The Lectins: Properties, Functions, and Applications in Biology and Medicine*, Edited by Liener et al., Academic Press, 1986). A number of lectins have also been produced recombinantly (e.g., see Streicher and Sharon, *Methods Enzymol.* 363:47-77, 2003 and U.S. Patent Publication No. 20060247154). As noted above, lectins bind saccharides and polysaccharides with a high degree of specificity. For example, some lectins will bind only to mannose or glucose residues, while others only recognize galactose residues. Some lectins require that the particular residue be in a terminal position, while others bind to residues within a polysaccharide chain. Some lectins require specific anomeric structures and yet others recognize specific sugar sequences. The structures and properties of lectins have been extensively described in the literature. For recent reviews see Lectins, Edited by Sharon and L is, Kluwer Academic Publishers, 2003; *Handbook of Animal Lectins: Properties and Biomedical Applications*, Edited by Kilpatrick, Wiley, 2000; and Handbook of Plant Lectins: Properties and Biomedical Applications, Edited by Van Damme et al., Wiley, 1998. Exemplary lectins include calnexin, calreticulin, CD22, CD33, galectin (galactose-binding lectin), myelin-associated glycoprotein, N-acetylglucosamine receptor, selectin, sialoadhesin, aggrecan, asialoglycoprotein receptor, CD94, collectin (mannose-binding lectin), mannose receptor, versican, abrin, ricin, concanavalin A, phytohaemagglutinin, and pokeweed mitogen. In various embodiments, human analogs of plant lectins may be used. These include, without limitation, human mannan binding protein (MBP, also called mannan binding lectin, Sheriff et al., *Structural Biology*, 1:789-794 (1994); Dumestre-Perard et al., *Molecular Immunology*, 39:465-473 (2002)), human pulmonary surfactant protein A (SP-A, Allen, et al., *Infection and Immunity*, 67:4563-4569 (1999)), human pulmonary surfactant protein D (SP-D, Persson et al., *The Journal of Biological Chemistry*, 265:5755-5760 (1990)), CL-43 (a human serum protein), and conglutinin.

b. Peptide Aptamers

In certain embodiments monovalent peptide aptamers may be included in a multivalent cross-linking agent. As is well known in the art, peptide aptamers consist of a variable ligand-binding peptide loop fused within a protein scaffold (e.g., see Hoppe-Seyler and Butz, *J. Mol. Med.* 78:426-430, 2000 and Crawford et al., *Briefings in Functional Genomics and Proteomics* 2:72-79, 2003). The variable loop typically includes between about 10 and 20 amino acids. A variety of scaffold proteins may be used. In general, the site of insertion is chosen such that the peptide loop disrupts a region of the scaffold that would otherwise mediate some wild-type function, e.g., the bacterial protein thioredoxin-A in which the variable loop is inserted within the reducing active site (a -Cys-Gly-Pro-Cys- loop in the wild-type protein). Peptide aptamers with suitable affinity for the target molecule can be prepared and selected using any known method. For example, yeast two-hybrid libraries, yeast expression libraries, bacterial expression libraries and/or retroviral libraries for expression in mammalian cells may be used.

In various embodiments, peptide aptamers may be selected by affinity chromatography. According to such embodiments, peptide aptamers in a library are exposed to the target molecule and those that do not bind the target are removed. The bound peptide aptamers are then eluted and cloned for subsequent rounds of selection. A new library is then generated from one or more of these peptide aptamers (e.g., the peptide aptamer with the highest affinity for the target molecule in the first round of selection) and the stringency of the elution conditions is increased or modified to identify peptide aptamers with the desired binding affinity and/or specificity. In various embodiments, the selection process may involve steps in which the stringency of the elution conditions are gradually increased in order to select peptide aptamers with high affinity for the target molecule. In various embodiments, the selection process may involve steps in which the elution conditions are modified (e.g., by using a different affinity column) in order to select peptide aptamers with desired specificity for the target molecule. In various embodiments the selection process may generate a collection of sublibraries (or "pools") each of which comprises peptide aptamers with similar affinities and/or specificities for the target molecule. In various embodiments the selection process may generate a single peptide aptamer sequence (or "monoclonal"). It will be appreciated that any of these peptide aptamer sequences may be cloned for future recombinant expression.

c. Generating Multivalent Cross-Linking Agents

Multivalent cross-linking agents can be generated by covalently or non-covalently linking two or more monovalent binding proteins into a single construct. Typically, two or more proteins (which may have the same or different sequences) may be linked directly to one another (e.g., via a coupling agent) or indirectly through a framework. In various embodiments 2, 3, 4, 5, 6, 7 or 8 or more proteins may be combined into a single construct. In various embodiments the 2, 3, 4, 5, 6, 7 or 8 or more proteins may have the same sequence. It will be appreciated that either one of these approaches may require the proteins to be chemically modified (e.g., to include pendant reactive groups) prior to coupling. It will also be appreciated that the multivalent cross-linking agents of the present disclosure are not limited to a particular coupling reaction or framework (e.g., they can be prepared using frameworks that include polymeric and/or non-polymeric structures). It will further be appreciated that the frameworks may be linear, branched, dendrimeric and/or a combination of these. Exemplary frameworks and coupling chemistries are described below in the context of the conjugates.

In various embodiments the monovalent binding proteins are covalently linked to each other or a framework. In such embodiments, the proteins can be directly linked (i.e., with no intervening chemical groups) or indirectly linked through a spacer (e.g., a coupling agent or covalent chain that provides some physical separation between the protein or between the proteins and framework). As discussed below in the context of the conjugates it is to be understood that proteins may be covalently linked to each other or a framework through any number of chemical linkages, including but not limited to amide, ester, ether, isourea, and imine bonds.

In various embodiments, two or more monovalent binding proteins can be non-covalently linked to each other or to a framework. In certain embodiments, the dissociation constant (KO of the non-covalent linkage in human serum is less than 1 pmol/L. For example, proteins may be non-covalently linked to each other or a framework via a non-covalent ligand-receptor pair as is well known in the art (e.g., without limitation a biotin-avidin based pair). In such an embodiment, one member of the ligand receptor-pair is covalently linked to one protein while the other member of the pair is covalently linked to the other protein or framework. When the proteins (or proteins and framework) are combined, the strong non-covalent interaction between the ligand and its receptor causes the proteins to become non-covalently linked to each other (or the framework). Typical ligand/receptor pairs include protein/cofactor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and further those described in Kessler pp. 105-152 of *Advances in Mutagenesis*" Ed. by Kessler, Springer-Verlag, 1990; "*Affinity Chromatography: Methods and Protocols (Methods in Molecular Biology)*" Ed. by Pascal Baillon, Humana Press, 2000; and "*Immobilized Affinity Ligand Techniques*" by Hermanson et al., Academic Press, 1992.

2. Polynucleotide Cross-Linking Agents

In various embodiments, the multivalent cross-linking agents may include a polynucleotide aptamer. The polynucleotide aptamers bind the target molecule and are multivalent (i.e., capable of binding more than one target molecule). In general, monovalent aptamers will first be generated based on their binding properties for the target molecule. As is well known in the art, aptamers to a variety of target molecules can be generated through a process of in vitro selection. See Ellington and Szostak (1990) Nature 346:818; Tuerk and Gold (1990) Science 249:505; and U.S. Pat. No. 5,582,981. See also the polynucleotide aptamers that are described in U.S. Provisional Application No. 61/162,092 filed Mar. 20, 2009 and corresponding PCT application filed Jan. 27, 2010, each of which is incorporated herein by reference.

Typically, the process begins with the synthesis of a library consisting of randomly generated polynucleotide sequences of fixed length flanked by constant 5' and 3' ends that serve as primers. In certain embodiments (e.g., when optimizing an aptamer) one might start with a sequence which is known to bind the target molecule and generate a library which includes a collection of polynucleotides which exhibit a limited range of changes from the starting sequence (e.g., a random set of single mutations). The sequences in the library are then exposed to the target molecule and those that do not bind the target are removed (e.g., by affinity chromatography). The bound sequences are then eluted and amplified (e.g., by cloning and subsequent transcription or by PCR) to prepare for subsequent rounds of selection in which the stringency of the elution conditions is increased or modified to identify sequences with the desired binding affinity and/or specificity. Jarosch et al. (2006) *Nucleic Acids Res.* 34:86 have described methods that allow the process to be performed without the constant primer regions.

In various embodiments, the selection process may involve steps in which the stringency of the elution conditions are gradually increased in order to select aptamers with high affinity for the target molecule.

In various embodiments, the selection process may involve steps in which the elution conditions are modified (e.g., by using a different affinity column) in order to select aptamers with desired specificity for the target molecule.

In various embodiments the selection process may generate a collection of sublibraries (or "pools") each of which comprises aptamers with similar affinities and/or specificities for the target molecule. In various embodiments the selection process may generate a single aptamer sequence (or "monoclonal"). In various embodiments the aptamers are DNA based. In various embodiments the aptamers are RNA based. In various embodiments the aptamers are mixed RNA/DNA aptamers.

Multivalent aptamers can be generated by covalently or non-covalently linking two or more of these monovalent aptamers into a single construct. An exemplary method is described in Example 4 below. Typically, two or more aptamers (which may have the same or different sequences) may be bound directly to one another (e.g., via a coupling agent) or indirectly through an independent framework. In various embodiments 2, 3, 4, 5, 6, 7 or 8 aptamers may be combined into a single construct. In various embodiments the 2, 3, 4, 5, 6, 7 or 8 aptamers may have the same sequence. It will be appreciated that either one of these approaches may require the aptamers to be chemically modified (e.g., to include pendant reactive groups) prior to coupling. It will also be appreciated that the aptamers of the present disclosure are not limited to a particular coupling reaction or framework (e.g., they can be prepared using frameworks that include polymeric and/or non-polymeric structures). It will further be appreciated that the frameworks may be linear, branched, hyperbranched and/or a combination of these. Exemplary frameworks and coupling chemistries are described below in the context of the conjugates.

In various embodiments the aptamers are covalently bound to each other or a framework. In such embodiments, the aptamers can be directly bound (i.e., with no intervening chemical groups) or indirectly bound through a spacer (e.g., a coupling agent or covalent chain that provides some physical separation between the aptamers or between the aptamers and framework). As discussed above in the context of the conjugates it is to be understood that aptamers may be covalently bound to each other or a framework through any number of chemical linkages, including but not limited to amide, ester, ether, isourea, and imine bonds.

In various embodiments, the two or more aptamers are non-covalently bound to each other or to a framework. In certain embodiments, the dissociation constant ($K_d$) of the non-covalent linkage in human serum is less than 1 pmol/L. For example, aptamers may be non-covalently bound to each other or a framework via a non-covalent ligand-receptor pair as is well known in the art (e.g., without limitation a biotin-avidin based pair). In such an embodiment, one member of the ligand receptor-pair is covalently bound to one aptamer while the other member of the pair is covalently bound to the other aptamer or framework. When the aptamers (or aptamers and framework) are combined, the strong non-covalent interaction between the ligand and its receptor causes the aptamers to become non-covalently bound to each other (or the framework). Typical ligand/receptor pairs include protein/co-factor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and further those described in Kessler pp. 105-152 of *Advances in Mutagenesis*" Ed. by Kessler, Springer-Verlag, 1990; "*Affinity Chromatography: Methods and Protocols (Methods in Molecular Biology)*" Ed. by Pascal Baillon, Humana Press, 2000; and "*Immobilized Affinity Ligand Techniques*" by Hermanson et al., Academic Press, 1992.

3. Chemical Modification of Cross-Linking Agents

In general, it is to be understood that any of the aforementioned multivalent cross-linking agents may be chemically modified, e.g., in order to mitigate undesirable properties.

i. Non-Specific Modifications

In US 2007-0110811 we described the benefits of pegylating lectins in order to reduce their in vivo mitogenicity. Thus, in certain embodiments, a multivalent cross-linking agent may be covalently modified with one or more compounds. Without limitation this might involve reaction with an activated pegylation (PEG) agent (e.g., without limitation N-hydroxysuccinimide activated PEG, succinimidyl ester of PEG propionic acid, succinimidyl ester of PEG butanoic acid, succinimidyl ester of PEG alpha-methylbutanoate, etc.), another water soluble but non-PEG-containing polymer such as poly(vinyl alcohol), a reagent that can be easily coupled to lysines, e.g., through the use of carbodiimide reagents, a perfluorinated compound, etc. The skilled artisan will readily recognize other suitable compounds, e.g., by referring to the comprehensive review that can be found in "*Chemical Reagents for Protein Modification*" by Lundblad, CRC Press, 3$^{rd}$ Edition, 2004.

In general, the compound(s) may be attached to a multivalent cross-linking agent (e.g., a mitogenic lectin) via any of a number of attachment methods known to those skilled in the art (e.g., via amine, carboxyl, hydroxyl or sulfhydryl groups). The potential covalent linkages are similarly diverse (e.g., including amide bonds, carbamate bonds, ester bonds, thio-ether bonds, ether bonds, disulfide bonds, etc.). In certain embodiments suitable reactive groups can be grafted onto a multivalent cross-linking agent (e.g., a mitogenic lectin) by introducing an appropriate amino acid by site-directed mutagenesis as is known in the art. For example, PEGs are conveniently attached through amino or carboxyl groups. Amino acid residues with free amino groups include lysine residues and N-terminal amino acid residues. Amino acid residues with free carboxyl groups include aspartic acid residues, glutamic acid residues and C-terminal amino acid residues. Sulfhydryl groups found in cysteine residues may also be used as a reactive group for attaching the PEGs (or other compounds). In preferred embodiments PEGs are covalently attached to an amino group, especially the free amino group found in lysine residues.

Numerous methods for directly attaching PEGs to proteins are described in Delgado et al., *Crit. Rev. Thera. Drug Carrier Sys.* 9:249-304, 1992; Francis et al., *Intern. J. of Hematol.* 68:1-18, 1998; U.S. Pat. No. 4,002,531; U.S. Pat. No. 5,349,052; WO 95/06058; and WO 98/32466. One such method uses tresylated monomethoxy poly(ethylene glycol) (MPEG), which is produced by reacting MPEG with tresyl-chloride ($ClSO_2CH_2CF_3$). Tresylated MPEG reacts with exposed amine groups on lectins. A skilled person will recognize that the invention is not limited to any specific pegylation agent (or compound) and will be able to identify other suitable compounds that are known in the art.

In certain embodiments PEGs (or other compounds) may be attached to a multivalent cross-linking agent via an intervening linker. For example, U.S. Pat. No. 5,612,460, discloses urethane linkers for connecting PEG to proteins. PEGs can be attached to a protein via a linker by reaction with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional PEG derivatives and reaction chemistries for attaching PEG to proteins are described in WO 98/32466 and other patents, e.g., those that are assigned to Shearwater of Huntsville, Ala.; Nektar Therapeutics of San Carlos, Calif.; and/or Enzon Pharmaceuticals of Bridgewater, N.J. Catalogues can be obtained from these commercial PEG suppliers that describe a range of suitable PEG compounds and chemistries (e.g., see the Nektar Advanced PEGylation CATALOG 2004).

In various embodiments, N-terminal alpha-amine and/or epsilon-amino lysine groups of polypeptide based cross-linking agents may be succinylated and/or acetylated to change the charge distribution as well as any tertiary and quaternary effects associated with such changes. For example, polypeptides may be succinylated by reaction in a saturated sodium acetate buffer with an excess of succinic anhydride. Acetylation may be performed using the same procedure but with acetic anhydride as the modifying agent. For example, when the protein is concanavalin A, both acetylation and succinylation not only increase the density of negative charge within the polypeptide but also forces it to assemble as dimers instead of tetramers at physiological pH (e.g., see Agrawal et al., *Biochemistry.* 7:4211-4218, 1968 and Gunther et al., *Proc. Natl. Acad. Sci.* (*USA*) 70:1012-1016, 1973). In addition, the in vivo safety profile of these resulting materials is greatly improved as a result.

ii. Binding-Site Modifications

In certain embodiments, it may be advantageous to use an alternative and more specific method for modifying the multivalent cross-linking agents. In particular, we have found that certain low molecular weight conjugates of the present disclosure do not form insoluble drug delivery systems when combined with highly pegylated lectins made using high molecular weight PEG reagents (>5 kDa). This poses a challenge since we have previously found that lower molecular weight PEGs (<5 kDa) are much less effective in reducing lectin mitogenicity. Without wishing to be limited to any particular theory, it may be that the larger PEG groups are capable of sterically preventing binding and network formation with smaller low-valency conjugates, but not larger high-valency conjugates. In view of this, we devised an alternative non-PEG based solution for improving the safety profile of lectin-based cross-linking agents. We achieved this by specifically targeting and modifying the sugar binding site of lectins. For example, by reacting a mannose ligand directly into the concanavalin A binding site and purifying the unreacted material by high affinity ligand chromatography, we have been able to synthesize cross-linking agents with safety profiles that rival those of the best pegylated lectins. Without wishing to be limited to any particular theory, the functional concept appears to be that cell surfaces have a defined sugar affinity, valency, and ligand density, whereas the conjugates can have all of these properties adjusted by design. Thus, while incorporation of mannose into the lectin binding site completely abolishes the cross-linking agents ability to bind and thereby agglutinate or stimulate cells, incorporation of a higher density of higher affinity ligands on the conjugates still allows gel formation. In certain embodiments, incorporation of a small degree of pegylation with low MW, discrete PEG chains may be used to stabilize the multivalent lectins in solution under a variety of extreme storage conditions, yielding manufacturable, safe, functional cross-linking agents which complement the newly engineered conjugates.

In general, binding-site modified lectins will include at least one covalently linked affinity ligand which is capable of associating with one of lectin binding sites. In various embodiments, the modified lectins may include just one covalently linked affinity ligand. In various embodiments, the lectins may include one covalently linked affinity ligand per binding site. Typically a multivalent lectin will include 2 or 4 binding sites (e.g., a dimer or tetramer of a monovalent lectin) but the present disclosure also encompasses lectins with 3, 5 or more binding sites. The present disclosure also encompasses lectins with more than one covalently linked affinity ligand per binding site. The present disclosure further encompasses materials which include a mixture of lectins that include different numbers of covalently linked affinity ligands and/or that include unmodified lectins.

Any affinity ligand can be used for this purpose as long as it can associate with a binding site of the lectin once covalently linked to the lectin. Typically an affinity ligand will include a recognition element which interacts with the lectin binding site and a reactive linker which enables the affinity ligand to become covalently attached to the lectin once the recognition element is bound within the binding site.

Recognition Element

Any recognition element that can compete for binding with the lectin's cognate ligand (e.g., glucose or mannose in the case of Con A) could be used in an affinity ligand of the present disclosure. In various embodiments, the recognition element includes a saccharide. In certain embodiments the saccharide is a natural saccharide (e.g., glucose, fructose, galactose, mannose, arabinose, ribose, xylose, etc.). In certain embodiments the saccharide is a modified saccharide (e.g., 2'-fluororibose, 2'-deoxyribose, hexose, etc.). In certain embodiments the recognition element is glucose, sucrose, maltose, mannose, derivatives of these (e.g., glucosamine, mannosamine, methylglucose, methylmannose, ethylglucose, ethylmannose, etc.) and/or higher order combinations of these (e.g., linear and/or branched bimannose, linear and/or branched trimannose, etc.).

Other exemplary saccharides will be recognized by those skilled in the art. In particular, it is to be understood that depending on the application any one of the saccharides that are described above in the context of the conjugate affinity ligands may be used (e.g., any one of the saccharides of formula IVa or IVb). In certain embodiments, the recognition element includes a monosaccharide. In certain embodiments, the recognition element includes a disaccharide. In certain embodiments, the recognition element includes a trisaccharide. In some embodiments, the recognition element includes a saccharide and one or more amine groups. In some embodiments, the recognition element is aminoethylglucose (AEG). In some embodiments, the recognition element is aminoethylmannose (AEM). In some embodiments, the recognition element is aminoethylbimannose (AEBM). In some embodiments, the recognition element is aminoethyltrimannose (AETM). In some embodiments, the recognition element is O-aminoethyl-N-acetylglucosamine (AEGA). In some embodiments, the recognition element is aminoethylfucose (AEF). In other embodiments, the recognition element is D-glucosamine (GA).

In various embodiments, the recognition element includes a polysaccharide, glycopeptide or glycolipid. In certain embodiments, the recognition element includes from 2-10 saccharide moieties, e.g., 2, 3, 4, 5, 6, 7, 8, 9 or 10 moieties. The terminal and/or internal residues of the polysaccharide, glycopeptide or glycolipid may be selected based on the saccharide specificity of the lectin in question (e.g., see Goldstein et al., *Biochem. Biophys. Acta* 317:500-504, 1973 and L is et al., *Ann. Rev. Biochem.* 55:35-67, 1986).

In various embodiments, the recognition element for a particular lectin/exogenous target molecule combination may be selected empirically. According to such embodiments one or more recognition elements are screened based on their relative binding affinities for the lectin as compared to the exogenous target molecule. In certain embodiments a library of saccharides and/or polysaccharides are screened in this manner. A suitable recognition element will exhibit a detectable level of competition with the exogenous target molecule but will not compete so strongly that it prevents all binding between the lectin and the exogenous target molecule. In certain embodiments, different recognition elements may be screened by testing the effect of different affinity ligands on relevant lectin properties (e.g., based on their ability to inhibit agglutination and/or their material set points as discussed in more detail below and in the Examples). In certain embodiments, the recognition element will be selected in view of the conjugate that the modified lectin is to be combined with (e.g., so that the conjugate is able to displace the recognition element from the binding site and thereby form a cross-linked material).

Reactive Linker

Affinity ligands may be covalently linked to a lectin in any manner. Most methods will involve allowing the recognition element of the ligand to associate with the lectin binding site and then causing the reactive linker to react with the lectin. In certain embodiments, the reactive linker may be attached to the recognition element at a position that does not substantially interfere with the binding properties of the recognition element. For example, when the recognition element is a saccharide or polysaccharide the linker may be attached to the C1, C2 or C6 position of a terminal saccharide. In certain embodiments, the linker may be attached to the C1 position. The C1 position is also referred to as the anomeric carbon and may be connected to the linker in the alpha or beta conformation. In certain embodiments, the linker is attached to the C1 position as the alpha anomer.

In certain embodiments, photoactivatable linkers may be used. For example, Beppu et al., *J. Biochem.* 78:1013-1019, 1975, described a method in which an arylazido linker was activated using ultraviolet light to form a covalent bond between concanavalin A and a sugar derivative within the binding site. Similar results were recorded by Fraser et al., *Proc. Natl. Acad. Sci.* (*USA*) 73:790-794, 1976 using succinylated concanavalin A. A similar procedure has also been employed using ricin and a photoactivatable derivative of galactose as described by Houston, *J. Biol. Chem.* 258:7208-7212, 1983. Photoactivatable derivatives of complex glycopeptide ligands having a higher affinity for lectins than saccharides and disaccharides have also been described by Baenziger et al., *J. Biol. Chem.* 257:4421-4425, 1982. These derivatives were made by covalently linking a photoactivatable group to the peptide portion of the glycopeptide ligand.

In general, any photoactivatable linker may be used such as an aryl, purine, pyrimidine, or alkyl azide, a diazo or diazirine group, a benzophenone, or a nitrobenzene. A more comprehensive list of potentially useful photoactivatable linkers may be found in Fleming, *Tetrahedron* 51:12479-12520, 1995 as well as Brunner, *Annu. Rev. Biochem.* 62:483-514, 1993 and Wong, S. S. "Chemistry of Protein Conjugation and Cross-Linking", (1993), CRC Press, New York, pp. 168-194.

In various embodiments, the photoactivatable linker may include a diazirine group. Photoactivation of diazirine groups with ultraviolet (UV) light creates reactive carbene intermediates that can form covalent bonds through addition reactions with any amino acid side chain or peptide backbone within range of the linker. Long wavelength UV-light (about 320-370 nm, preferably about 345 nm) is typically used to activate diazirines (e.g., see Suchanek et al., *Nat. Methods* 2:261-268, 2005).

In various embodiments, the photoactivatable linker may include an aryl azide group. When aryl azide groups are exposed to UV-light they form nitrene groups that can initiate addition reactions with double bonds, insertion into C—H and N—H sites, or subsequent ring expansion to react as a nucleophile with primary amines. The latter reaction path predominates when primary amines are present in the sample. Without limitation, long wavelength UV-light (about 320-370 nm, preferably about 366 nm) is thought to be most efficient for substituted aryl azides (e.g., with hydroxy or nitro groups) while shorter wavelengths are thought to be most efficient for unsubstituted aryl azides. Suitable UV-light sources are available commercially, e.g., from Pierce, Rockford, Ill.

For example, in various embodiments the affinity ligand may be of the general formula (IX): $R_e$-$L^1$ where $R_e$ is a recognition element and -$L^1$ is a reactive linker. In certain embodiments $R_e$ is a saccharide moiety. In certain embodiments $R_e$ is a glucose or mannose moiety which is covalently bonded to the linker at the C1 position.

In certain embodiments -$L^1$ may be of the general formula (Xa):

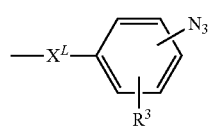

wherein:
$R^3$ is independently selected from the group consisting of hydrogen, —OH, —$NO_2$, and halogen (e.g., —F or —Cl);
$X^L$ is a covalent bond or a bivalent, straight or branched, saturated or unsaturated, optionally substituted $C_{1-20}$ hydrocarbon chain wherein one or more methylene units of $X^L$ are optionally and independently replaced by —O—, —S—, —N(R')—, —C(O)—, —C(O)O—, —OC(O)—, —N(R')C(O)—, —C(O)N(R')—, —S(O)—, —S(O)$_2$—, —N(R')SO$_2$—, —SO$_2$N(R')—, a heterocyclic group, an aryl group, or a heteroaryl group; and each occurrence of R' is independently hydrogen, a suitable protecting group, or an acyl moiety, arylalkyl moiety, aliphatic moiety, aryl moiety, heteroaryl moiety, or heteroaliphatic moiety.

In any case where a chemical variable is shown attached to a bond that crosses a bond of ring (for example as shown for $R^3$ above), this means that one or more such variables are optionally attached to the ring having the crossed bond. Each $R^3$ group on such a ring can be attached at any suitable position; this is generally understood to mean that the group is attached in place of a hydrogen atom on the parent ring. This includes the possibility that two $R^3$ groups can be attached to the same ring atom. Furthermore, when more than one $R^3$ group is present on a ring, each may be the same or different than other $R^3$ groups attached thereto, and each group is defined independently of other groups that may be attached elsewhere on the same molecule, even though they may be represented by the same identifier.

In certain embodiments, the —$N_3$ group is in the meta position. In certain embodiments, the —$N_3$ group is in the ortho position. In certain embodiments, the —$N_3$ group is in the para position.

In certain embodiments, one, two, three, four, or five methylene units of $X^L$ are optionally and independently replaced. In certain embodiments, $X^L$ is constructed from a $C_{1-10}$, $C_{1-8}$, $C_{1-6}$, $C_{1-4}$, $C_{2-12}$, $C_{4-12}$, $C_{6-12}$, $C_{8-12}$, or $C_{10-12}$ hydrocarbon chain wherein one or more methylene units of $X^L$ are optionally and independently replaced by —O—, —S—, —N(R')—, —C(O)—, —C(O)O—, —OC(O)—, —N(R')C(O)—, —C(O)N(R')—, —S(O)—, —S(O)$_2$—, —N(R')SO$_2$—, —SO$_2$N(R')—, a heterocyclic group, an aryl group, or a heteroaryl group. In some embodiments, one or more methylene units of $X^L$ is replaced by a heterocyclic group. In some embodiments, one or more methylene units of $X^L$ is replaced by a triazole moiety. In certain embodiments, one or more methylene units of $X^L$ is replaced by —C(O)—. In certain embodiments, one or more methylene units of $X^L$ is replaced by —C(O)N(R')—. In certain embodiments, one or more methylene units of $X^L$ is replaced by —O—.

In some embodiments, $X^L$ is

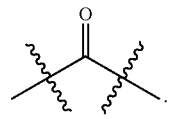 [SMILES: *C(*)=O]

In some embodiments, $X^L$ is

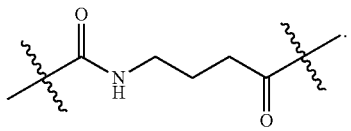 [SMILES: *C(=O)CCCNC(*)=O]

In some embodiments, $X^L$ is

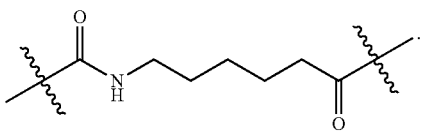 [SMILES: *C(=O)CCCCCNC(*)=O]

In some embodiments, $X^L$ is

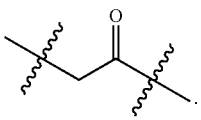 [SMILES: *CC(*)=O]

In some embodiments, $X^L$ is

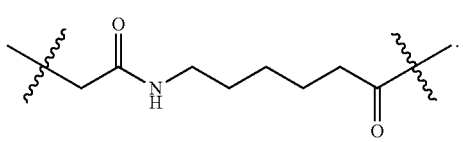 [SMILES: *CC(=O)NCCCCCC(*)=O]

In some embodiments, $X^L$ is

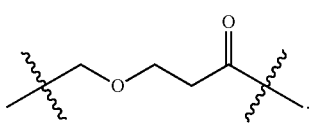 [SMILES: *COCCC(*)=O]

In certain embodiments $-L^1$ may be of the general formula (Xb):

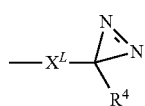

Xb where $X^L$ is as defined above for formula Xa; and
$R^4$ is hydrogen, $C_1$-$C_6$ alkyl or $-CF_3$.

In certain embodiments, non-photoactivatable linkers may be used. For example, U.S. Pat. Nos. 5,239,062 and 5,395,924 describe linkers that can be activated by changes in pH or temperature. Exemplary reactive linkers which are discussed include those which can be introduced into an affinity ligand using reagents such as cyanuric chloride (Kay et al., *Nature* 216:514-515, 1967) or dichloro-5-triazines such as 2-amino-4,6-dichloro-S-triazine (Kay et al., *Biochim. Biophys. Acta* 198:276-285, 1970) and 2,4-dichloro-6-methoxy-S-triazine (Lang et al., *J. Chem. Soc. Perkin* 1:2189-2194, 1977). Reactive linkers with NHS-esters or aldehydes that would react primarily with terminal amines such as those found on lysines could also be used.

In various embodiments, the reactive linker for a particular lectin/target molecule combination may be selected empirically. According to such embodiments several affinity ligands with the same recognition element and different linkers (e.g., linkers of different lengths, linkers with different reactive groups, linkers with different hydrophobicity, etc.) are screened based on their effect on relevant lectin properties (e.g., based on their ability to inhibit agglutination and/or their material set points as discussed in more detail below and in the Examples).

ii. Extent of Modification

In general, the number of compounds that are attached to each multivalent cross-linking agent (i.e., the degree of substitution) will vary based on the nature of the cross-linking agent, the nature of the compound(s), the number of reaction sites available and the reaction conditions. For example, the subunits of concanavalin A each include twelve lysine residues. As a result, if concanavalin A is pegylated with a compound that reacts with lysine residues, then each subunit could be covalently linked to 1, 2, 3, 4, 5, 6, 7, 8, 9, 10, 11 or 12 of these compounds. Conversely, each subunit of concanavalin A includes just one glucose binding site. Thus, if concanavalin A is reacted with a compound that reacts at the binding site, then each subunit will be covalently linked to just one such compound. Methods for determining the degree of substitution are discussed in Delgado et al., *Crit. Rev. Thera. Drug Carrier Sys.* 9:249-304, 1992.

In preferred embodiments, the chemical modification of a multivalent cross-linking agent may be optimized using a plurality of compounds and a plurality of reaction conditions (e.g., that vary the reagent concentrations, pH, temperature, etc.). Preferred compounds and reaction conditions are such that desirable properties (e.g., binding affinity) are not substantially impaired while undesirable properties (e.g., mitogenicity) are reduced as compared to an unmodified cross-linking agent. For example, an automated robotic handling device may be used to prepare a range of modified compositions with different compounds and different reaction conditions. Using routine orthogonal experimentation a skilled person can then screen the properties of the treated compositions. In certain embodiments further rounds of orthogonal optimization are performed around the preferred conditions to further refine the preferred compounds and reaction conditions.

In one embodiment, optimal reaction conditions are identified by separating treated compositions by electrophoresis, preferably by denaturing SDS-PAGE electrophoresis. In various embodiments, compositions which include uniformly modified cross-linking agents are preferred. These preferred compositions will have weaker bands at the molecular weight of the unmodified cross-linking agent as measured by SDS-PAGE.

4. Purification of Cross-Linking Agents

In various embodiments, multivalent cross-linking agents (whether they have been chemically modified or not) can be further processed in order to improve their properties. Thus, in certain embodiments, compositions comprising multivalent cross-linking agents can be purified in order to remove protein fragments, unmodified components, etc. In general, these separations can be achieved on the basis of physical properties (e.g., electrical charge; molecular weight; and/or size) and/or chemical properties (e.g., binding affinity for a target molecule). In certain embodiments optimal removal may be achieved by combining two or more methods that rely on these differential properties. In one embodiment, these separations are performed under denaturing conditions. For example, unmodified or partially modified cross-linking agents can be removed on the basis of their net charge by ion-exchange chromatography. Gel-filtration chromatography may be used to discriminate between differentially modified cross-linking agents on the basis of size. Affinity chromatography is another method that may be used to remove unmodified or partially modified cross-linking agents. This approach takes advantage of the differential binding affinity of modified, partially modified and unmodified cross-linking agents for a specific target molecule.

5. Characterization of Cross-Linking Agents

In various embodiments, multivalent cross-linking agents (whether they have been chemically modified or not) can be screened or further tested in order to confirm or characterize their properties. Representative assays include: affinity assays, agglutination assays, T-cell mitogenicity assays, T-cell viability assays, antigenicity assays, etc.

Affinity assays may involve passing the multivalent cross-linking agent over an affinity column (e.g., a resin with the target molecule) and determining the elution conditions required to remove the cross-linking agent from the column. Equilibrium dialysis can also be used as is known in the art. Set point assays in which the cross-linking agent is combined with one or more conjugates of the present disclosure and then contacted with varying concentrations of the target molecule may also be used. Preferably the binding affinity of a chemically modified cross-linking agents is at least 75% that of the unmodified cross-linking agent. More preferably the binding affinity is at least 85% and yet more preferably at least 95% that of the unmodified cross-linking agent.

In certain embodiments, an agglutination assay may be used to determine the minimum agglutinating concentration (MAC) of a multivalent cross-linking agent. For example, in certain embodiments the MAC may be determined using rabbit erythrocytes as described in US 20070110811. We have found that higher MAC values correlate strongly with reduced mitogenicity in the case of chemically modified lectins. In certain embodiments a modified cross-linking agent may have a MAC that is higher than the unmodified cross-linking agent. Preferably the MAC is 25 times that of the unmodified cross-linking agent. More preferably the MAC is 50 times and yet more preferably more than 100 times that of the unmodified cross-linking agent. In certain embodiments, the modified cross-linking agent exhibits a MAC with a 2% v/v suspension of formaldehyde-stabilized rabbit erythrocytes that is greater than 4 ug/ml. Preferably the MAC is greater than 6 ug/ml, more preferably greater than 10 ug/ml, even more preferably greater than 25 ug/ml.

Mitogenicity assays will typically involve contacting the compositions of interest with a T-cell culture (e.g., PBMC cells) for a period of time and then measuring the level of T-cell proliferation. Various methods for measuring cell proliferation are known. In one embodiment the cell density may be measured spectrophotometrically at 450 nm. In another embodiment an indirect measure can obtained by detecting the reduction of MTT at 570 nm (e.g., see Ohno et al., *J. Immunol. Methods* 145:199-203, 1991). In preferred embodiments, the level of cell proliferation is determined using a tritiated thymidine uptake assay. Those skilled in the art will recognize that other suitable methods may be used and that the invention is in no way limited to a specific proliferation assay. In certain embodiments, the T-cell mitogenicity of a modified cross-linking agent is less than 50% the T-cell mitogenicity of the unmodified cross-linking agent. The reduction in T-cell mitogenicity may be assessed by performing a comparative thymidine uptake assay across a range cross-linking agent concentrations, e.g., 0.01, 0.1, 1, 10, 100 and 1000 ug/ml. In preferred embodiments, the thymidine uptake assay is performed with samples that include approximately 500,000 PBMCs. The mitogenicity of the test composition (e.g., a modified composition) is then expressed as the % maximal unmodified mitogenicity. The % maximal unmodified mitogenicity is obtained by dividing the maximal CPM (counts per minute) value for the test composition over all measured concentrations by the maximal CPM value of the unmodified composition over all measured concentrations. Preferably, the test composition with reduced mitogenicity induces a level of T-cell proliferation that is at least 50% lower than the unmodified composition. More preferably, the level is at least 75% lower, even more preferably at least 90%, 95% or 99% lower.

T-cell viability can be measured using a similar experiment by adding Trypan Blue to the T-cell culture and counting a representative sample of the cells (noting those that either take up the trypan or still exclude the trypan, i.e., those that become blue vs. those that do not). The % viability is then calculated by dividing the number of cells that exclude the trypan (alive, "not blue") by the total number of cells counted (dead, "blue," plus live, "not blue"). Those skilled in the art will recognize that other suitable methods may be used and that the invention is in no way limited to a specific viability assay. In certain embodiments, a modified cross-linking agent exhibits a percentage cell viability at 100 ug/ml that is greater than 10% when assayed using PBMCs at a concentration of 500,000 cells/ml. Preferably the percentage cell viability is greater than 25%, more preferably greater than 50%, even more preferably greater than 90%.

Cross-Linked Materials

When cross-linking agents and conjugates are combined in the absence of the exogenous target molecule, a non-covalently cross-linked material is formed. In various embodiments, the material may be prepared in aqueous solution through self-assembly by mixing solutions of the cross-linking agent and conjugate. In various embodiments, particles of the material may be prepared by reverse emulsion. As described in more detail in US 2004/0202719, this can be achieved by adding the aforementioned aqueous solution to a mixture of a hydrophobic liquid and a surfactant and agitating the mixture.

Once formed, the cross-linked material can be used for a variety of applications. When the material is placed in the presence of free exogenous target molecules these compete for the interactions between the cross-linking agents and the conjugates. Above a certain concentration of free exogenous target molecule, the level of competition becomes such that the material begins to degrade by releasing conjugates from the surface. In various embodiments, the extent and/or rate of release increases as the concentration of exogenous target molecule increases. As a result, conjugates are released from the material in a manner which is directly tied to the local concentration of the exogenous target molecule.

In general, the release properties of the material will depend on the nature of the cross-linking agents, conjugates, exogenous target molecule and conditions (e.g., pH, temperature, nature and concentration of endogenous molecules that bind the cross-linking agent, etc.). If the affinity of the cross-linking agents for the conjugates is much greater than for the exogenous target molecule then the material will only release conjugates at high concentrations of exogenous target molecule. As the relative affinity of the cross-linking agents for the conjugates is decreased, release of conjugates from the material will occur at lower exogenous target molecule concentrations. The release properties of the material can also be adjusted by varying the relative amounts of cross-linking agent to conjugate. Higher ratios of cross-linking agent to conjugate will lead to materials that release conjugates at higher exogenous target molecule concentrations. Lower ratios of cross-linking agent to conjugate will lead to materials that release conjugates at lower exogenous target molecule concentrations. It will be appreciated that, depending on the application, these variables will enable one to produce materials which respond to a wide variety of exogenous target molecule concentrations.

In various embodiments, the cross-linked material is insoluble when placed in pH 7 HEPES buffered saline at 37 C (25 mM HEPES containing 150 mM NaCl). In various embodiments, the cross-linked material remains substantially insoluble when exogenous target molecule is added to the buffer up to a threshold concentration called the set point. Above the set point, the cross-linked material exhibits an increase in the extent and rate of release of conjugates. It will be appreciated that this transition may occur sharply or may occur gradually over a range of concentrations around the set point. In general, the desired set point and transition will depend on the nature of the exogenous target molecule and the intended application for the material. In particular, when the material is designed to respond to an increase in the level of a particular exogenous target molecule, the desired set point may be determined based on the PK profile of the exogenous target molecule (in particular the $C_{max}$). It is to be understood that the amount of exogenous target molecule present in a patient will depend on the route, dose and schedule of administration and further on the delivery means (e.g., immediate release, extended release, and/or delayed release formulations could be used for an orally delivered exogenous target molecule).

It will be appreciated that the desired set point for any exogenous target molecule can be readily determined for a variety of different applications. It will also be appreciated that the set point may need to be adjusted for certain patients (e.g., based on patient gender, patients with abnormally low or high levels of absorption of the exogenous target molecule, etc.) or applications (e.g., a drug delivery system designed to release on a more frequent basis may require a lower threshold concentration than a system designed to release less frequently).

It will be appreciated that a material having a desired set point may be generated via routine experimentation using the materials and methods described herein. For example, the same cross-linking agent and conjugate can be combined to produce a series of materials with a gradually increasing ratio of cross-linking agent to conjugate (w/w). These materials will cover a spectrum of set points. Once a lead material with a suitable set point has been identified the process can be repeated with a finer resolution to yield an optimized material. Alternatively (or additionally) the same conjugate can be combined with a plurality of different cross-linking agents that have gradually increasing affinities for the conjugate. This will yield a plurality of materials with a spectrum of set points that can be further refined (e.g., by varying the w/w ratio of cross-linking agent to conjugate). Alternatively one could initiate the process by combining the same cross-linking agent with a plurality of different conjugates. In various embodiments, the conjugates may have varying affinities for the cross-linking agent (e.g., as a result of including different affinity ligands). In various embodiments, the conjugates may include the same affinity ligands but have different molecular weights (e.g., as a result of different conjugate frameworks).

In various embodiments, the material remains substantially insoluble when placed at 37 C in normal human serum for six hours using USP dissolution test method II at 50 rpm. In various embodiments, less than 1, 2, 4, 6, 8, or 10% of the material dissolves when placed at 37 C in normal human serum for six hours using USP dissolution test method II at 50 rpm. In various embodiments, a material of the present disclosure may remain substantially insoluble when placed in pH 7 HEPES buffered saline containing 20, 30, 40, 50, 60, 70, 80, 90, 100, 150, 200, 250, 300, 350 or 400 mg/dL glucose at 37 C for six hours using USP dissolution test method II at 50 rpm. In various embodiments, less than 1, 2, 4, 6, 8, or 10% of the material dissolves when placed in pH 7 HEPES buffered saline with 20, 30, 40, 50, 60, 70, 80, 90, 100, 150, 200, 250, 300, 350 or 400 mg/dL glucose at 37 C for six hours using USP dissolution test method II at 50 rpm.

Uses

In another aspect, the present disclosure provides methods of using the materials. In general, the materials can be used to controllably release conjugates in response to an exogenous target molecule.

In various embodiments, a material may be used to controllably deliver a drug to a patient. The invention encompasses treating a disease or condition by administering a material of the present disclosure. Although the materials can be used to treat any patient (e.g., dogs, cats, cows, horses, sheep, pigs, mice, etc.), they are most preferably used in the treatment of humans. A material can be administered to a patient by any route. In general the most appropriate route of administration will depend upon a variety of factors including the nature of the disease or condition being treated, the nature of the drug, the nature of the exogenous target molecule, the condition of the patient, etc. In general, the present disclosure encompasses administration by oral, intravenous, intramuscular, intra-arterial, subcutaneous, intraventricular, transdermal, rectal, intravaginal, intraperitoneal, topical (as by powders, ointments, or drops), buccal, or as an oral or nasal spray or aerosol. General considerations in the formulation and manufacture of pharmaceutical compositions for these different routes may be found, for example, in *Remington's Pharmaceutical Sciences*, 19$^{th}$ ed., Mack Publishing Co., Easton, Pa., 1995.

In various embodiments, the material may be administered subcutaneously, e.g., by injection. The material can be dissolved in a carrier for ease of delivery. For example, the carrier can be an aqueous solution including, but not limited to, sterile water, saline or buffered saline. In general, a therapeutically effective amount of a drug in the form of a conjugate will be administered. By a "therapeutically effective amount" of a drug is meant a sufficient amount of the drug to treat (e.g., to ameliorate the symptoms of, delay progression of, prevent recurrence of, delay onset of, etc.) the disease or condition at a reasonable benefit/risk ratio, which involves a balancing of the efficacy and toxicity of the drug. In general, therapeutic efficacy and toxicity may be determined by standard pharmacological procedures in cell cultures or with experimental animals, e.g., by calculating the $ED_{50}$ (the dose that is therapeutically effective in 50% of the treated subjects) and the $LD_{50}$ (the dose that is lethal to 50% of treated subjects). The $ED_{50}/LD_{50}$ represents the therapeutic index of the drug. Although in general drugs having a large therapeutic index are preferred, as is well known in the art, a smaller therapeutic index may be acceptable in the case of a serious disease or condition, particularly in the absence of alternative therapeutic options. Ultimate selection of an appropriate range of doses for administration to humans is determined in the course of clinical trials.

In various embodiments, the drug is insulin and the average daily dose of insulin is in the range of 10 to 200 U, e.g., 25 to 100 U (where 1 Unit of insulin is ~0.04 mg). In certain embodiments, an amount of material with these insulin doses is administered on a daily basis. In certain embodiments, an amount of material with 5 to 10 times these insulin doses is administered on a weekly basis. In certain embodiments, an amount of material with 10 to 20 times these insulin doses is administered on a bi-weekly basis. In certain embodiments, an amount of material with 20 to 40 times these insulin doses is administered on a monthly basis. Those skilled in the art will be recognize that this same approach may be extrapolated to other approved drugs with known dose ranges, e.g., any of the approved insulin sensitizers and insulin secretagogues described herein.

It will be understood that the total daily usage of a drug for any given patient will be decided by the attending physician within the scope of sound medical judgment. The specific therapeutically effective amount for any particular patient will depend upon a variety of factors including the disease or condition being treated; the activity of the specific drug employed; the specific composition employed; the age, body weight, general health, sex and diet of the patient; the time of administration, route of administration and rate of excretion of the specific drug employed; the duration of the treatment; drugs used in combination or coincidental with the specific drug employed; and like factors well known in the medical arts. In various embodiments, a material of the present disclosure may be administered on more than one occasion. For example, the present disclosure specifically encompasses methods in which a material is administered by subcutaneous injection to a patient on a continuous schedule (e.g., once a day, once every two days, once a week, once every two weeks, once a month, etc.).

In certain embodiments, a material of the present disclosure may be used to treat hyperglycemia in a patient (e.g., a mammalian patient). In certain embodiments, the patient is diabetic. However, the present methods are not limited to treating diabetic patients. For example, in certain embodiments, a material may be used to treat hyperglycemia in a patient with an infection associated with impaired glycemic control. In certain embodiments, a material may be used to treat diabetes.

In various embodiments, a material of the present disclosure may be administered to a patient who is receiving at least one additional therapy. In various embodiments, the at least one additional therapy is intended to treat the same disease or disorder as the administered material. In various embodiments, the at least one additional therapy is intended to treat a side-effect of the primary drug. The two or more therapies may be administered within the same, overlapping or non-overlapping timeframes as long as there is a period when the patient is receiving a benefit from both therapies. The two or more therapies may be administered on the same or different schedules as long as there is a period when the patient is receiving a benefit from both therapies. The two or more therapies may be administered within the same or different formulations as long as there is a period when the patient is receiving a benefit from both therapies. In certain embodiments, a single material of the present disclosure may include more than one drug for treating the same disease or disorder. In certain embodiments, two or more separate materials of the present disclosure may be administered (as a mixture or separately) that include different drugs for treating the same disease or disorder. In certain embodiments, an unconjugated secondary drug may be included in a material of the present disclosure (i.e., a drug which is simply mixed with the components of the material and not covalently bound to the cross-linked material). For example, in certain embodiments, any of these approaches may be used to administer more than one anti-diabetic drug to a subject. Certain exemplary embodiments of this inventive approach are described in more detail below in the context of insulin-related therapies; however, it will be appreciated from the foregoing that other therapies will benefit from such combination approaches.

Insulin sensitizers (e.g., biguanides such as metformin, glitazones) act by increasing a patient's response to a given amount of insulin. A patient receiving an insulin sensitizer will therefore require a lower dose of an insulin-based material of the present disclosure than an otherwise identical patient would. Thus, in certain embodiments, a material comprising insulin conjugates may be administered to a patient who is also being treated with an insulin sensitizer. In various embodiments, the material of the present disclosure may be administered at up to 75% of the normal dose required in the absence of the insulin sensitizer. In various embodiments, up to 50, 40, 30 or 20% of the normal dose may be administered.

Insulin resistance is a disorder in which normal amounts of insulin are inadequate to produce a normal insulin response. For example, insulin-resistant patients may require high doses of insulin in order to overcome their resistance and provide a sufficient glucose-lowering effect. In these cases, insulin doses that would normally induce hypoglycemia in less resistant patients fail to even exert a glucose-lowering effect in highly resistant patients. Similarly, the materials of the present disclosure are only effective for this subclass of patients when they release high levels of insulin-conjugates in a suitable timeframe. In certain embodiments, the treatment of this subclass of patients may be facilitated by combining the two approaches. Thus in certain embodiments, a traditional insulin-based therapy is used to provide a baseline level of insulin and a material of the present invention is administered to provide a controlled supplement of insulin when needed by the patient. Thus, in certain embodiments, a material comprising insulin conjugates may be administered to a patient who is also being treated with insulin. In various embodiments, the insulin may be administered at up to 75% of the normal dose required in the absence of the material of the present disclosure. In various embodiments, up to 50, 40, 30 or 20% of the normal dose may be administered. It will be appreciated that this combination approach may also be used with insulin resistant patients who are receiving an insulin secretagogue (e.g., a sulfonylurea, GLP-1, exendin-4, etc.) and/or an insulin sensitizer (e.g., a biguanide such as metformin, a glitazone).

Once the material has been administered as described above it can be triggered by administration of a suitable exogenous target molecule. In certain embodiment, a triggering amount of the exogenous target molecule is administered. As used herein, a "trigerring amount" of exogenous target molecule is an amount sufficient to cause release of some amount of conjugate from the previously administered material. It is to be understood that any of the aforementioned methods of administration for the material apply equally to the exogenous target molecule. It is also be to be understood that the methods of administration for the material and exogenous target molecule may be the same or different. In various embodiments, the methods of administration are different (e.g., for purposes of illustration the material may be administered by subcutaneous injection on a weekly basis while the exogenous target molecule is administered orally on a daily basis). The oral administration of an exogenous target molecule is of particular value since it facilitates patient compliance. In general, it will be appreciated that the conjugate release profile from the material will be related to the PK profile of the exogenous target molecule. Thus, the conjugate release profile can be tailored by controlling the PK profile of the exogenous target molecule. As is well known in the art, the PK profile of the exogenous target molecule can be tailored based on the dose, route, frequency and formulation used. For example, if a short and intense release of conjugate is desired then an oral immediate release formulation might be used. In contrast, if a longer less intense release of conjugate is desired then an oral extended release formulation might be used instead. General considerations in the formulation and manufacture of immediate and extended release formulation may be found, for example, in *Remington's Pharmaceutical Sciences*, 19th ed., Mack Publishing Co., Easton, Pa., 1995. In general, it will be appreciated that the set point of the material will be below the $C_{max}$ of the exogenous target molecule formulation for conjugate release to occur. For example, in various embodiments, the set point may be less than 10, 20, 30, 40, 50, 60, 70, 80 or 90% of the $C_{max}$.

It will also be appreciated that the relative frequency of administration of a material of the present disclosure and an exogenous target molecule may be the same or different. In certain embodiments, the exogenous target molecule is administered more frequently than the material. For example, in certain embodiment, the material may be administered daily while the exogenous target molecule is administered more than once a day. In certain embodiment, the material may be administered twice weekly, weekly, biweekly or monthly while the exogenous target molecule is administered daily. In certain embodiments, the material is administered monthly and the exogenous target molecule is administered twice weekly, weekly, or biweekly.

Kits

In another aspect the present disclosure provides kits that include cross-linking agents and conjugates and other reagents for preparing a material. For example, a kit may include separate containers that include a plurality of conjugates and a plurality of cross-linking agents. When the conjugates and cross-linking agents of the kit are mixed a cross-linked material is formed. In various embodiments, the material is designed for subcutaneous delivery and the kit includes a syringe. In various embodiments, a kit may include a syringe which is pre-filled with a cross-linked material. The kit may also include instructions for mixing the conjugates and cross-linking agents to produce the cross-linked material. The kit may also include a formulation of the exogenous target molecule, e.g., an oral dosage form such as a capsule or tablet.

In yet another aspect, the present disclosure provides libraries of conjugates and/or cross-linking agents. These libraries may be particularly useful for generating materials with a desired set point. In various embodiments, a library may include a plurality of cross-linking agents which produce different set points with the same conjugate. In various embodiments, a library may further include one or more conjugates which form cross-linked materials with cross-linking agents in the library. When the library includes more than one such conjugate, the different conjugates may have different molecular weights, a different number of affinity ligands per conjugate molecule and/or different affinity ligands. In various embodiments, a library may include one or more of the conjugates that include more than one type of affinity ligand. In various embodiments, a library may include a plurality of conjugates which produce different set points with the same cross-linking agents. In various embodiments, a library may further include one or more cross-linking agents which form cross-linked materials with conjugates in the library.

EXAMPLES

Example 1

Synthesis of α-Methyl-Mannose Triggered Material

Figure 2:
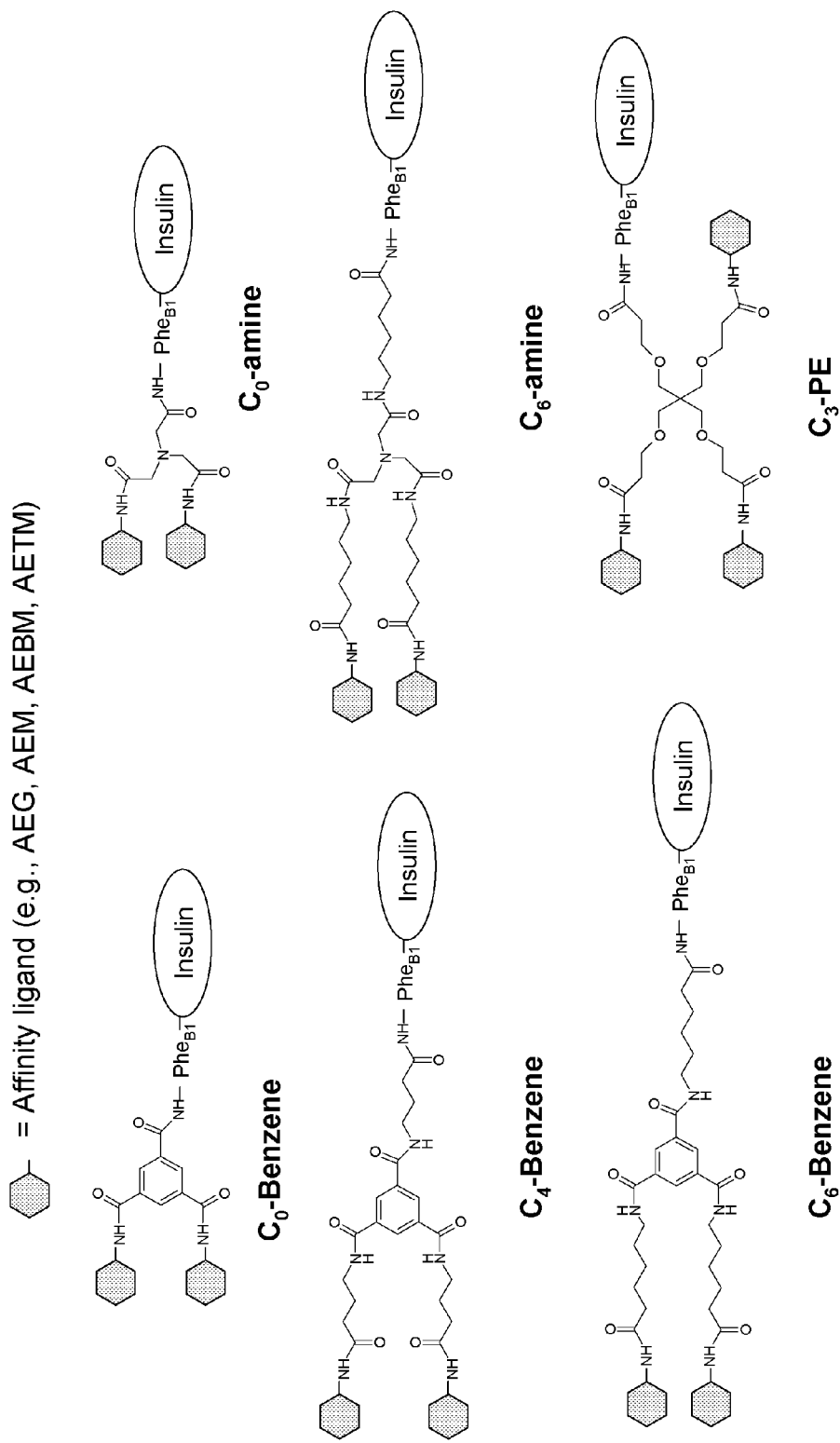
FIG. 2: shows the chemical structures of some exemplary conjugates including the TSB-C4 based conjugate used in the examples.

An exemplary conjugate was synthesized according to the method in Example 8 using TSB-C4 as the scaffold, AEBM as the affinity ligand, and $NH_2$-B1-BOC2(A1,B29)-insulin as the drug (see FIGS. 1-2 for affinity ligand and conjugate structure and Examples 3-7 for methods used to prepare these starting materials). 0.50 ml of a 2.3 mg/ml solution of conjugate in pH 8.2, 25 mM HEPES buffer containing 0.150 M sodium chloride (S14 buffer) was added to a centrifuge tube and subsequently mixed rapidly with 0.500 ml of a 18 mg/ml native Con A (NCA) solution in pH 7.4, 25 mM HEPES buffer containing 0.150 M sodium chloride (S24 buffer) to form a dispersion of insoluble particles. The dispersion was allowed to sit at room temperature for 20 min and then separated from the supernatant by centrifugation. The resulting cake was washed 5× with 1.0 ml of pH 7.4, 25 mM HEPES buffer containing 0.150 M sodium chloride (S24 buffer). After the last wash, the remaining insoluble material was incubated overnight at 37 C. The next day, the remaining particles were again isolated by centrifugation and washed one additional time in 1.0 ml of S24. The resulting insoluble material was dispersed in a total volume of 0.30 ml using S24 and set aside for future studies. This process may be scaled up directly to produce any amount of desired product.

Example 2

α-Methyl-Mannose Triggering in Non-Diabetic Rats 0.300 ml of the formulation prepared in Example 1 was injected subcutaneously into each of three normal male Sprague Dawley (SD) rats (Charles River Laboratories, Wilmington, Mass.) weighing between 400 and 500 g. Prior to formulation injection, blood glucose values were measured via tail vein bleeding using a Precision Xtra glucometer (Abbott Laboratories, Alameda, Calif.) and approximately 100 ul of serum was obtained via tail vein bleeding to assay for background insulin levels. Food was removed from the rat cages during the duration of the study. Serum and blood glucose values were obtained at 30 min, 60 min, 90 min, and 120 min post-injection. At 120 min after the injection, an intraperitoneal injection of a 25% w/v α-methyl-mannose solution was injected to provide a 2 g/kg dose after which serum and blood glucose values were obtained at 135 min, 150 min, 180 min, 210 min, 240 min, and 300 min. Serum insulin concentrations were subsequently measured with a commercially available ELISA kit (Human Insulin ELISA, Mercodia, Uppsala, Sweden) using a standard curve generated from the pure insulin conjugate solution. Endogenous rat insulin does not cross-react on this assay; therefore, any results obtained were due solely to the exogenously administered insulin conjugate and not endogenous rat insulin.

Figure 3:
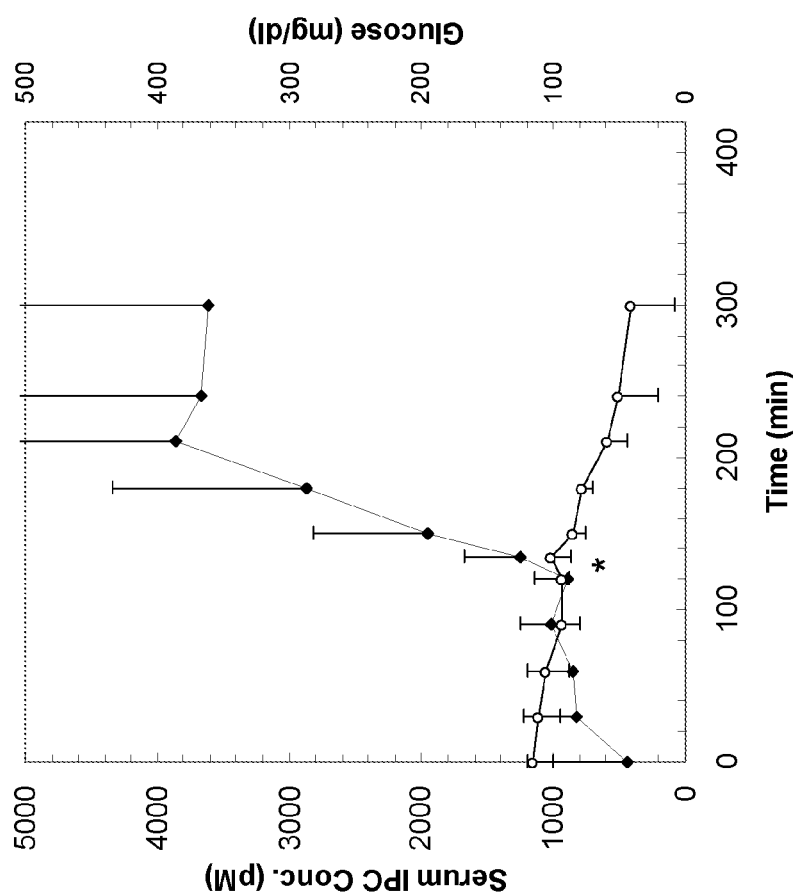
FIG. 3: (a) Plot of (♦) serum insulin and (○) blood glucose levels following subcutaneous injection in non-diabetic SD rats at time 0 with TSB-C4-AEBM-2-insulin/native Con A (an α-methyl mannose-responsive material). An i.p. injection of α-methyl mannose was administered at 120 min as indicated by the *.

FIG. 3 shows ~4× increase in serum insulin concentration from baseline following the intraperitoneal α-methyl-mannose tolerance test (IP(α-MM)TT) indicating α-methyl-mannose-responsive delivery in vivo. Furthermore, very little conjugate was released at physiologically normal blood glucose levels during the first two hours of the experiment and virtually no hypoglycemia was induced prior to the introduction of α-methyl-mannose. However, once the 4× increase in serum insulin-conjugate concentration induced by the exogenously delivered α-methyl-mannose, exerted a significant glucose lowering effect.

Example 3

Synthesis of TSB-C4 Framework

A solution of 1,3,5-benzenetricarbonyl chloride (1 gm, 3.8 mmole) in dichloromethane (DCM) (5 mL) is added dropwise to a vigorously stirring solution of an ω-aminoacid (3.1 equivalents) in 1N NaOH (25 mL) in an ice bath. The ice bath is removed and stirring is continued for 4 hours at room temperature. 2N HCl (~15 mL) is added dropwise to approximately pH 2 and the resulting slurry is stirred for an additional 2 hours. The precipitate is filtered, washed with cold water (2×20 mL) and dried in air under vacuum and then in a 60 C oven overnight. The resulting white solid is used without further purification. Yield for each ω-aminoacid (4-aminobutyric acid: yield 1.6 gm, 91%; 6-aminocaproic acid: yield 1.9 gm, 92%)

The above material is taken into DMSO (5 mL) containing N-hydroxysuccinimide (3.1 mmole, 3.1 equiv.) and N-(3-dimethylaminopropyl)-N'-ethylcarbodiimide (EDCI, 3.6 mmole, 3.6 equiv.) is added at room temperature. The resulting solution is stirred for 24 hours, diluted with water (125 mL) and extracted with ethyl acetate (3×50 mL). The combined organic phase is washed with water (2×50 mL), brine (1×50 mL) and dried over $MgSO_4$. The solvent is evaporated and the semi-solid residue triturated with acetonitrile (10 mL). The solid is filtered and washed with cold solvent, dried in air under vacuum and then in a 60 C oven overnight. The product is free of urea bi-product. Benzene-1,3,5-tricarboxy-(N-6-aminocaproic-NHS ester)amide (TSB-C6): 304 mg, 36%, mp 140-142 C. Benzene-1,3,5-tricarboxy-(N-4-butyric-NHS-ester)amide (TSB-C4): 245 mg, 45%, mp 182-184 C.

Example 4

Synthesis of Azidoethylmannose (AzEM)

a. Synthesis of Bromoethylmannose

DOWEX 50W×4 resin (Alfa Aesar, Ward Hill, Mass.) is washed with deionized water to remove color. A mixture of 225 gm D-mannose (1.25 mol; 1 equiv., Alfa Aesar) and 140 gm DOWEX 50W×4 is treated with 2.2 L 2-bromoethanol (30.5 mol, 25 equiv.; 124.97 gm/mol; 1.762 gm/mL; BP=150 C; Alfa Aesar) and the stirred mixture heated to 80 C for 4 hours. The reaction is monitored by TLC (20% methanol/dichloromethane (DCM)). Reaction is complete after about four hours, and then allowed to cool to room temperature. The solution is filtered to remove the resin, and the resin washed with ethyl acetate and DCM. The resulting filtrate is stripped to an amber oil in a rotory evaporator.

The amber oil is purified on silica gel (4 kg silica packed in DCM) in the following manner. The crude is dissolved in DCM and loaded onto the column, and then eluted with 2×4 L 10% methanol/DCM; 2×4 L 15% methanol/DCM; and 3×4 L 20% methanol/DCM. Product containing fractions (on the basis of TLC) are pooled and stripped to dryness to afford 152 gm of 1-α-bromoethyl-mannose (42%).

b. Conversion of Bromoethylmannose to Azidoethylmannose (AzEM)

A 5 L round bottom three-necked flask, equipped with a heating mantle, an overhead stirrer, and a thermometer, is charged with 150 gm bromoethylmannose (525 mmol). The oil is dissolved in 2 L water and treated with 68.3 gm sodium azide (1.05 mol, 2 equiv.; 65 gm/mol; Alfa-Aesar) followed by 7.9 gm sodium iodide (52.5 mmol, 0.08 equiv.; 149.89 gm/mol; Alfa-Aesar) and the solution warmed to 50 C and stirred overnight. The solution is cooled to room temperature and concentrated to dryness on the rotovap. The solid residue is digested with 3×500 mL of 5:1 vol. $CHCl_3$:MeOH at 40 C. The combined organic portions are filtered and evaporated to dryness to afford azidoethylmannose as an off-white solid.

c. Repurification of Azidoethylmannose 32 gm of azidoethylmannose is taken into 100 mL water. The turbid solution is filtered through a glass microfibre filter (Whatman GF/B). The filtrate is evaporated to a solid on a rotovapor. The solid is taken into Methanol (100 mL) and the turbid solution is again filtered through a glass microfibre filter. The resulting pale yellow filtrate is stripped to a solid under vacuum.

The solid is taken into a minimum of methanol (50 mL) and ethyl acetate (150 mL) is added slowly with stirring. The heavy slurry is cooled and filtered. The solid is air dried (hygroscopic) and put in a 60 C oven overnight. The Mother Liquor is evaporated under vacuum to a yellow gum.

Example 5

Synthesis of Azidoethylmannobiose (AzEBM)

The AzEM compound from Example 4 is selectively protected using benzene dimethyl ether, purified by column chromatography and subsequently reacted with benzyl bromide to give 1-α-(2-azidoethyl)-4,6-benzaldehyde diacetal-3-benzyl-mannopyranoside. The product is subsequently glycosylated with 1-α-bromo-2,3,4,6-tetrabenzoylmannopyranoside using silver triflate chemistry under rigorously anhydrous conditions to give the protected-azidoethylmannobiose product. The intermediate product is then deprotected to remove the benzoyl groups to give AzEBM.

Example 6

Synthesis of Aminoethylmannobiose (AEBM)

The azido-terminated compound from Example 5 is readily hydrogenated at room temperature by using palladium/carbon catalyst, a small amount of acetic acid, and ethanol as a solvent to give the corresponding amine-terminated compounds. The process is identical to the one described for AETM below, except that those skilled in the art will understand that the amounts of reagents, solvents, etc. should be scaled to the number of moles of sugar-ligand to be hydrogenated.

a. Man (α-1,3)-Man(α-1.6)-α-1-aminoethylmannopyranoside ("aminoethyltrimannose", AETM)

To a solution of 5.3 gm (9.25 mmole) man(α-1,3)-man(α-1.6)-α-1-azidoethylmannopyranoside in 100 mL water and 50 mL ethanol was added 0.8 gm 5% Pd/C. The vigorously stirring suspension was hydrogenated at 30-40 psi for 48 hours or until no starting material was apparent by TLC(SG, Methanol, SM $R_f$ 0.75, Pdt $R_f$ 0.0, PMA vis.). The suspension was filtered over celite, which was rinsed with ethanol (2×50 mL) and the filtrate concentrated under vacuum.

HPLC of this material (C18, 3% Acetonitrile/97% 0.1% $H_3PO_4$, 220 nm, 2 ml/min) gave uv adsorption of the injection column void material, $R_t$ 2.5 minutes, indicative of benzoate ester.

The filtrate was diluted with 70 mL water and 12 mL of 1N NaOH and the solution stirred overnight at room temperature (HPLC: no uv material at column void $R_t$ 2.5 min., uv material at $R_t$ 10.5 minutes co-eluting with benzoic acid). 2 gm of decolorizing charcoal were added and the stirring suspension heated to 80 C., cooled to room temperature and filtered over celite. The filtrate pH was adjusted to 8.0 with 2N HCl and the colorless solution concentrated under vacuum to about 50% volume.

The solution was loaded onto a resin column (Dowex 50W, 50 gm) and washed with water until eluting fractions were neutral to pH (6×75 mL) removing any residual acid byproducts. The amine product was washed off the column with 0.25N ammonium hydroxide (6×75 mL) and the fractions containing the amine product-ninhydrin detection were combined and concentrated to 25-30 mL under vacuum. This concentrated solution was added drop-wise to 300 mL stirring ethanol and stirring continued for an additional 2 hours. The product was filtered, washed with fresh ethanol (2×50 mL) and air dried to a constant weight. The resulting white amorphous solid was dried further in a vacuum oven at 80 C for 5 hours to give 4.1 gm of a white granular solid (TY 5.1 gm). The NMR was clean of any aromatic protons. $^1$H NMR 300 MHz (D$_2$O) δ 5.08 (s, 1H), 4.87 (s, 1H), 4.81 (s, 1H), 4.8-3.6 (m, 18H), 2.9 (m, 2H).

Example 7

Synthesis of NH$_2$-B1-BOC2(A1,B29)-insulin

In a typical synthesis, 4 g of powdered insulin (Sigma Aldrich, St. Louis, Mo.) is dissolved in 100 ml of anhydrous DMSO at room temperature followed by the addition of 4 ml of triethylamine (TEA). The solution is stirred for 30 minutes at room temperature. Next, 1.79 ml (2.6 equivalents) of di-tert-butyl-dicarbonate/THF solution (Sigma Aldrich, St. Louis, Mo.) is slowly added to the insulin-TEA solution and mixed for approximately one hour. The reaction is quenched via the addition of 4 ml of a stock solution containing 250 ul of ethanolamine in 5 ml of DMSO followed by mixing for five minutes. After quenching, the entire solution is poured into 1600 ml of acetone and mixed briefly with a spatula. Next, 8×400 ul aliquots of a 18.9% HCl:water solution are added dropwise over the surface of the mixture to precipitate the reacted insulin. The precipitated material is then centrifuged and the supernatant decanted into a second beaker while the precipitate cake is set aside. To the supernatant solution, another 8×400 μA aliquots of a 18.9% HCl:water solution are added dropwise over the surface of the mixture to obtain a second precipitate of reacted insulin. This second precipitate is centrifuged and the supernatant is discarded. The combined centrifuge cakes from the two precipitation steps are washed once with acetone followed by drying under vacuum at room temperature to yield the crude powder which typically contains 60% of the desired BOC2 product and 40% of the BOC3 material.

A preparative reverse phase HPLC method is used to isolate the pure BOC2-insulin from the crude powder. Buffer A is deionized water containing 0.1% TFA and Buffer B is acetonitrile containing 0.1% TFA. The crude powder is dissolved at 25 mg/ml in a 70% A/30% B mixture and syringe filtered prior to injection on the column. Before purification, the column (Waters SymmetryPrep C18, 7 um, 19×150 mm) is equilibrated at 15 ml/minutes with a 70% A/30% B mobile phase using a Waters DeltaPrep 600 system. Approximately 5 ml of the crude powder solution is injected onto the column at a flow rate of 15 ml/minutes over the course of 5 minutes after which a linear gradient is employed from 70% A/30% B to 62% A/38% B over the course of the next 3.5 minutes and held there for an additional 2.5 minutes. Using this method, the desired BOC2 peak elutes at approximately 10.6 minutes followed closely by the BOC3 peak. Once collected, the solution is rotovapped to remove acetonitrile and lyophilized to obtain pure BOC2-insulin powder. Identity is verified by LC-MS (HT Laboratories, San Diego, Calif.) and site of conjugation determined by N-terminal sequencing (Western Analytical, St. Louis, Mo.).

Example 8

Synthesis of Conjugate

The TSB-C4 framework is dissolved at 60 mM in 1.0 ml of anhydrous DMSO followed by the addition of 400 ul (excess) of triethylamine (TEA). The solution is stirred rapidly for 10 minutes at room temperature. The NH$_2$-B1-BOC2(A1,B29)-insulin (MW=6,008 g/mol) is then dissolved separately in 7.9 ml of DMSO at a concentration of 7.4 mM. Once dissolved, the entire drug solution is added dropwise over the course of 10 minutes to the framework/DMSO/TEA solution followed by room temperature mixing for two hours. The remaining activated esters are then reacted with the amine-functionalized AEBM affinity ligands in the following manner. A 370 mM solution of affinity ligand is prepared in an appropriate volume of dry DMSO. Once dissolved, enough solution is added to provide a number of reactive equivalents equal to three times the number of initial activated ester groups, N, minus one. For example, if there are N=3 initial activated ester groups per framework, then (3×(3−1)×60 mM/370 mM)=0.973 ml of affinity ligand solution are added. If there are N=4 initial activated ester groups per framework, then (3×(4−1)×60 mM/370 mM)=1.46 ml of affinity ligand solution are added, and so on. After the affinity ligand solution is added, the solution is stirred for one more hour at room temperature to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters C8, 7 um, 19×150 mm column. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltaPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and affinity ligand used. Once collected, the solution is rotovapped to remove acetonitrile and lyophilized to obtain pure conjugate whose identity may be verified by LC-MS (HT Laboratories, San Diego, Calif.). Because the starting NH$_2$-B1-BOC2(A1,B29)-insulin material only possesses one free amine group at the Phe-B1 terminus, the Phe-B1 is the only site of insulin conjugation to the framework as verified in each deprotected final product by N-terminal sequencing.

Example 9

Conjugates of Formula (I)

This example describes some exemplary conjugates of formula (I):

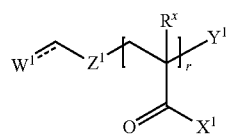

Yet other embodiments of these conjugates as well as intermediates and methods of making these conjugates can be found in U.S. Provisional Application No. 61/162,105 filed Mar. 20, 2009 and corresponding PCT application filed on Jan. 27, 2010. The entire contents of these related applications are incorporated herein by reference.

In certain embodiments, a conjugate of formula (I) may include one or more of the following exemplary groups:

$R^x$

In certain embodiments, $R^x$ is hydrogen. In certain embodiments, $R^x$ is optionally substituted $C_{1-6}$ alkyl. In certain embodiments, $R^x$ is optionally substituted $C_{1-3}$ alkyl. In certain embodiments, $R^x$ is optionally substituted methyl. In certain embodiments, $R^x$ is —$CH_3$.

$Z^1$

In certain embodiments, $Z^1$ is an optionally substituted bivalent $C_{1-10}$, $C_{1-8}$, $C_{1-6}$, $C_{1-4}$, or $C_{1-2}$ hydrocarbon chain. In certain embodiments, $Z^1$ is —(CH$_2$)—, —(CH$_2$CH$_2$)—, —(CH$_2$CH$_2$CH$_2$)—, —(CH$_2$CH$_2$CH$_2$CH$_2$)—, —(CH$_2$CH$_2$CH$_2$CH$_2$CH$_2$)—, or —(CH$_2$CH$_2$CH$_2$CH$_2$CH$_2$CH$_2$)—. In certain embodiments, $Z^1$ is —(CH$_2$)— or —(CH$_2$CH$_2$)—. In certain embodiments, $Z^1$ is —(CH$_2$)—. In certain embodiments, $Z^1$ is —(CH$_2$CH$_2$)—. In certain embodiments, $Z^1$ is —(CH$_2$CH$_2$CH$_2$)—. In certain embodiments, $Z^1$ is —(CH$_2$CH$_2$CH$_2$CH$_2$)—.

In certain embodiments, $Z^1$ is an optionally substituted bivalent $C_{1-10}$ hydrocarbon chain, wherein 1, 2 or 3 methylene units of $Z^1$ are optionally and independently replaced with one or more groups selected from —S—, —O—, —NR$^a$—, —(C=NR$^a$)—, —(C=O)—, —(S=O)—, —S(=O)$_2$—, —(CR$^b$=CR$^b$)—, —(N=N)—, an optionally substituted arylene moiety or an optionally substituted heteroarylene moiety. In certain embodiments, $Z^1$ is an optionally substituted bivalent $C_{1-10}$ hydrocarbon chain, wherein 1, 2 or 3 methylene units of $Z^1$ are optionally and independently replaced with one or more groups selected from —S—, —O—, —NR$^a$—, —(C=NR$^a$)—, or —(C=O)—. In certain embodiments, $Z^1$ is —CH$_2$CH$_2$NH(C=O)C(CH$_3$)$_2$—, —CH$_2$CH$_2$N(C=NH)(CH$_2$)$_3$S—, —CH(R$^f$)$_2$, —CH$_2$CH(R$^f$)$_2$, —CH$_2$CH$_2$CH(R$^f$)$_2$—, —CH$_2$S—, or —CH$_2$CH$_2$S—, wherein R$^f$ is optionally substituted aliphatic, optionally substituted heteroaliphatic, optionally substituted aryl, optionally substituted heteroaryl (e.g., in certain embodiments, R$^f$ is optionally substituted aryl; in certain embodiments, R$^f$ is phenyl). In certain embodiments, $Z^1$ is —CH$_2$CH$_2$NH(C=O)C(CH$_3$)$_2$— or —CH$_2$CH$_2$N(C=NH)(CH$_2$)$_3$S—. In certain embodiments, $Z^1$ is —CH$_2$CH$_2$NH(C=O)C(CH$_3$)$_2$—. In certain embodiments, $Z^1$ is —CH$_2$CH$_2$N(C=NH)(CH$_2$)$_3$S—.

$Y^1$

In certain embodiments, $Y^1$ is a fragment of a free radical initiator. Such a fragment is encompassed by the definition of $Y^1$, as initiator fragments may include halogen, —OR$^c$, —SR$^c$, optionally substituted aliphatic, optionally substituted heteroaliphatic, optionally substituted aryl, and optionally substituted heteroaryl moieties.

In certain embodiments, $Y^1$ is hydrogen, halogen, or an initiator fragment. In certain embodiments, $Y^1$ is hydrogen or halogen. In certain embodiments, $Y^1$ is hydrogen or bromine.

$X^1$

In certain embodiments, $X^1$ is —OR$^c$. In certain embodiments, $X^1$ is a mixture of —OR$^c$ and —N(R$^d$)$_2$. In certain embodiments, $X^1$ is —N(R$^d$)$_2$.

$W^1$ and ≈≈≈≈≈

In certain embodiments, ≈≈≈≈≈ is a single covalent bond.

In certain embodiments, $W^1$ is covalently bound to the polymer via an amino group. In certain embodiments, $W^1$ is covalently bound to the polymer via a primary amino group.

For example, in certain embodiments, the group

corresponds to the group

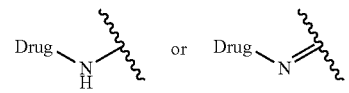

wherein the group [Drug-NH-] or [Drug-N=] is the drug directly covalently conjugated via a primary amino group. In other embodiments, the drug may include a spacer group (e.g., an alkylene group, arylene group, heteroarylene group, ester linkage, amide linkage, and the like) which terminates with a pendant amino group. The latter embodiments enable greater separation between the active portion of the drug and the polymer.

r

In certain embodiments, r is an integer between 10-25, inclusive. In certain embodiments, r is an integer between 15-25, inclusive. In certain embodiments, r is an integer between 20-25, inclusive. In certain embodiments, r is an integer between 5-20, inclusive. In certain embodiments, r is an integer between 10-20, inclusive. In certain embodiments, r is an integer between 15-20, inclusive. In certain embodiments, r is 5, 6, 7, 8, 9, 10, 11, 12, 13, 14, 15, 16, 17, 18, 19, 20, 21, 22, 23, 24 or 25. In certain embodiments r is 5. In certain embodiments r is 10. In certain embodiments r is 15. In certain embodiments r is 20. In certain embodiments r is 25.

In certain embodiments, the group:

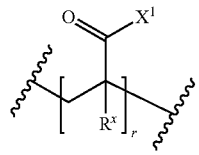

corresponds to a mixture of the groups:

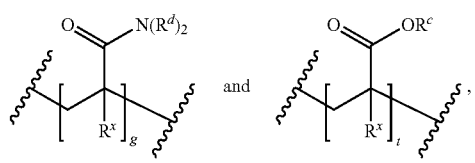

wherein the sum of (g+t) is equal to r. In certain embodiments, each instance of g and t is, independently, an integer between 1 and 24, inclusive, with the proviso that the sum of (g+t) is greater than or equal to 5 and less than or equal to 25. In certain embodiments, g and t are present in a ratio of about 1:10, 1:9, 1:8, 1:7, 1:6, 1:5, 1:4, 1:3, 1:2, or 1:1 (g to t). In certain embodiments, t and g are present in a ratio of about 1:10, 1:9, 1:8, 1:7, 1:6, 1:5, 1:4, 1:3, or 1:2 (t to g).

Exemplary Conjugates

In certain embodiments, a conjugate of formula (I-a1) may be used:

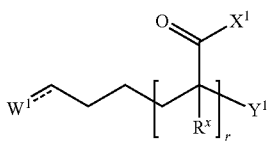

In certain embodiments, a conjugate of formula (I-a2) may be used:

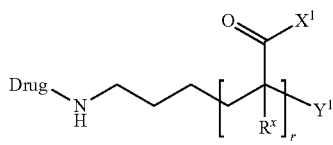

In certain embodiments, a conjugate of formula (I-b1) may be used:

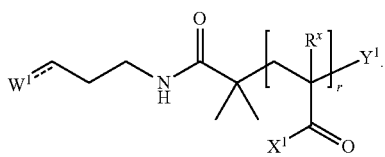

In certain embodiments, a conjugate of formula (I-b2) may be used:

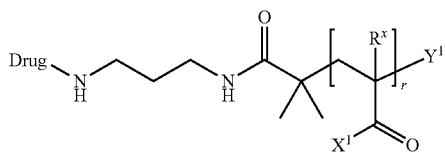

In certain embodiments, a conjugate of formula (I-c1) may be used:

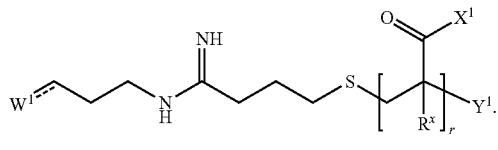

In certain embodiments, a conjugate of formula (I-c2) may be used:

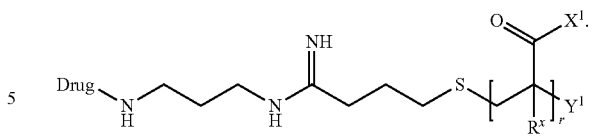

In any of these exemplary conjugates, the group:

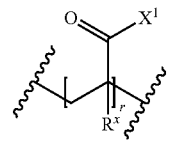

may correspond to a mixture of the groups:

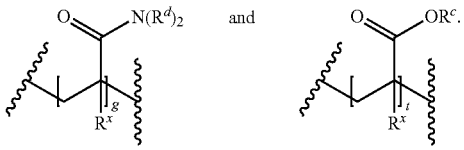

wherein the sum of (g+t) is equal to r, respectively. In certain embodiments, r is 10. In certain embodiments, r is 20.

Characterization of Conjugates

The conjugates can be characterized by any analytical method including nuclear magnetic resonance (e.g., $^1$H NMR); gel permeation chromatography (GPC) for molecular weight and polydispersity; and Fourier transform infrared spectroscopy (FTIR) or acid titration for determination of the number of acid groups per chain.

In certain embodiments the conjugate framework (i.e., without including the affinity ligands or drug) has a molecular weight of less than 10,000 Da, e.g., in the range of about 100 to about 10,000 Da. In certain embodiments, the conjugate framework has a molecular weight in the range of about 300 to about 5,000 Da. In certain embodiments, the conjugate framework has a molecular weight in the range of about 500 to about 2,500 Da. In certain embodiments, the conjugate framework has a molecular weight in the range of about 1,000 to 2,000 Da. In certain embodiments, the conjugate framework has a molecular weight in the range of about 200 to 1,000 Da. In certain embodiments, the conjugate framework has a molecular weight in the range of about 300 to 800 Da.

In certain embodiments, a mixture of conjugates is generated. The conjugates in this mixture may have the same or different molecular weights. In one embodiment, the polydispersity of the mixture is less than 1.5. In one embodiment, the polydispersity of the mixture is less than 1.25.

Example 10

Conjugates of Formula (II)

This example describes some exemplary conjugates of formula (II):

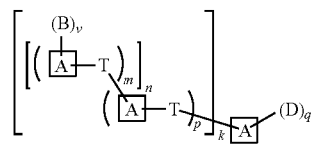

Yet other embodiments of these conjugates as well as intermediates and methods of making these conjugates can be found in U.S. Provisional Application No. 61/147,878 filed Jan. 28, 2009, U.S. Provisional Application No. 61/159,643 filed Mar. 12, 2009, U.S. Provisional Application No. 61/162,107 filed Mar. 20, 2009, U.S. Provisional Application No. 61/163,084 filed Mar. 25, 2009, U.S. Provisional Application No. 61/219,897 filed Jun. 24, 2009, U.S. Provisional Application No. 61/223,572 filed Jul. 7, 2009, U.S. Provisional Application No. 61/252,857 filed Oct. 19, 2009, and corresponding PCT application filed on Jan. 27, 2010. The entire contents of these related applications are incorporated herein by reference.

In some embodiments, the present disclosure provides conjugates of general formula (II-a1):

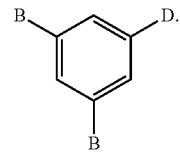

For example, in some embodiments, the present disclosure provides conjugates of formula:

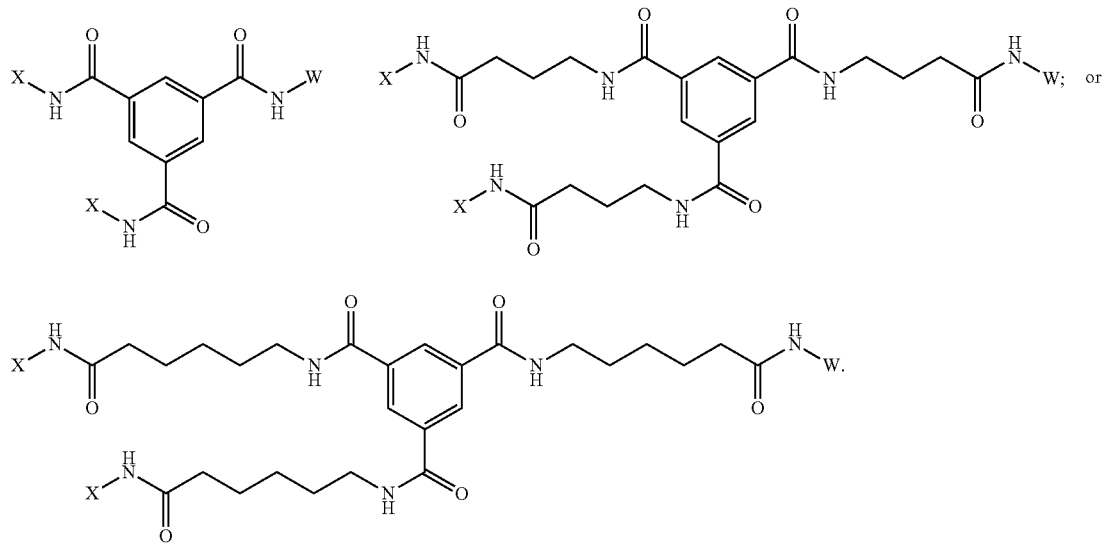

In some embodiments, the present disclosure provides conjugates of general formula (II-a2):

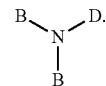

For example, in some embodiments, the present disclosure provides conjugates of formula:

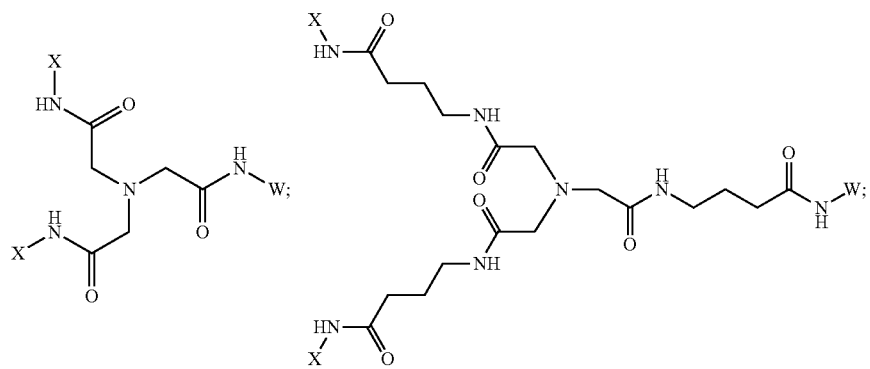

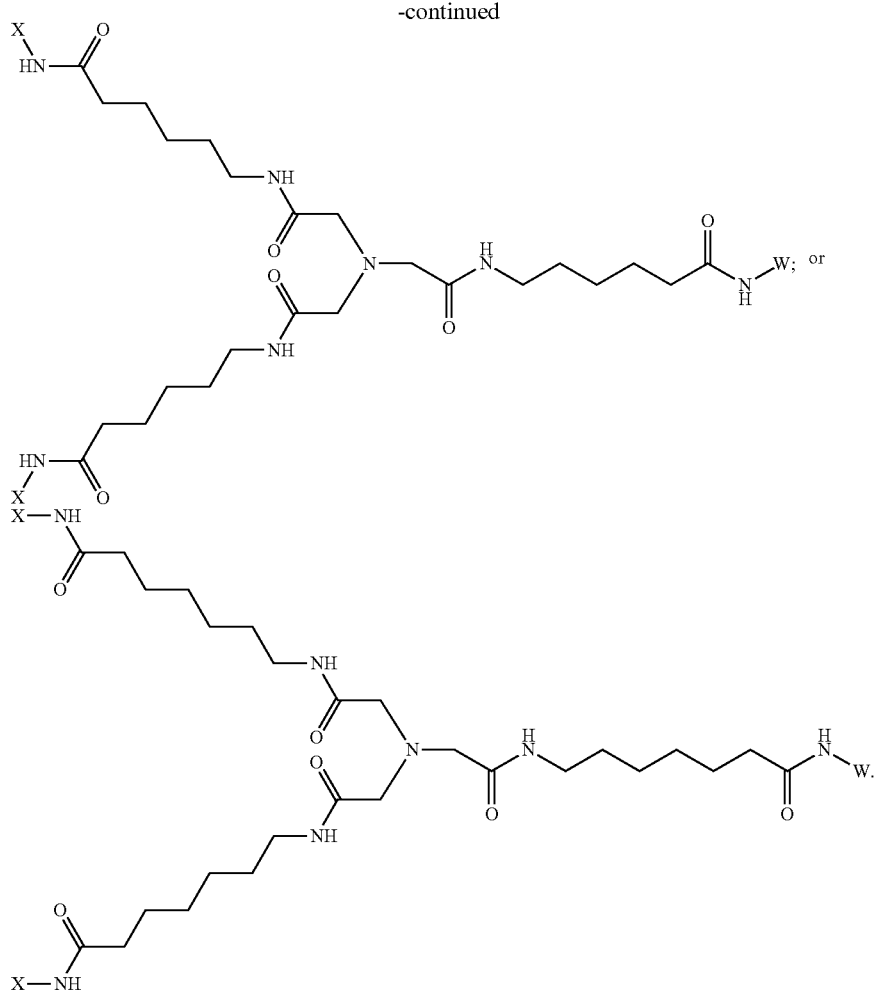

In some embodiments, the present disclosure provides conjugates of general formula (II-a3):

For example, in some embodiments, the present disclosure provides conjugates of formula:

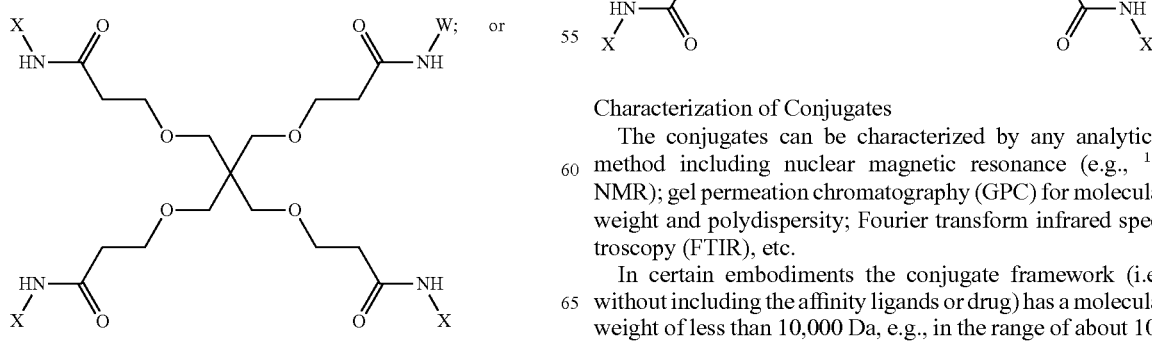

Characterization of Conjugates

The conjugates can be characterized by any analytical method including nuclear magnetic resonance (e.g., $^1$H NMR); gel permeation chromatography (GPC) for molecular weight and polydispersity; Fourier transform infrared spectroscopy (FTIR), etc.

In certain embodiments the conjugate framework (i.e., without including the affinity ligands or drug) has a molecular weight of less than 10,000 Da, e.g., in the range of about 100 to about 10,000 Da. In certain embodiments, the conjugate framework has a molecular weight in the range of about 300 to about 5,000 Da. In certain embodiments, the conjugate framework has a molecular weight in the range of about 500 to about 2,500 Da. In certain embodiments, the conjugate framework has a molecular weight in the range of about 1,000 to 2,000 Da. In certain embodiments, the conjugate framework has a molecular weight in the range of about 200 to 1,000 Da. In certain embodiments, the conjugate framework has a molecular weight in the range of about 300 to 800 Da.

Example 11

Synthesis of Azidophenyl-Sugar Modified Conjugates

This example and those that follow describes the preparation of some exemplary binding-site modified lectins that could be used to prepare a material of the present disclosure.

All steps were performed at room temperature unless otherwise specified. First, 5.0 g of native Con A (Sigma-Aldrich, St. Louis, Mo.) was dissolved in 200 ml of a 10 mM pH 5.0 acetate buffer solution containing 150 mM sodium chloride, 2 mM calcium chloride, 2 mM manganese chloride, and 0.1% w/v sodium azide (S28 buffer) and any insoluble material was separated by centrifugation and/or filtration. We have found that different commercial preparations of native Con A contain appreciable concentrations of inhibitory sugars that are, in certain embodiments, removed prior to photoaffinity modification. To that end, the solution was purified through a Biogel-P6 size exclusion column with an S28 mobile phase two times. Finally, the resulting solution was diluted with S28 to a final volume of 1 L. Under gentle stirring conditions, 0.4 g of hydroquinone (Sigma-Aldrich, St. Louis, Mo.) was added followed by 165 mg of either azidophenylglucose (APG, PolyOrg Inc., Leominster, Mass.) or azidophenylmannose (APM, PolyOrg. Inc., Leominster, Mass.). The solution was stirred in the dark at 4 C for one hour at the lowest possible stir speed. After one hour of stirring, any additional insoluble material was removed via centrifugation and/or filtration. 200 ml of the solution was poured into a 9"×13" aluminum pan and reacted at 4 C inside a CL-1000 UV crosslinking oven (UVP, Upland, Calif.) for 15 min at 360 nm (the UV reaction may also take place using 302 nm light). Following the reaction, any additional insoluble material was removed via centrifugation and/or filtration. The clarified solution was then purified 1× through Biogel-P6 size exclusion columns (Econopak, Bio-Rad Labs, Hercules, Calif.) with an S28 mobile phase. The UV crosslinking reaction and P6 purification process was then repeated until the entire solution was reacted. Finally, the combined P6-purified solutions were concentrated down to ~180 ml using a Pall tangential flow filtration cartridge apparatus (Millipore, Billerica, Mass.) equipped with Omega 30K membranes. The resulting solution was clarified via centrifugation and/or filtration and passed through 0.22 um filters prior to affinity column purification.

Example 12

Generalized Synthesis of Diazirine Photoreactive Ligands 0.9 mmol of aminoethyl (AE) functionalized sugar ligand (e.g., AEG, AEM, AEBM, AETM) were dissolved in 4 ml of anhydrous DMSO after which 1.6 ml of anhydrous triethylamine (TEA) were added to form a cloudy emulsion. In a separate container, 200 mg (0.9 mmol) of NHS-diazirine (Thermo Fisher Scientific Inc., Rockford, Ill.) powder was dissolved in 4 ml of anhydrous DMSO under dark conditions. Once dissolved, the NHS-diazirine solution was added dropwise to the AE-sugar solution and then allowed to react overnight at room temperature in the dark. TLC analysis (50% ethanol:50% ethyl acetate) of the overnight solution confirmed complete reaction as evidenced by the co-elution of the UV signal of the diazirine moiety (254 nm) and the sugar signal (sulfuric acid-ethanol stain) and concomitant disappearance of the AE-functionalized sugar ligand from the origin of the TLC (sulfuric acid-ethanol stain). The solution was then diluted into 80 ml of a pH 5.0, 25 mM HEPES solution containing 0.15 M sodium chloride, pH adjusted to pH 5 if necessary, and then frozen until required for photoaffinity reaction with Con A.

Example 13

Synthesis and Characterization of Sugar-Functionalized Diazirine Con A

All steps were performed at room temperature unless otherwise specified. First, 5.0 g of native Con A (Sigma-Aldrich, St. Louis, Mo.) was dissolved in 200 ml of a 10 mM pH 5.0 acetate buffer solution containing 150 mM sodium chloride, 2 mM calcium chloride, 2 mM manganese chloride, and 0.1% w/v sodium azide (S28 buffer) and any insoluble material were separated by centrifugation and/or filtration. We have found that different commercial preparations of native Con A contain appreciable concentrations of inhibitory sugars that are, in certain embodiments, removed prior to photoaffinity modification. To that end, the solution was purified through a Biogel-P6 size exclusion column with an S28 mobile phase two times. Finally, the resulting solution was diluted with S28 to a final volume of 1 L. Next, the solution volume was brought up to 1 L-1/3 ligand volume, using 1,628 and poured into a 1 L media bottle with stir bar. Under gentle stirring conditions in the dark, 0.4 g of hydroquinone (Sigma-Aldrich, St. Louis, Mo.) was dissolved. Next, 33 ml of the diazirine-sugar conjugate obtained in Example 43 was added in 7 aliquots under gentle stirring conditions in the dark. Once dissolved, the entire solution was incubated under gentle stirring for an additional 10 min at 4 C in the dark. After 10 min of stirring, any additional insoluble material was removed via centrifugation and/or filtration. 250 ml of the solution was poured into a 9"×13" aluminum pan and reacted at 4 C inside a CL-1000 UV crosslinking oven (UVP, Upland, Calif.) for 15 min at 360 nm. Following the reaction, any additional insoluble material was removed via centrifugation and/or filtration. The clarified solution was then purified 1× through Biogel-P6 size exclusion columns (Econopak, Bio-Rad Labs, Hercules, Calif.) with an S28 mobile phase. The UV crosslinking reaction and P6 purification process was then repeated until the entire solution was reacted.

Finally, the combined P6-purified solutions were concentrated down to ~180 ml using a Pall tangential flow filtration cartridge apparatus (Millipore, Billerica, Mass.) equipped with Omega 30K membranes. The resulting solution was clarified via centrifugation and/or filtration and passed through 0.22 um filters prior to affinity column purification.

Other Embodiments

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

We claim:

1. A cross-linked material comprising:
multivalent cross-linking agents that are capable of binding an exogenous target molecule that includes a saccharide; and
conjugates that include a drug and two or more separate affinity ligands bound to a polymeric conjugate framework, wherein
(i) the two or more affinity ligands are capable of competing with the exogenous target molecule for binding with the cross-linking agents;
(ii) the conjugates are cross-linked within the material as a result of non-covalent interactions between the cross-linking agents and the affinity ligands on different conjugates;
(iii) wherein each affinity ligand includes a saccharide; and
(iv) the conjugate is of the general formula:

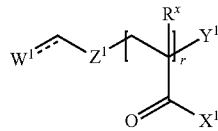

I wherein:
$R^x$ is hydrogen or optionally substituted $C_{1-6}$ alkyl;
$Z^1$ is an optionally substituted bivalent $C_{1-10}$ hydrocarbon chain, wherein 1, 2, 3, 4 or 5 methylene units of $Z^1$ are optionally and independently replaced with one or more groups selected from —S—, —O—, —$NR^a$—, —(C=$NR^a$)—, —(C=O)—, —(S=O)—, —S(=O)$_2$, —($CR^b$=$CR^b$)—, —(N=N)—, an optionally substituted arylene moiety or an optionally substituted heteroarylene moiety, wherein $R^a$ is hydrogen, optionally substituted aliphatic, optionally substituted heteroaliphatic, optionally substituted aryl, optionally substituted heteroaryl, or a suitable amino protecting group; and $R^b$ is hydrogen, optionally substituted aliphatic, optionally substituted heteroaliphatic, optionally substituted aryl, or optionally substituted heteroaryl;
each occurrence of $X^1$ is independently —$OR^c$ or —$N(R^d)_2$, wherein $R^c$ is hydrogen, optionally substituted aliphatic, optionally substituted heteroaliphatic, optionally substituted aryl, optionally substituted heteroaryl, a suitable hydroxyl protecting group, a cation group, or an affinity ligand, and each $R^d$ is, independently, hydrogen, optionally substituted aliphatic, optionally substituted heteroaliphatic, optionally substituted aryl, optionally substituted heteroaryl, a suitable amino protecting group, or an affinity ligand, with the proviso that at least two occurrences of $X^1$ include an affinity ligand;
$Y^1$ is hydrogen, halogen, optionally substituted aliphatic, optionally substituted heteroaliphatic, optionally substituted aryl, optionally substituted heteroaryl, —$OR^e$ or —$SR^e$ wherein $R^e$ is hydrogen, optionally substituted aliphatic, optionally substituted heteroaliphatic, optionally substituted aryl, or optionally substituted heteroaryl;
r is an integer between 5-25, inclusive;
$W^1$ is a drug wherein the exogenous target molecule is α-methyl-mannose; and
===== corresponds to a single or double covalent bond.

2. The material of claim 1, wherein the affinity ligands of the conjugates include a saccharide selected from glucose, mannose, glucosamine, mannosamine, methylglucose, methylmannose, ethylglucose, and ethylmannose.

3. The material of claim 1, wherein the affinity ligands of the conjugates include a bimmanose or branched trimannose.

4. The material of claim 1, wherein the affinity ligands of the conjugates include aminoethylglucose (AEG), aminoethylmannose (AEM), aminoethylfucose (AEF), aminoethylbimannose (AEBM), or aminoethyltrimannose (AETM).

5. The material of claim 1, wherein the multivalent cross-linking agents include a lectin.

6. The material of claim 5, wherein the lectins are covalently bonded to a recognition element, wherein the recognition element competes with the exogenous target molecule and affinity ligands of the conjugate for binding to the lectin, and the lectin has a higher affinity for the affinity ligands of the conjugate than for the recognition element.

7. The material of claim 6, wherein the exogenous target molecule is a saccharide and both the affinity ligands of the conjugate and the recognition element include a saccharide.

8. The material of claim 1, wherein the multivalent cross-linking agents include a peptide aptamer.

9. The material of claim 1, wherein the multivalent cross-linking agents include a polynucleotide aptamer.

10. The material of claim 1, wherein the drug is an insulin molecule.

11. A method comprising administering a material of claim 1 to a patient and subsequently administering a triggering amount of the exogenous target molecule to the patient.

\* \* \* \* \*